United States Patent [19]
Bozich et al.

[11] Patent Number: 5,426,720
[45] Date of Patent: Jun. 20, 1995

[54] NEUROCONTROLLED ADAPTIVE PROCESS CONTROL SYSTEM

[75] Inventors: Daniel J. Bozich; H. Bruce MacKay; Jay A. Eggert, all of San Diego; Ernest E. Muenchau, Vista, all of Calif.

[73] Assignee: Science Applications International Corporation, San Diego, Calif.

[21] Appl. No.: 123,642

[22] Filed: Sep. 17, 1993

Related U.S. Application Data

[62] Division of Ser. No. 605,585, Oct. 30, 1990, Pat. No. 5,367,612.

[51] Int. Cl.$^6$ ......................... H04B 15/00; G21C 7/36
[52] U.S. Cl. ......................................... 395/22; 395/24; 395/903; 364/508; 318/114
[58] Field of Search ................... 395/22, 24, 903, 904, 395/906; 364/508; 318/114, 561

[56] References Cited

U.S. PATENT DOCUMENTS

| | | | |
|---|---|---|---|
| 3,829,750 | 8/1974 | Centner et al. | 318/561 |
| 4,209,776 | 6/1980 | Frederick | 340/541 |
| 4,450,530 | 5/1984 | Llinas et al. | 395/86 |
| 4,823,053 | 4/1989 | McCracken et al. | 318/114 |
| 4,857,912 | 8/1984 | Everett, Jr. et al. | 901/46 |
| 4,999,534 | 3/1991 | Andrianos | 318/114 |
| 5,023,045 | 6/1991 | Wantanabe et al. | 395/24 |
| 5,092,343 | 5/1992 | Spitzer et al. | |
| 5,093,792 | 3/1992 | Taki et al. | |
| 5,138,924 | 8/1992 | Ohya et al. | 84/604 |
| 5,146,541 | 9/1992 | Speidel | 395/24 |
| 5,159,660 | 10/1992 | Lu et al. | 395/22 |
| 5,233,540 | 8/1993 | Andersson et al. | 364/508 |

OTHER PUBLICATIONS

Wang et al, "Self-Adaptive Neural Architectures for Control Applications", International Joint Conf. of Neural Network, Jun. 17-21, 1990.
Bleuler et al, "Nonlinear Neural Network Control with Application Example", Inter. Neural Network Conf. (INNC), Jul. 9-13, 1990.
Psaltis et al, "A Multilayered Neural Network Conroller"; 1988 IEEE.
Hecht-Nielsen, Robert, "Neurocomputing: Picking the Human Brain", *IEEE Spectrum*, pp. 36-41 (Mar. 1988).
Widrow, et al., *Adaptive Signal Processing*, pp. 285-297 (Prentice-Hall, 1985).
Graf, et al., "VLSI Implementation of a Neural Network Model", *Computer*, pp. 41-49 (Computer Society of IEEE, Mar. 1988).

*Primary Examiner*—Allen R. MacDonald
*Assistant Examiner*—George Davis
*Attorney, Agent, or Firm*—Fitch, Even, Tabin & Flannery

[57] ABSTRACT

An adaptive process control system selectively controls vibrations in a given medium in real time. Unwanted vibrations present at a point being monitored in a given medium are sensed, and the system generates an appropriate offsetting vibration that is applied to the medium at a convenient location, which may be remote from the monitored point. The system includes a vibration sensor, such as one or more accelerometers, that sense both input and output vibrations present within the medium; at least one vibration generator, such as an electromagnetic shaker, that generates appropriate offsetting vibrations that are applied to the medium at one or more appropriate locations; and a neural network controller that controls the vibration generator(s) so as to force the sensed vibration at the monitored point(s) to a desired level. The adaptive vibration cancellation provided by the invention takes place in real time, and without the need to process time-consuming complex mathematical algorithms. A specific embodiment of the neural network controller includes a plurality of 4-layer neural networks configured in an adaptive filtered-x configuration.

8 Claims, 12 Drawing Sheets

NEUROCONTROLLED ADAPTIVE PROCESS CONTROL SYSTEM

This is a division, of application Ser. No. 07/605,585, filed 10/30/90, U.S. Pat. No. 5,367,612.

BACKGROUND OF THE INVENTION

The present invention relates to adaptive process control systems, such as adaptive vibration control systems. More particularly, one embodiment of the invention relates to a multiple-input multiple-output (MIMO) adaptive vibration control system controlled by an artificial neural system that generates, cancels, and/or reduces vibrations in a rigid or semi-rigid (e.g., solid) or fluid (gaseous or liquid) medium.

All processes that use or produce power are susceptible to vibration. Rotating machinery-driven equipment, such as turbine generators, cooling pumps, boiler feed water pumps, forced air draft fans, condenser pumps, conveyor belts, propulsion systems, lathes, mills, grinders, and other manufacturing machines are but a few of the more critical plant systems whose performance may be affected by vibration, either directly or indirectly. Vibration transmitted to neighboring structures or machines may also be detrimental. For example, operators of heavy machinery, trucks, aircraft, or spacecraft, to name but a few, may suffer fatigue due to excessive vibration and noise. Buildings and other rigid structures may suffer permanent damage due to vibrations caused by earthquake. Delicate instrumentation, laser and optical bench systems, automatic machinery, robots, cameras, etc., may also be adversely affected by vibration. Thus, there is a need in the art for vibration reduction systems that can be readily adapted to reduce or cancel undesired vibrations in any given type of system where undesirable vibrations may be present.

Vibrations may be transmitted through solid, liquid or gaseous mediums. Most of the examples presented above relate to vibrations in a solid medium, e.g., vibrations that appear in a metal housing, bearing, or other rigid or semi-rigid structures. It is to be emphasized, however, that vibrations may also be felt and transmitted in a fluid medium (gas or liquid), and that such vibrations may also be detrimental. For example, the vibrations associated with the motor of an underwater craft are readily transmitted through the water and make detection of the location of the craft by an unfriendly source relatively simple. Further, the vibrations associated with normal speech are readily transmitted through air, and are thus available for an unfriendly eavesdropper to hear. Further, any audible sound or vibration present in a fluid medium (whether air or water) may comprise distracting background noise that needs to be eliminated before a desired operation can be carried out. Thus, there is also a need in the art for systems that reduce or cancel vibrations in a fluid medium as well as in a solid medium.

Unfortunately, effectively eliminating or reducing vibrations in a solid medium presents a formidable task. While sometimes "shock absorbers" or equivalent devices, may be used to isolate a source of vibrations from a medium remote from the source, such devices are rarely effective at reducing or eliminating vibrations within a given medium when the source of the vibrations is also within the medium.

In order to reduce vibrations that cannot be eliminated through absorber-type isolation devices, it is known in the art to set up counter-vibrations using a suitable vibration source for the purpose of canceling the unwanted vibrations at a desired target point within the medium. Unfortunately, predicting the type and amplitude of the counter-vibrations that must be applied at a given point of the medium in order to effectively cancel the unwanted vibrations at a desired target point within the medium poses an extremely complex problem that is not easily solved. Moreover, the difficulty of this problem is significantly compounded when the problem must be solved in real time. Further, the complexity of the problem expands enormously if either the target point moves or if the character and nature of the unwanted vibration (source vibration) changes.

The vibration cancellation problem becomes virtually impossible to solve using classical techniques when there is more than one desired target point in the same medium that is to be quieted. Further, when a fluid medium is involved, the problem becomes even more difficult due to the non-rigid dynamics of the fluid medium itself. What is needed, therefore, is a vibration reduction system that readily reduces vibrations in real time at one or more target locations in a desired medium, regardless of whether the medium is rigid or fluid, and regardless of the types of vibrations that may be present at the target point(s), and regardless of the location within the medium of the desired target point(s).

Moreover, for some applications, there is a need for a vibration generation system, e.g., a system that generates a desired vibration at the target point that has specified characteristics. For example, the output of vibration actuators are often nonlinear, that is, they produce an output that is distorted both in amplitude and frequency as compared to an input. Therefore, there is a need in the art to linearize the actuator output such that it faithfully reproduces the desired input signal. A vibration generation system has wide applicability, for example, in shake tables and fixtures used to subject various objects and structures to a wide variety of forces, and in seismic oil exploration equipment.

The present invention advantageously addresses the above and other needs.

SUMMARY OF THE INVENTION

The present invention provides an adaptive vibration control system suitable for controlling, generating, canceling, reducing, conditioning, or interpreting vibrations in real time. As used herein, the term "vibration(s)" refers to any mechanical or acoustical oscillation or other movement of an object or a wave that occurs in a solid, fluid or electrical medium. The term "vibration control" refers to the generation, cancellation, reduction, conditioning, interpretation, or other processing of a vibration in real time.

In accordance with one aspect of the present invention, there is provided an adaptive vibration control system that senses unwanted vibrations (source vibrations) present in a given medium, and that generates an appropriate offsetting vibration that is applied to the medium at at a convenient location. The offsetting vibration is transmitted through the medium, from a convenient application point, to a desired monitoring point where the source vibration is to be canceled. At the monitoring point, the offsetting vibration, if of the right amplitude and phase, becomes a counter-vibration that cancels the unwanted vibration. If the applied offsetting vibration does not cancel the unwanted vibration at the specified monitoring point to within an acceptable tolerance, then the applied offsetting vibration is automatically altered or adapted until the desired cancellation at the monitoring point is obtained.

Advantageously, the adaptive vibration cancellation provided by the invention takes place in real time, without the need to process complex mathematical algorithms. Vibration cancellation is achieved at any given point within the medium, for almost any type of vibration, within just a few seconds.

In accordance with another aspect of the invention, a multiple-input multiple-output (MIMO) adaptive vibration control system is provided that senses vibrations at multiple monitored locations within a given medium, and that generates multiple offsetting vibrations. The multiple offsetting vibrations are applied to the medium at different locations throughout the medium. The offsetting vibrations are simultaneously transmitted through the medium and combine at the multiple monitored locations to cancel the unwanted vibration at each monitored location. Advantageously, the MIMO adaptive vibration control system operates in real time, without the need to process complex mathematical algorithms. The monitored points whereat the vibrations are controlled may be moved within the medium as desired. Vibration cancellation or other control is achieved at all of the multiple monitored points, for almost any type of vibration, within a very short time.

The adaptive vibration control system of the present invention, whether configured to monitor and control a single point or multiple points within a given medium, and whether using one or multiple sources of offsetting vibrations, includes at least the following elements: (1) source sensing means for sensing a vibration present in the medium from one or more vibration source(s); (2) error sensing means for sensing vibrations at the desired monitoring point(s); (3) at least one vibration generating means for generating at least one offsetting vibration that is applied to the medium at least one location; and (4) control means responsive to the source and error sensing means for controlling the vibration generating means so as to force the sensed vibration at the at least one desired monitoring point to a desired level, e.g., to zero.

Advantageously, the control means of the present invention comprises an artificial neural network, or neurocomputer. Such network or neurocomputer includes many processing elements, each connected to many others, arranged in multiple layers. An input array, or sequence of signals (numbers) from the source sensing means, is entered into a first layer of the network in a time series. This signal propagates forward through the array. The signal(s) from the error sensing means are applied to the output layer of the network and propagate backwards through the array. Each processing element in the first layer takes a component of the input array, operates on it in parallel with the other processing elements in the layer according to a prescribed transfer function, and delivers a single output to the processing elements in a second layer. The prescribed transfer function typically involves multiplying the received signal by an adaptive coefficient, or weight. The adaptive coefficient or weight is adapted by the backward propagation of the error signal(s). Several layers of such processing elements may be used, with the processing elements in each layer operating in parallel on the outputs of a prior layer in accordance with a specified transfer function. The resulting output array, or output signal(s), represent some characteristic associated with the input array, or source signals, as modified by the backward propagating error signal(s). Because the input array and adaptive coefficients (weights) change over time, the network is able to adapt and learn. Hence, there is no need to mathematically model the medium and vibration sources in order to calculate the type of drive signal needed to cancel, or otherwise control, the sensed vibration. Rather, all that is required is to train the artificial neural network or neurocomputer, e.g., by constraining the error signal(s) to assume a desired value, such as zero, so that the adaptive coefficients are changed to produce the desired result.

In accordance with another aspect of the invention, the artificial neural network used as the control means of the invention may be realized in software and/or custom hardware configurations. The software configurations may be implemented on standard computers, such as, PC's, or on PC's augmented with special high speed processing elements, or on custom processing hardware that has been designed to achieve ultra-high processing speeds. The custom hardware configurations are generally preferred because they are able to respond sufficiently fast to provide operation of the vibration control system in real time for most mechanical and/or acoustical vibrations of interest. Custom hardware processing systems control high frequency vibrations, e.g., on the order of 20 KHz or more. The software configuration implemented on a standard computer, in contrast, is generally only suitable for controlling very low frequency vibrations, e.g., on the order of 1 Hz or less; whereas the software configuration implemented on a PC augmented with a special high speed processing element, such as is used in the examples discussed below, is generally suitable for controlling low frequency vibrations, e.g., on the order of 200 Hz or less.

Advantageously, the vibration control system of the present invention finds application in numerous fields. In addition to conventional vibration cancellation systems used, e.g., to cancel unwanted mechanical vibrations in machinery, aircraft, or other mechanical devices containing moving parts that may give rise to the unwanted vibrations, the invention may also be used to steady and protect delicate instruments, laser optical systems, cameras, or building structures from potentially damaging vibrations originating external thereto. For example, the invention may be used to cancel or reduce the vibration forces felt within a specified structure, such as a building or missile silo, caused by earthquake or other forces. Further, the invention lends itself nicely to any application where a given vibration needs to be conditioned or linearized, e.g., linearizing nonlinear actuators, or linear actuators operating in a nonlinear medium.

The invention may also be used to "quiet" a desired area, such as a noisy work area for personal comfort; or a conference room or office where confidential discussions are to occur, so that sounds originating within the area either cannot be heard (as when the system of the invention is used to cancel such sounds), or cannot be understood (as when the system is used to obfuscate such sounds) from a location outside or remote from the area. This same general approach may be used to "quiet" objects so that such cannot be heard from a remote location, such as the "hum" of machinery in air or other media.

Further, the invention may be used in a speech interpretation device, e.g., designed to aid the deaf. In such a device, the vibration control system of the invention senses the vibrations associated with spoken speech. These vibrations cause an equivalent electrical signal to be generated, i.e., a "matching" (as opposed to canceling) vibration signal, representative of the various phonetic components of the sensed speech. These phonetic components, in turn, are then combined and interpreted as language alphabet characters and converted to a visual display of the phonetic alphabetic elements. The combination of the displayed phonetic elements thus provides a user of the device with a written interpretation of the speech that has been spoken. Such an interpretation device may be worn, e.g., by a deaf person, with a display of the sensed speech appearing on the inside surface of a pair of specially configured glasses where only the deaf person can see the display or a hand held display device. With such devices, the deaf person is able to discern, with only a second or two of delay, the words that are spoken to him or her. In fact, the position of the speaker may also be discerned to aid the deaf in locating the speaker.

It is thus a feature of the present invention to provide adaptive process control systems that provide adaptive control in real time for a wide variety of applications, such as vibration control.

It is another feature of the invention to provide a vibration control system that cancels or otherwise conditions unwanted vibrations at a specified location or target point in a given medium.

It is an additional feature of the invention to provide such a vibration control system wherein the desired vibration cancellation or conditioning is accomplished by generating at least one offsetting vibration and applying the offsetting vibration to the medium at a location that may be remote from the target point within the medium.

It is a further feature of the invention to provide such a vibration control system that cancels or otherwise conditions the vibrations existing at multiple target points within the medium.

It is yet another feature of the invention to provide a vibration control system that automatically adapts to provide a desired vibration cancellation or conditioning at one or multiple target points within the medium, regardless of whether the target points remain stationary or move within the medium.

It is still an additional feature of the invention to provide vibration control systems having the above-described features that operates in real time.

It is also a feature of the invention to provide a vibration control system having features as above described that does not require mathematical modeling of the medium or applied vibrations, nor the programming and processing of complex algorithms, in order to operate.

BRIEF DESCRIPTION OF THE DRAWINGS

The above and other aspects, features and advantages of the present invention will be more apparent from the following more particular description thereof, presented in conjunction with the following drawings and appendix wherein.

Figure 8:
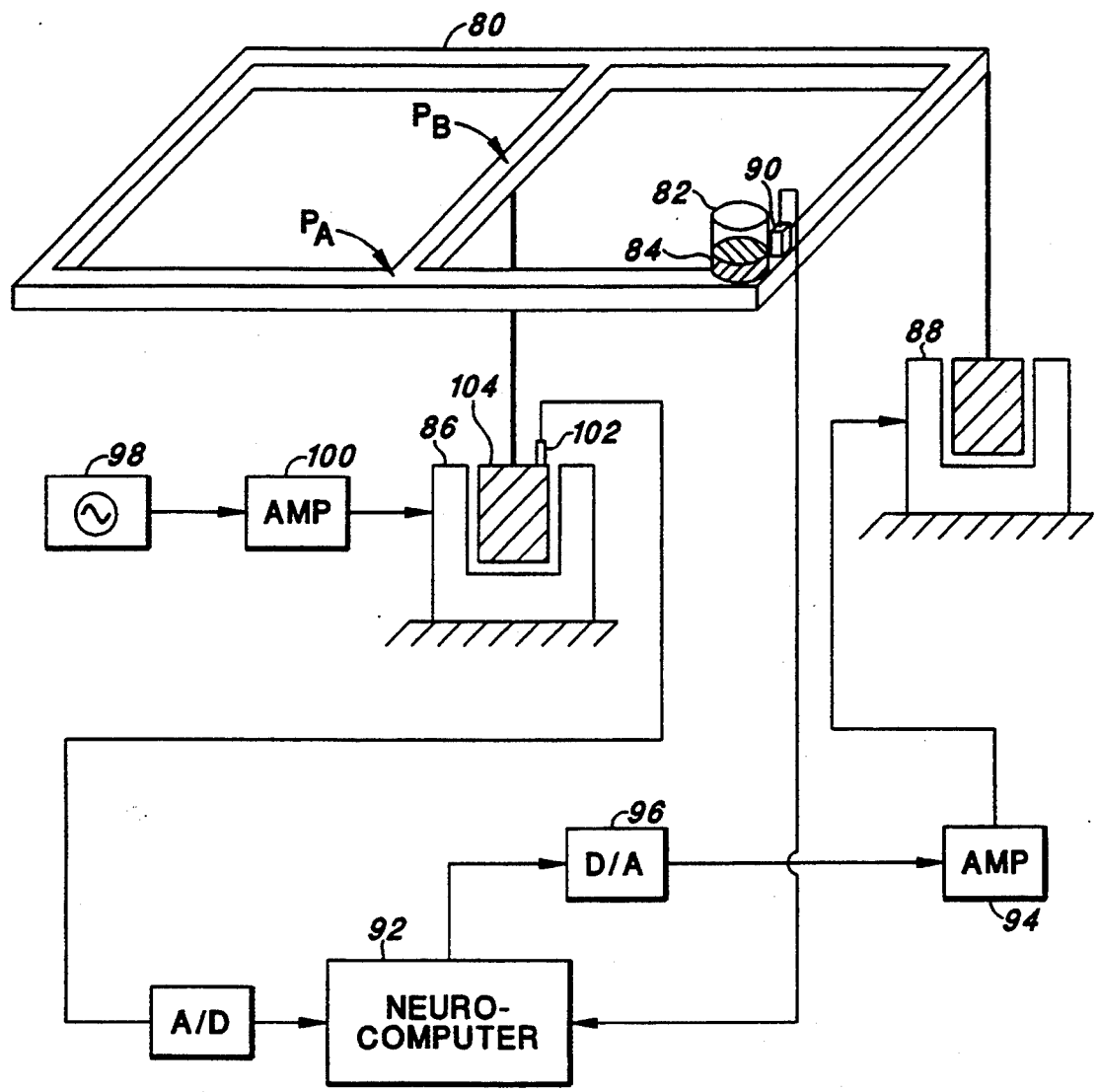
FIG. 8 is a block diagram of a vibration table and associated controls used in conducting Examples 1 and 2, described below.

Appendix A contains the code listing used to program the neurocomputer of FIG. 8 in accordance with a MIMO operating mode of the invention as set forth in Example 2.

DETAILED DESCRIPTION OF THE INVENTION

The following description includes the best mode presently contemplated for carrying out the invention. This description is not to be taken in a limiting sense, but is made merely for the purpose of describing the general principles of the invention. The scope of the invention should be determined with reference to the claims.

Figure 1:
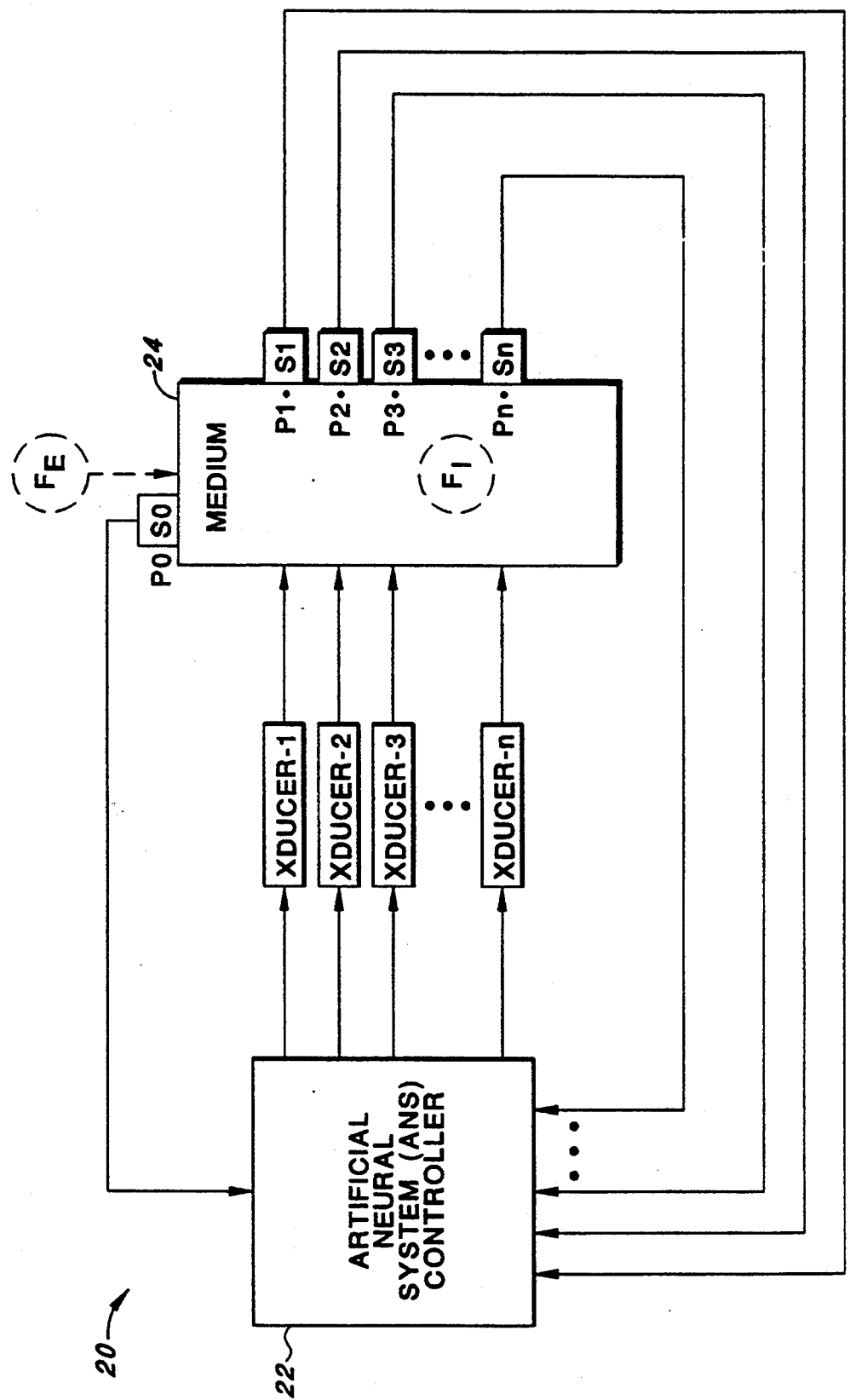
FIG. 1 is a block diagram of a vibration control system made in accordance with the present invention.

Referring first to FIG. 1, there is shown a block diagram of a vibration control system 20 made in accordance with one embodiment of the present invention. The invention includes an artificial neural system (ANS) controller 22 that is coupled to control a plurality of transducers, identified in FIG. 1 as XDUCER-1, XDUCER-2, XDUCER-3, ... XDUCER-N. The transducers, in turn, are each coupled to a given medium 24. The medium 24 is represented in FIG. 1 as a box. This generalized representation emphasizes that the medium may take several forms, either solid or fluid. Typically the medium will be some sort of structure, such as a table or the mechanical housing of a particular item of machinery. However, it is to be emphasized that the medium may take other forms, such as an entire building, a mass of air, or a mass of water.

For most types of mediums with which the present invention is used, the transducers, such as the transducer XDUCER-1, each comprise a device that converts an electrical signal, obtained from the ANS controller 22, to mechanical motion. The mechanical motion is coupled to the medium through conventional means. For example, where the medium is a rigid or semi-rigid structure, the transducer is typically realized using an electromagnetic shaker that is physically coupled to the medium, causing the medium to shake as controlled by the control signal applied to the electromagnetic shaker. Where the medium is a mass of air, the transducer may comprise an audio speaker, or an audio speaker system (comprising a plurality of speakers), that moves a diaphragm in contact with the air in order to transmit acoustic waves through the air.

As further seen in FIG. 1, a plurality of sensors, S0, S1, S2, S3, ... Sn, are also coupled to the medium 24. The number of sensors n need not be the same as the number of transducers N, although it frequently will be. The sensors are selected to detect vibrations that occur at a particular monitoring point within the medium. One sensor, S0, senses the source vibration, e.g., caused by an external force $F_E$ or an internal force $F_I$. The other sensors sense error vibrations at designated points throughout the medium 24. Thus, as shown in FIG. 1, sensor S1 detects vibrations occurring at monitoring point P1, sensor S2 detects vibrations occurring at monitoring point P2, sensor S3 detects vibrations occurring at monitoring point P3, and so on, with sensor Sn detecting vibrations occurring at monitoring point Pn. (The monitoring point may sometimes be referred to herein as the "target point", because it is the desired location, i.e., the target, where the vibrations are to be controlled.) The actual location of the various monitoring points P1, P2, P3, ... Pn is controlled simply by moving the sensors S1, S2, S3, ... Sn to a desired target location.

The sensors S0, S1, S2, S3, ... Sn may be realized, for most types of media 24 with which the vibration control system 20 is used, with any suitable transducer that converts mechanical motion or force to an electrical signal. Numerous types of sensors may be used for this purpose. For example, where the medium comprises a rigid or semi-rigid structure of some type, the sensors S0, S1, S2, S3, ... Sn will typically be realized using a conventional accelerometer. Where the medium comprises a fluid, such as air, the sensors S0, S1, S2, S3, ... Sn will typically be realized using a conventional microphone.

As indicated, the sensors S0, S1, S2, S3, ... Sn generate an electrical signal having a magnitude representative of the vibration that is sensed by each sensor. These signals are connected to the ANS controller 22. The ANS controller 22, as explained more fully below, responds to the detected vibrations by generating a control signal that is applied to each transducer. The control signal drives the transducer so as to cause the vibration sensed by each particular sensor to achieve a desired level.

The embodiment of the invention shown in FIG. 1 is particularly well suited for vibration cancellation. That is, the vibration sensed at point P0 by sensor S0 is connected to the ANS controller 22 as the source or input signal. The vibration sensed at any of the monitoring points P1, P2, P3, ... Pn within the medium 24, which vibration is manifest by the respective output signals of the sensors S1, S2, S3, ... Sn, serves directly as an error signal that is fed back to the ANS controller 22. The ANS controller, in turn, is trained or adapted, as explained below, to control the respective transducers, XDUCER-1, XDUCER-2, XDUCER-3, ... XDUCER-N, so as to drive each of the error signals to zero. Any source vibration that may be present in the medium 24, as excited, e.g., by an external force $F_E$ and/or an internal force $F_I$, is thus sensed at the respective monitoring points, and appropriate offsetting vibrations are immediately generated so as to eliminate, or reduce, the sensed vibration. Advantageously, due to the ability of the ANS controller 22 to automatically adapt itself to reduce the vibrations at the selected error sensing points, the sensors S1, S2, S3, ... Sn can readily be moved within the medium as often as is required or desired, and the system 20 will quickly adapt to reduce or cancel the vibrations at the new monitoring points. (It is noted that the sensor S0 may also be moved within the medium 24, but typically it is positioned close to the source of the input vibration so as to present a true picture of the input vibration.)

Significantly, the vibration control system 20 shown in FIG. 1 is able to simultaneously cancel or reduce vibrations at multiple monitoring points within the medium 24 by simultaneously generating multiple offsetting vibrations that are applied to the medium at various locations. This multiple-input, multiple-output (MIMO) type of vibration control has not heretofore been possible, to applicants' knowledge. This is because of the complexity of the problem involved. That is, the vibration that occurs at each monitoring point, e.g., the point P1 is not only attributable to the source vibration (caused by any external forces $F_E$ or internal forces $F_I$ that may be present in the medium 24), but also includes components of the offsetting vibrations generated by the respective transducers, XDUCER-1, XDUCER-2, XDUCER-3, ... XDUCER-N. The magnitude and phase of the offsetting vibrations generated by each of the controlling transducers must be controlled so that the vibration at each of the monitoring points is zero. As a correction is made at one transducer to reduce the vibration at one monitoring point, the correction is felt at all the other monitoring points as well. Thus, the ANS controller 22 must control all of the transducers so that they all cooperate as a group to reduce the vibrations at each of the selected monitoring points. There is thus a very complex interaction between all of the transducers and all of the monitoring points that is extremely difficult to describe or model using classical mathematical techniques.

A simplified version of the vibration control system shown in FIG. 1 is the case where only one transducer, one source sensor, and one error sensor is used. Such a simplified system provides sufficient vibration control where the vibration is to be controlled only in one location (at the location of the error sensor). However, other applications require vibration control at more than one point simultaneously, in which case the more generalized MIMO vibration control system shown in FIG. 1 must be used.

As is evident from the above generalized description of the invention, a key component of the vibration control system 20 is the ANS controller 22. An Artificial Neural System (ANS) is a system that performs neurocomputing. Neurocomputing involves the use of one or more neural networks—networks patterned after the structure of a human brain—to perform nonalgorithmic information processing. Such processing is an alternative form of information processing that involves the parallel processing of large amounts of small pieces of information (data). Neurocomputing is fast becoming an established discipline. See, e.g., Hecht-Nielsen, Robert, "Neurocomputing: Picking the Human Brain," IEEE Spectrum, pp. 36–41 (March 1988).

There is a great deal of literature currently available describing the operation and use of artificial neural systems, or neurocomputers. See, e.g., Rumelhard, et al., *Parallel Distributed Processing*, Vols. 1 and 2 (MIT Press, Cambridge, MA 1988); *Artificial Neural Networks: Electronic Implementations*, Nelson Morgan, Editor, (IEEE Computer Society Press, 1990); *Artificial Neural Networks: Concept Learning*, Joachim Diederich, Editor (IEEE Computer Society Press, 1990). Thus, no attempt will be made herein, except on a very cursory level, to explain the manner in which an ANS operates. Basically, an ANS is simply one form of a parallel distributed network (PDN) made up of processing elements (PE's) that are interconnected via information channels called interconnects. Where these PE's perform simple nonlinear functions, they may be referred to as "neurons." Each PE or neuron may have multiple inputs, but typically only one output (although this output may be connected to several different locations within the ANS). The PE's are arranged in several different layers. A first or input layer of PE's is generally characterized by each PE having an input that comprises one of the input signals to the PDN. An output layer of PE's is characterized by each PE providing one of the output signals of the PDN. The signal at the output of each PE in the input layer functions as an input signal to the PE's of the next or other layers, either in a feedforward or feedback interconnect. These interconnections may be weighted by an appropriate factor.

For simple PDN applications, two layers of PE's may be sufficient, in which case the PDN comprises only an input layer and an output layer. For more complex applications, one or more hidden layers of PE's may be required between the input and output layers. The complexity of the PDN is largely governed by the number of layers of PE's.

Figure 2:
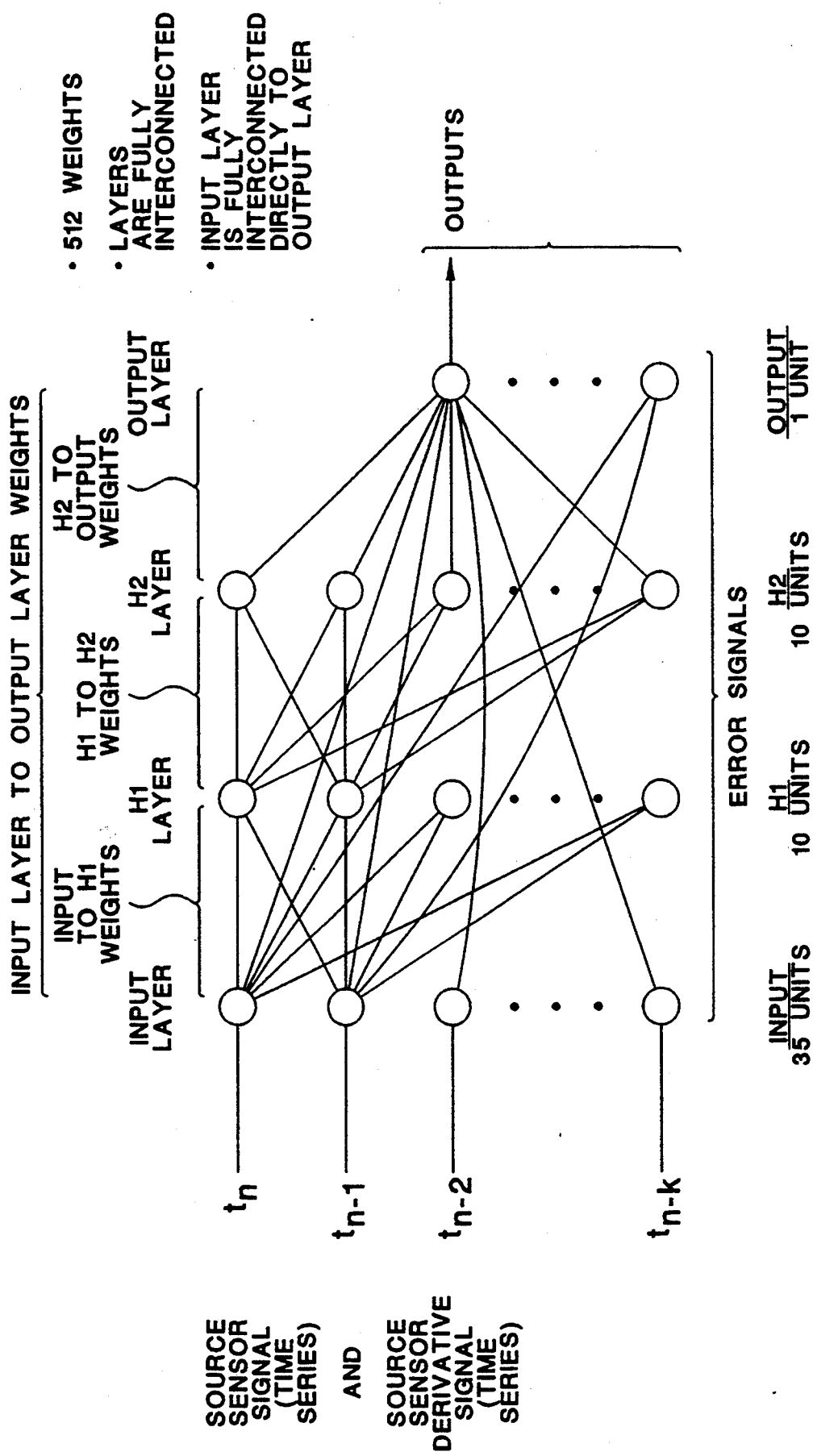
FIG. 2 is a diagram of a 4-layer neural network of the type utilized within the artificial neural system (ANS) of FIG. 1.

The general structure of a four-layer neural network, for example, is illustrated in FIG. 2. This particular four-layer neural network is the preferred network for use in the ANS controller of the present invention, although it is to be emphasized that the number of layers for the neural network of the present invention is not limited to four.

As indicated, one advantage of using an PDN or ANS is that it can adapt or self-adjust the strength of the interconnections between processing elements. Self-adaptation allows an ANS to "learn" and to eventually improve in overall system performance.

Learning results from application of a selected learning rule. Most learning rules comprise variants of the Hebbian learning rule which states that if two units (processing elements) are highly active, the strength of the interconnect between these two units should be strengthened. A variation of this learning rule is the delta rule. According to the delta rule, the amount of learning (i.e., the strength or weight of the interconnect between two processing elements) is proportional to the difference (or delta) between the actual activation achieved and a target activation provided by a teacher. A variation of the delta rule is the generalized delta rule. The generalized delta rule provides a technique for backpropagating the error from the output layer to the hidden layers so that the delta rule can be used for internal weight updates. The delta rule and the generalized delta rule are discussed at length in Chapters 8 and 11 of Rumelhart reference, cited above, and several variations or extensions of the rule exist.

The generalized delta rule, its variations and/or extensions, provide the primary learning rule utilized by the ANS of the present invention. Although other learning rules, known or yet to be developed, could of course be used with the vibration control system of the present invention, use of the generalized delta rule advantageously provides an effective way to accurately teach the ANS how to control a force transducer, so that in cooperation with other force transducers, the vibrations at desired monitoring points within a medium can be effectively controlled. Other neural network algorithms and architectures could also be applied, such as recurrent back propagation, direct weight connection from input to output, and back percolation networks.

Advantageously, the ANS controller 22 shown in FIG. 1 may be realized using a commercially available neurocomputer, such as the Sigma Workstation available from Science Applications International Corporation (SAIC), San Diego, Calif. The Sigma Workstation is a 386 AT-based computer that features SAIC's Delta II floating point processor card as an accelerated processor. The Delta II floating point processor card is also commercially available from SAIC, as is a full set of documentation describing its installation and use in a 386 AT-based computer. An additional description of the Delta II floating point processor card may be found in U.S. Patent application Ser. No. 07/191,207, filed 05/06/88, assigned to SAIC.

As indicated above, FIG. 2 is a diagram of a 4-layer neural network of the type utilized within the ANS controller 22 of FIG. 1. A first input to the network comprises the output signal from the source sensor S0. A second input to the neural network comprises the derivative of the first input. As shown in FIG. 2, the input layer includes nominally 35 units or neurons, each having an input. The sensor output signal is applied to one half of these inputs in a time series. The derivative of the sensor output signal is applied to the other half of these inputs in a time series. That is, the sensor output signal is applied to a suitable shift register, or equivalent, that is nominally seventeen (17) stages long. Thus, at time $t_n$, a first stage of the input signal shift register contains the sensor output signal (or a digital representation of the sensor output signal) at that time. Similarly, a second stage of the shift register contains the sensor output signal at time $t_{n-1}$, one sample time prior to time $t_n$. A third state contains the sensor output signal at time $t_{n-2}$, and so on, with the last stage of the shift register containing the sensor output signal at time $t_{n-k}$. The shift register is thus at least $k+1$ stages long. Each stage of the shift register is connected to a corresponding neuron or "unit" of the first half of the first layer of the neural network. In like manner, the derivative of the sensor output signal is applied to a suitable shift register, each stage of which is connected to a corresponding neuron or "unit" of the second half of the first layer of the neural network.

As further seen in FIG. 2, the preferred neural network also includes two intermediate layers, or "hidden" layers of neurons, identified as H1 and H2. Each of the hidden layers contains nominally ten neurons or units. (It is to be emphasized that the number of neurons in each layer presented herein is only exemplary.) A final or output layer of the network contains at least one neuron or unit. In general, the number of neurons in the output layer will be equal to the number of outputs of the neural network. All of the layers are fully interconnected, including a directly connected layer between the inputs and outputs. (Only some of the interconnections are shown in FIG. 2 for clarity.) That is, each of the 35 neurons in the input layer is connected to all of the neurons in the H1 layer. Similarly, each of the neurons in layer H1 is connected to all of the neurons in the H2 layer. Each of the neurons in layer H2 is connected to each output neuron. Further, each of the neurons in the input layer is directly connected to each output neuron.

The connections between the respective neurons are weighted with adaptive coefficients that determine the strength of the connection. These weights are determined by error signals, which error signals (represented in FIG. 2 as being applied to the bottom of the layers) propagate backwards through the network in accordance with the relation:

$$E_i = \left( \sum_j W_{ij} E_j \right) f'(O_i)$$

where $E_i$ represents the error for the $i^{th}$ neuron in the i layer, $W_{ij}$ represents the weights or adaptive coefficients between neurons in the i and j layers of the network. $O_i$ is the output of the $i^{th}$ neuron, and $f'(O_i)$ is the derivative of the output of the ith neuron.

These weights are updated automatically in accordance with the generalized delta rule described above and referenced in the literature. The backpropagated error determines the change $\Delta W_{ij}$ in the connection strengths according to the relation:

$$\Delta W_{ij} = \eta O_i E_j,$$

where $\eta$ is the predetermined learning rate.

As indicated above, the ANS controller 22 may be implemented using software, using a neurocomputer (such as the SAIC Sigma Processor), or in custom hardware (e.g., in a group of custom LSI or VLSI chips). ("LSI" stands for large scale integration; "VLSI" stands for very large scale integration. Both terms refer to the number of active components, e.g., transistors, that are included on a single silicon or other semiconductor chip used to fabricate an integrated circuit, or IC).

Except for controlling very low frequency vibrations, e.g., less than 1 Hz, a software implementation of an ANS using a conventional computer is not practical. Advantageously, when a neurocomputer is programmed to realize the neural-network configurations described below in connection with FIGS. 3A–3D, excellent vibration control for vibrations up to about 200 Hz may be achieved, as indicated in the two examples described below. This is a sufficiently wide bandwidth for most non-acoustical vibration control applications. For higher vibration frequencies, a custom LSI/VLSI chip-based design that implements the ANS configuration described below in FIG. 3 may be used. Vibration frequencies up to about 20 KHz may advantageously be controlled using such a custom LSI/VLSI design. This is a sufficiently wide bandwidth for all acoustical vibration control applications.

One of the objectives of the present vibration control system is to provide effective vibration control in "real time". This means that there can not be any significant delays between the time when a vibration is first sensed, and when an appropriate corrective signal is applied to control the vibration in a desired fashion. While it is fairly straightforward to reduce delays when the input excitation signal (i.e., the vibration force that excites the unwanted vibrations in the medium) is a periodic force, because the input force can be readily predicted due to its periodic nature, achieving a sufficiently fast response time to react to non-periodic changes occurring in the input excitation signal presents a formidable challenge, even for an adaptive ANS system. Thus, a key component of the vibration control system of the present invention is to configure a collection of neural networks, of the type shown in FIG. 2, in a configuration that provides the requisite response time. One such configuration is shown in the block diagram of FIG. 3A. Others are shown in the block diagrams of FIGS. 3B–3D.

Figure 3A:
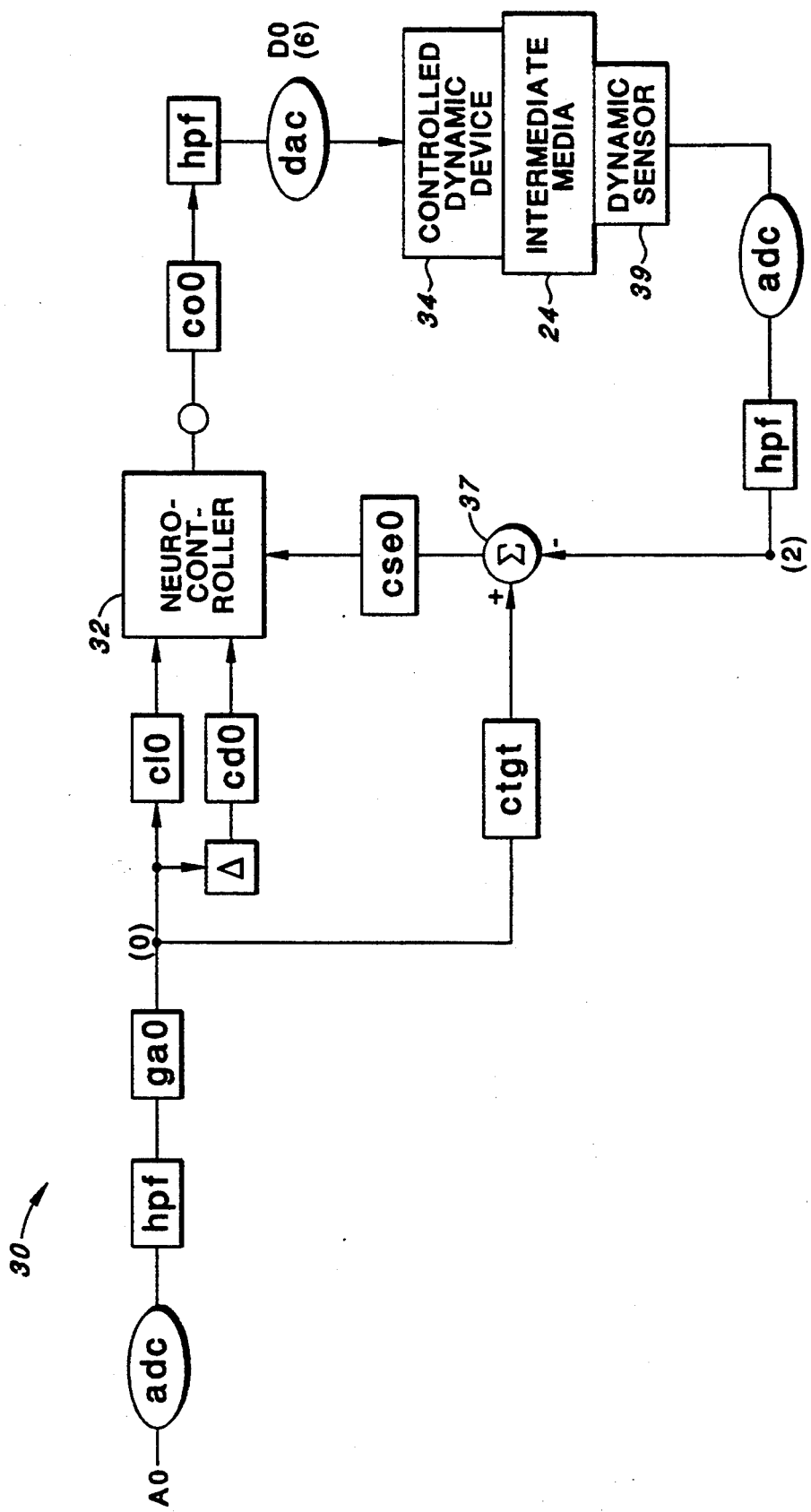
FIGS. 3A, 3B and 3C are block diagrams showing various embodiments of a single-input, single-output neural network control system used, e.g., for the ANS of FIG. 1.

FIG. 3A illustrates a block diagram of an embodiment of a single-input, single-output neuro-system for use, e.g., with the vibration control system 20 (FIG. 1) of the present invention. The neuro-system 30 forms part of the ANS controller 22 (FIG. 1), and is used for the simplified situation where only one transducer, e.g. XDUCER-1, is used to impart an offsetting vibration to the medium 24, and where only one sensor, e.g., S1 is used to sense vibrations at a given location, e.g. point $P_1$, within the medium 24. The neuro-system 30 shown in FIG. 3A is patterned after an LMS algorithm utilized in classical adaptive signal processing design. See, e.g., Widrow and Stearns, Adaptive Signal Processing, ("Adaptive Control Systems"), (Prentice-Hall, 1985). However, there are some significant differences between a classical adaptive control system, and the configuration shown in FIG. 3A, principally relating to the manner in which the various elements of the neuro-system are realized using non-linear neural network architectures instead of linear LMS architectures.

As seen in FIG. 3A, the single-input, single-output neuro-system 30 comprises a neuro-controller 32 that is coupled to control a "controlled dynamic device" 34. The neuro-controller 32 is realized using a neural network of the type described above in connection with FIG. 2. The input signal to the neuro-controller 32 is a signal obtained from a suitable source sensor, e.g., the sensor SO (FIG. 1). This input signal is identified at the far left of FIG. 3A as the signal A0. This input signal A0 is converted from analog to digital format using an "adc" (analog-to-digital converter) and time delayed as required in order to provide an input signal to each input of the first neuro-controller 32 (i.e., to each input of the first layer of the neural network that comprises the neuro-controller 32). This time delay is achieved by using the input layer as a shift register giving the network a time history of the input values. Further, the input signal may be differentiated and time shifted using a suitable differentiator represented in FIG. 3A by the "Δ" circuit, and input shift register. The error signal is applied to the neuro-controller 32. The error signal back-propagates through the neural network that makes up the neuro-controller 32 to set the value of the "weights" used therein, which error signal is obtained either from the sensor 39 for cancellation operations or from the summing point 37 for linearization operations as described below.

The controlled dynamic device 34 comprises a suitable transducer for converting an output signal from the neuro-controller 32 to linear mechanical motion. The transducer device 34 may be, e.g., an electromagnetic shaker. The transducer device 34 is coupled to an intermediate medium 24'. A dynamic sensor 39 is also coupled to the medium 24'.

Figure 3B:
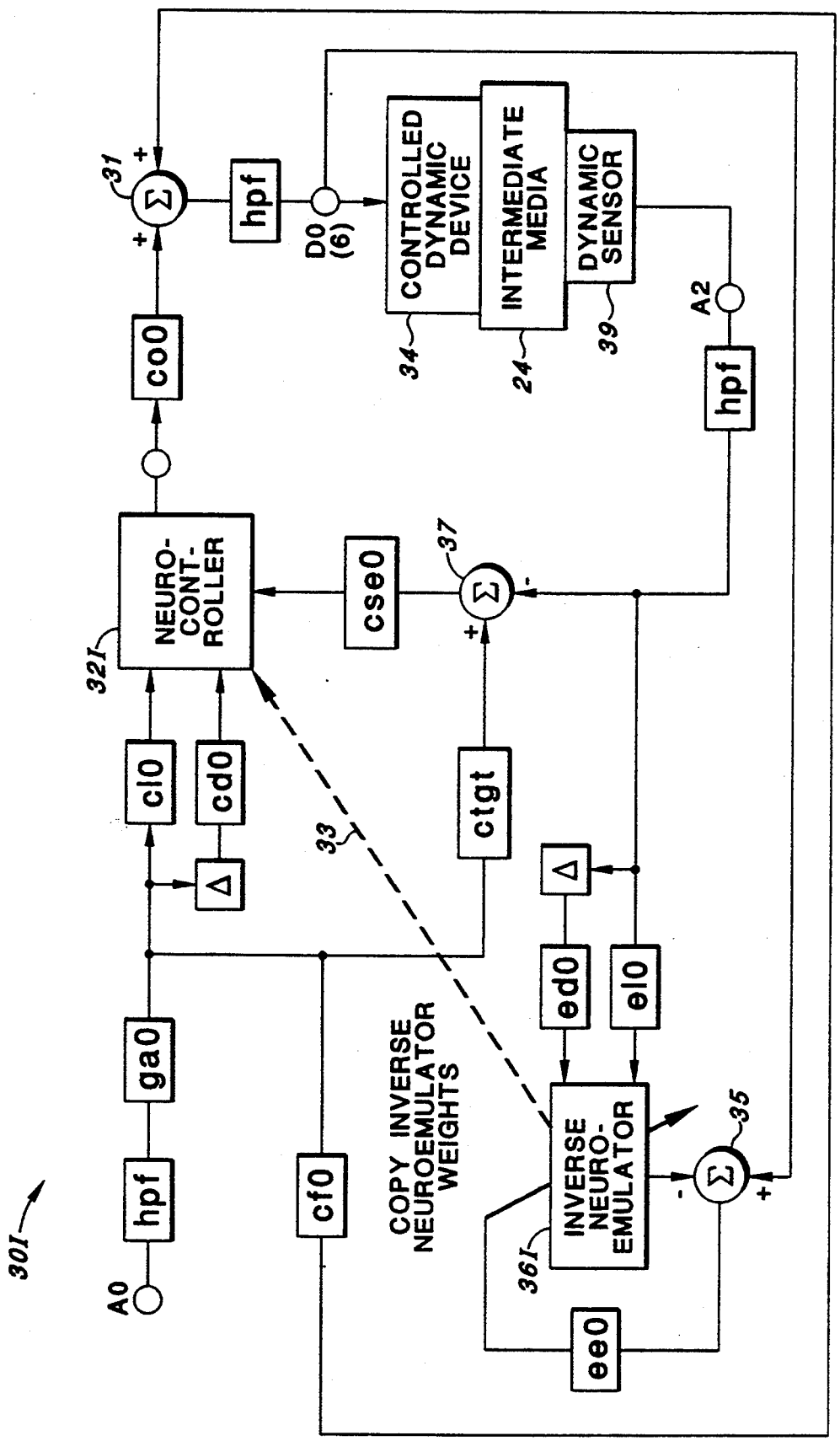

FIG. 3B illustrates a block diagram of another embodiment of a single-input, single-output neural-system 30I for use, e.g., with the vibration control system 20 (FIG. 1) of the present invention. the neural-system 30I is similar to neural system 30 (FIG. 3A) with the addition of an inverse neuro-emulator 36I which is connected in parallel with the transducer 34, medium 24;

and dynamic sensor 39. It is the function of the inverse emulator to learn to emulate the inverse response of the medium to outputs from the neuro-controller 32I. The input signal is obtained from the dynamic sensor 39 output to the inverse neuro-emulator. The input signal and its derivative are time shifted, as required, using shift registers as above described, in order to provide an input to each input of the inverse neuro-emulator circuit 36I. The output of the inverse emulator 36I is compared with the input to the device 34 at a summation point 35 in order to develop an inverse emulator error signal, identified as "ee0". This inverse emulator error signal is fed back to the inverse emulator 36I in order to back-propagate through the layers of the inverse emulator 36I and change the weights as required in order to force the inverse emulator error signal to zero. When the inverse emulator error signal is zero, the inverse neuro-emulator 36I thus represents an exact imitation of the inverse transfer function of the coupled transducer 34 and medium 24.

The "weights" used in the neuro-controller 32I are obtained from the inverse neuro-emulator 36I. This weight transfer is represented in FIG. 3B by a dotted line 33.

As seen in FIG. 3B, the error signal used to set the values of the weights used in the neuro-controller 32I is an error signal, identified by the gain block control "cse0", that may be obtained from one of two sources. When the neural-system 30I is operating in a linearization mode, the error signal "cse0" comprises the difference between the signal sensed by the sensor 39 and the input signal A0. This difference signal is generated at summing node 37. When the neural-system 30I is operating in a cancellation mode, the gain control "ctgt" is set to zero, thereby causing the error signal "cse0" to simply be the signal sensed by the sensor 39. That is, in a cancellation mode, any vibrations sensed at the sensor point represent undesired vibrations, and thus the sensor signal itself provides the error signal.

Thus, it is seen that the neural system 30I embodiment shown in FIG. 3B, discussed above, is a refinement of the neural system 30 (FIG. 3A).

In all of FIGS. 3A–3D, it is noted that the blocks marked "hpf" refer to a "high pass filter." The ovals marked "adc" refer to an analog-to-digital converter; and the ovals marked "dac" refer to a digital-to-analog converter. In some figures, e.g., FIGS. 3C and 3D, the adc's and dac's have been omitted for clarity. The other small blocks in the figures refer to gain blocks, i.e., multiplication factors used to adjust the magnitude of the various signals.

Figure 3C:
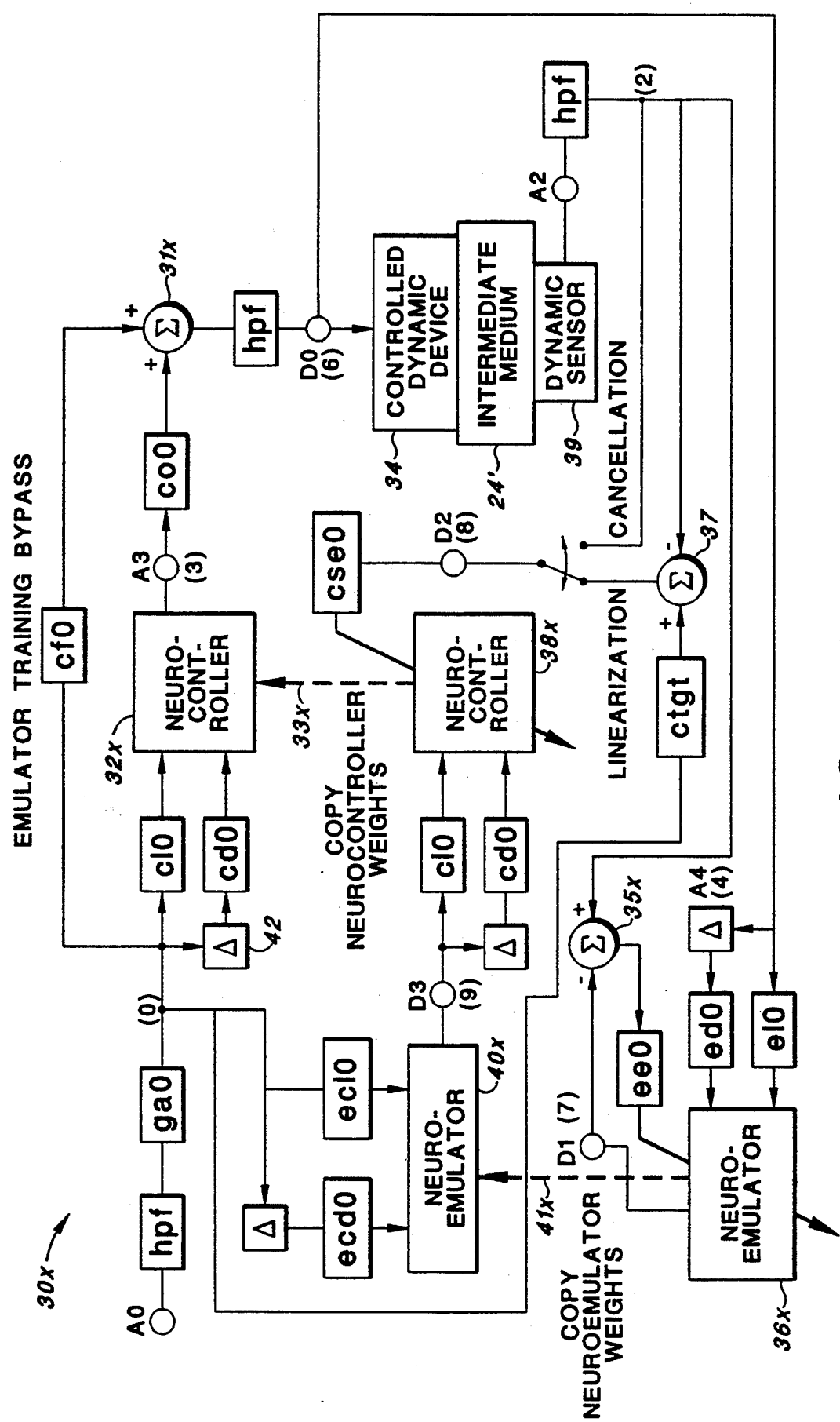

FIG. 3C illustrates a block diagram of a preferred single-input, single-output neuro-system 30x for use, e.g., with the vibration control system 20 (FIG. 1) of the present invention. The neuro-system 30x forms part of the ANS controller 22 (FIG. 1), and is also used for the simplified situation where only one transducer, e.g. XDUCER-1, is used to impart an offsetting vibration to the medium 24, and where only one sensor, e.g., S1 is used to sense vibrations at a given location, e.g. point P1, within the medium 24. The neuro-system 30 shown in FIG. 3C is patterned after a "filtered-X" LMS algorithm utilized in classical adaptive signal processing design. See, e.g., Widrow and Stearns, supra, Chap. 11 ("Adaptive Control Systems"), pp. 285–297. However, there are some significant differences between a classical "filtered-X" adaptive control system, and the configuration shown in FIG. 3C. These differences relate mainly to the manner in which the various elements of the neuro-system are realized using pairs of non-linear neural network architectures instead of linear LMS architectures.

As shown in FIG. 3C, the single-input, single-output neuro-system 30x includes a first neuro-controller 32x that is coupled to control a "controlled dynamic device" 34. The first neuro-controller 32x is realized using a neural network of the type described above in connection with FIG. 2. The input signal to the first neuro-controller 32x is a signal obtained from a suitable source sensor, e.g., the sensor S0 (FIG. 1). This input signal is identified at the far left of FIG. 3C as the signal A0. The sensor outputs are typically analog values that are digitized at an appropriate sample rate for input to the digital network. The derivative, or first difference, of the input signal A0 is calculated, as represented by the "$\Delta$" box 92. Both signals are then shifted into the input layer of the network which is arranged as a shift register to give the network a time history of the input values. An error signal "cse0" is applied to a second neuro-controller 38x, as explained below. This error signal backpropagates through the neural network that makes up the neuro-controller 38x to set the value of the "weights" used therein.

As with the embodiments in FIGS. 3A and 3B, the controlled dynamic device 34 comprises a suitable transducer for converting an output signal from the first neuro-controller 32x to mechanical motion. The transducer device 34 may be, e.g., an electromagnetic shaker. The transducer device 34 is coupled to an intermediate medium 24'. A dynamic sensor 39 is also coupled to the medium 24'.

Connected in parallel with the transducer device 34 is a first neuro-emulator 36x. It is the function of the emulator 36x to emulate or imitate the response of the coupled device (transducer) 34 and medium 24'. When performing this function, the input signal to the first neuro-emulator 36x is the input signal A0 to the system 30, obtained via an "emulator training bypass" route around the neuro-controller 32. The first difference of the input signal is formed, and both signals are then shifted into the input shift register of the first neuro-emulator circuit 36x. The output of the emolator 36x is compared with the output of the device 34 at a summing point 35x in order to develop an emulator error signal. This error signal may be multiplied, as desired, by a gain factor identified as "ee0". This emulator error signal is fed back to the emulator 36x in order to back propogate through the layers of the neuro-emulator 36x and change the weights thereof as required in order to force the emulator error signal to zero. When the emulator error signal is zero, the first neuro-emolator 36x thus represents an exact imitation of the coupled device 34 and the response of the medium 24'.

As indicated above, the "weights" used in the first neuro-controller 32x are obtained from a second neuro-controller 38x. This "weight" transfer is represented in FIG. 3 by a dotted line 33x. That is, by copying the neuro-controller weights (or "adaptive coefficients) from the second neuro-controller 38x to the first neuro-controller 32x, the second neuro-controller 38x actually controls the first neuro-controller 32x. The second neuro-controller 38x receives its inputs from a second neuro-emulator 40x (i.e., the input signal to the second neuro-controller 38x is the output signal from the second neuro-emulator 40x, differentiated and time shifted as required to fill all the inputs to the second neuro-controller 38x).

As seen in FIG. 3C, the error signal used to set the values of the weights used in the neuro-controller 38x is an error signal, identified by the gain block control "cse0", that may be obtained from one of two sources. When the neural-system 30x is operating in a linearization mode, the error signal "cse0" comprises the difference between the signal sensed by the sensor 39 and the input signal A0. This difference signal is generated at summing node 37. When the neural-system 30x is operating in a cancellation mode, the error signal "cse0" simply comprises the signal sensed by the sensor 39. That is, in a cancellation mode, any vibrations sensed at the sensor point represent undesired vibrations, and thus the sensor signal itself provides the error signal.

It is the function of the second neuro-emulator 40x to condition the input signal to the second neuro-controller 38x. The second neuro-emulator 40x uses the input signal A0, as its input signal, differentiated and time shifted as required in order to fill all the inputs to the first layer of the neuro-controller 40x. The "weights" of the second neuro-emulator 40x are copied form the first neuro-emulator 36x. This copying is represented by the dotted line 41.

In accordance with the present invention, the first neuro-emulator 36x and the second neuro-emulator 40X are each realized with a neural network of the type shown in FIG. 2. These two neural networks operate as a pair, with the emulator 36x serving as a "trainer" neural network, and the emulator 40x serving as the "executer" neural network. As soon as the "trainer" network 36x is trained, its weights are transferred to the "executer" network 40x. Advantageously, at substantially the same time that the "training" network 36x is training, the "executer" network 40x is executing based on the most recent weights transferred thereto from the training network. In this way, the neuro-system 30x is able to adapt very quickly to any changes that may occur in the input signal A0.

Similarly, the first neuro-controller 32x and the second neuro-controller 38x may each be realized with a neural network of the type shown in FIG. 2. These two neural networks also operate as a pair, with the controller 38x functioning as a "trainer" neural network, and the controller 32x functioning as an "executer" neural network. Once trained, the weights associated with the controller 38x are transferred to the controller 32x. Advantageously, as with the emulator pair of neural networks described above, at substantially the same time that the controller 38x is being trained, the controller 32x is executing control of the transducer device 34 based on the most recent weights transferred thereto from the controller 38x.

FIGS. 4A–4E illustrate representative transfer functions, showing both amplitude and phase, between selected points of the neuro-control system 30x of FIG. 3C.

Figure 4A:
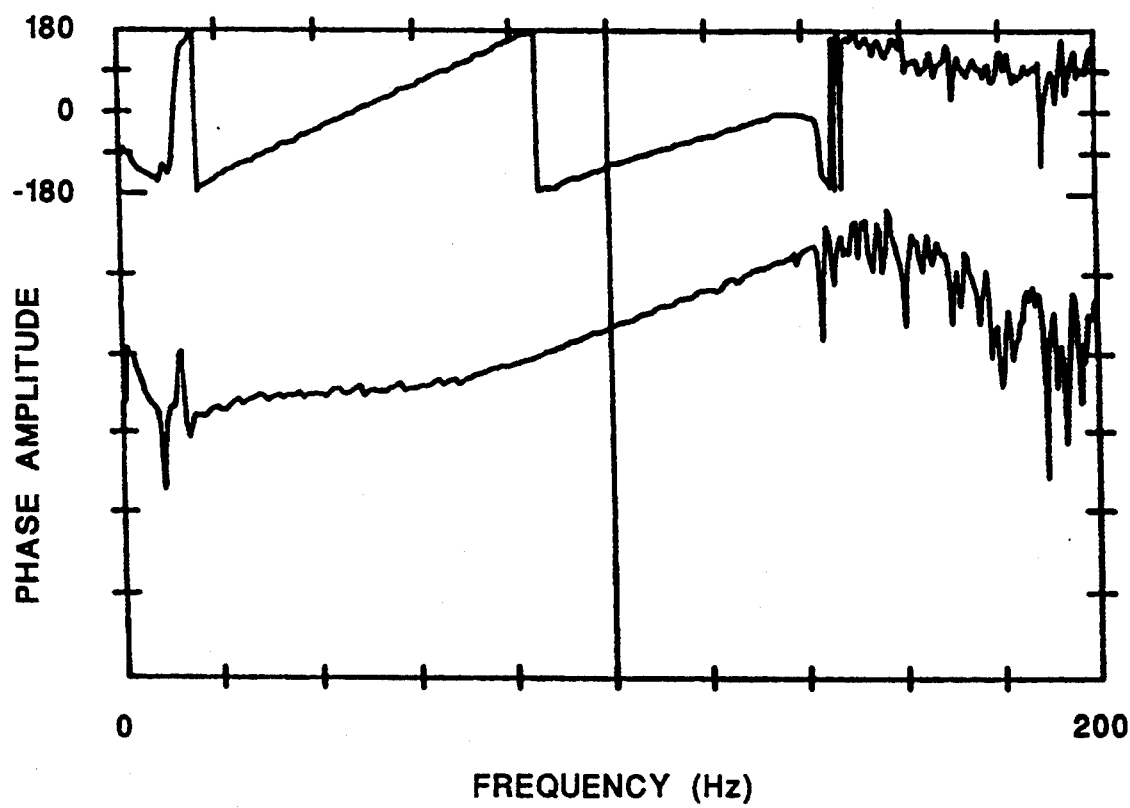
FIGS. 4A, 4B, 4C, 4D and 4E illustrate representative transfer functions, both amplitude and phase, between selected points of the neural network control system of FIG. 3C.

For example, as seen in FIG. 4A, the transfer function between points (0) and (6) of FIG. 3C is depicted. This is basically the transfer function of the controller 32x. Note the wide variations in both phase and amplitude as the frequency of the input signal is swept from 10 Hz to 140 Hz.

Figure 3D:
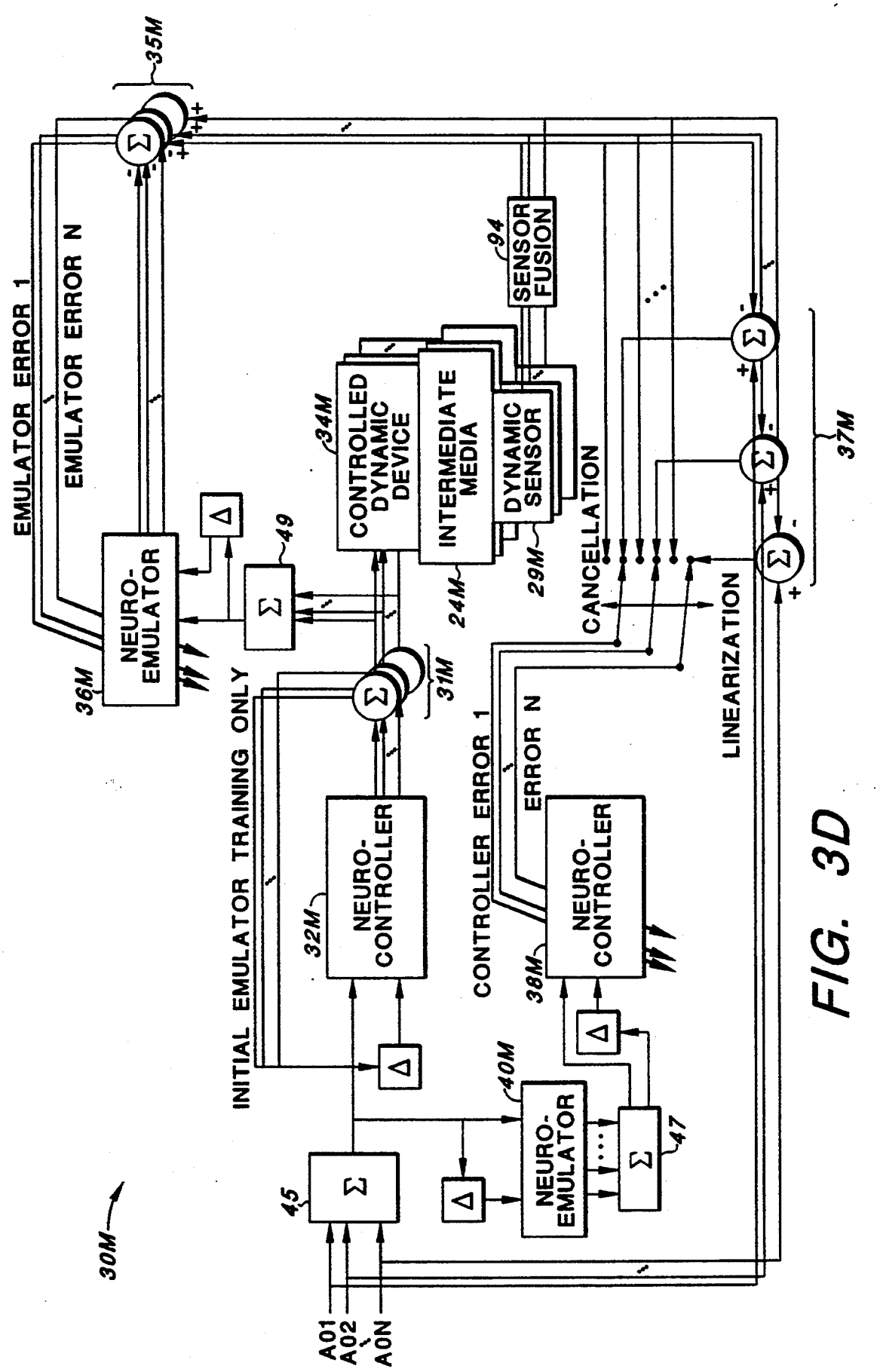
FIG. 3D is a block diagram showing the preferred manner of implementing a multiple-input, multiple-output (MIMO) neural network control system used for the ANS of FIG. 1.
Figure 4B:
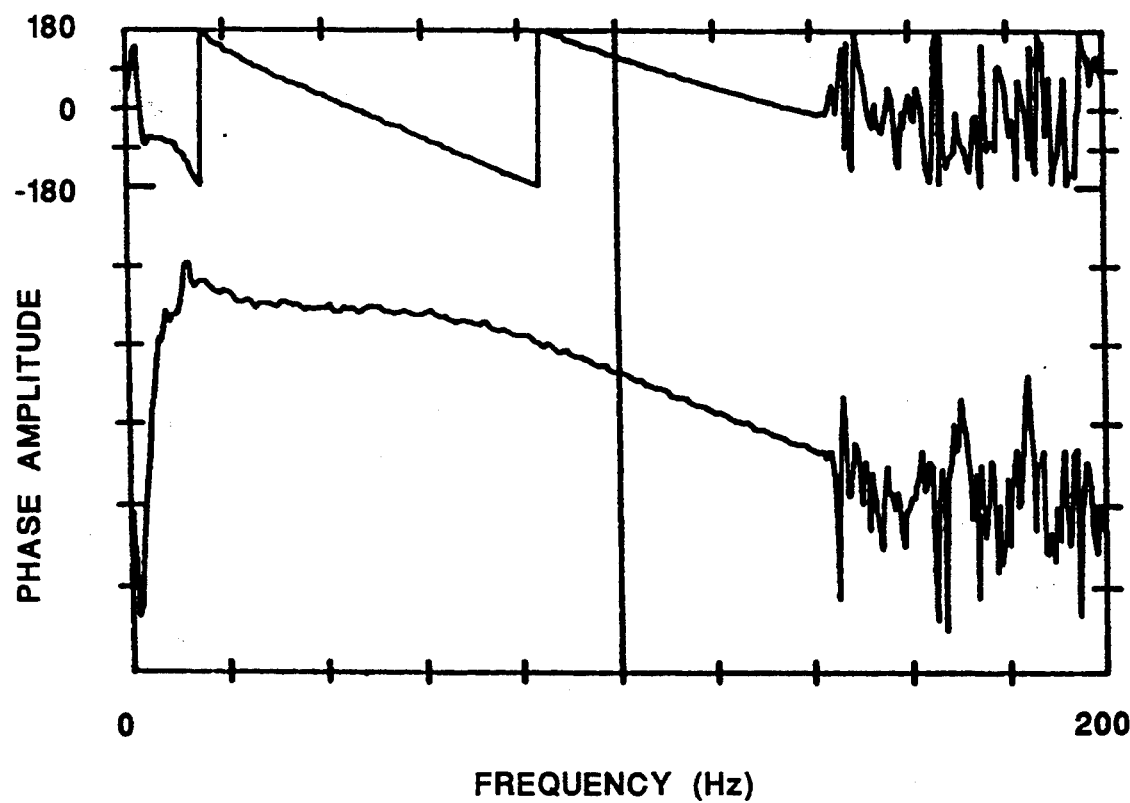

FIG. 4B shows the transfer function between points (6) and (2) of FIG. 3. This is basically the transfer function of the coupled device 34 and medium 24'. Like FIG. 4A, there are wide variations in both phase and amplitude as the frequency is swept between 10–140 Hz.

Figure 4C:
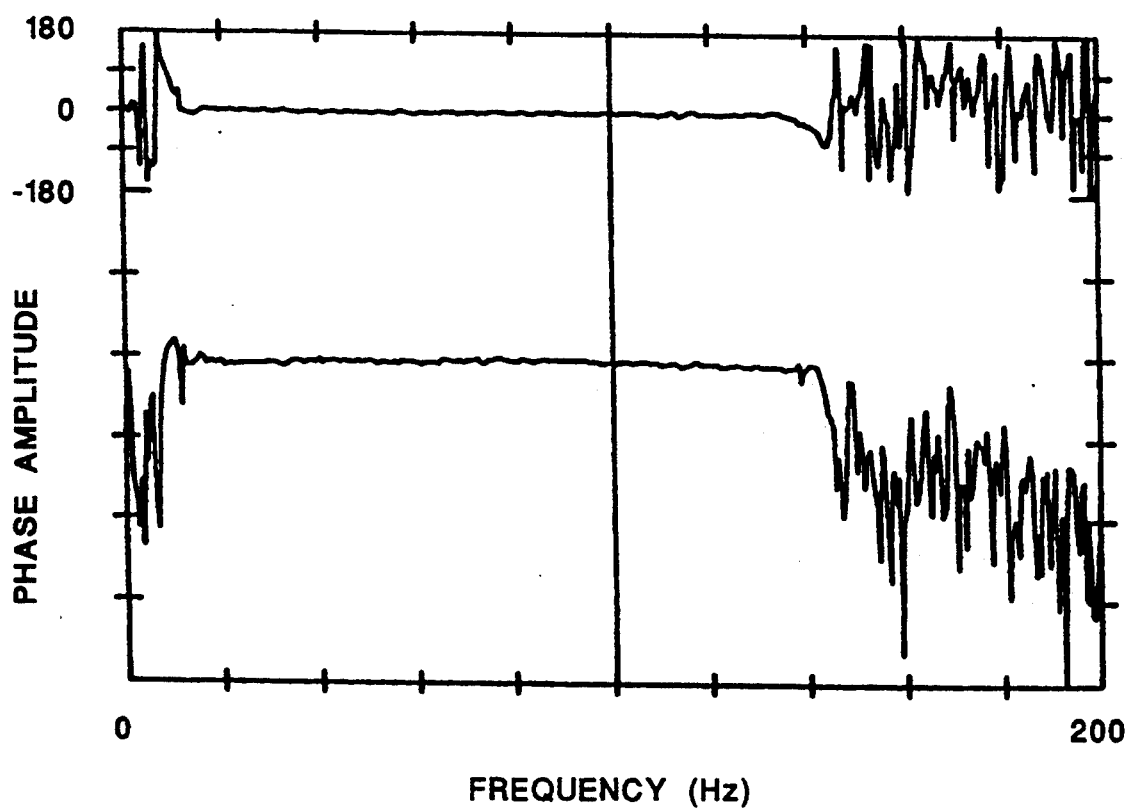

However, note that the variations in phase and amplitude shown in FIG. 4B between 10–140 Hz are substantially equal and opposite to those shown in FIG. 4A. Thus, when the overall transfer function is made, between points (0) and (2), as shown in FIG. 4C, it is seen that, under the conditions shown, the output is able to track the input with very little delay or distortion.

Figure 4D:
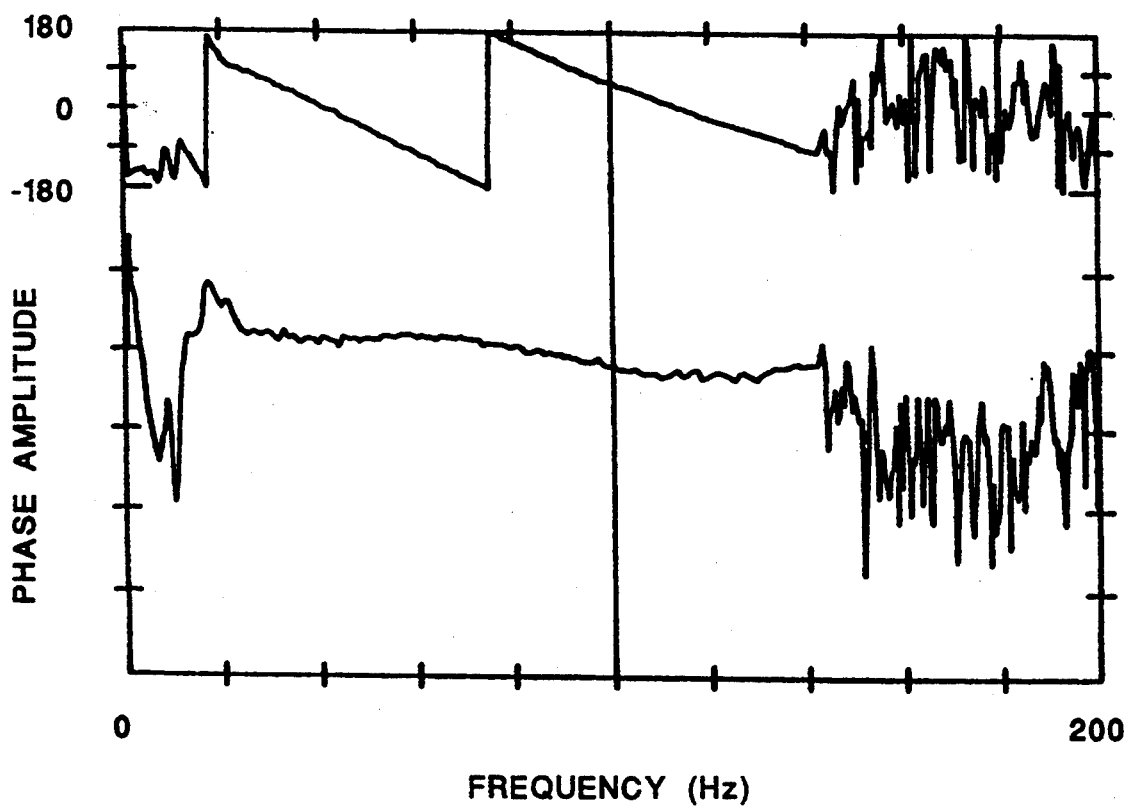
Figure 4E:
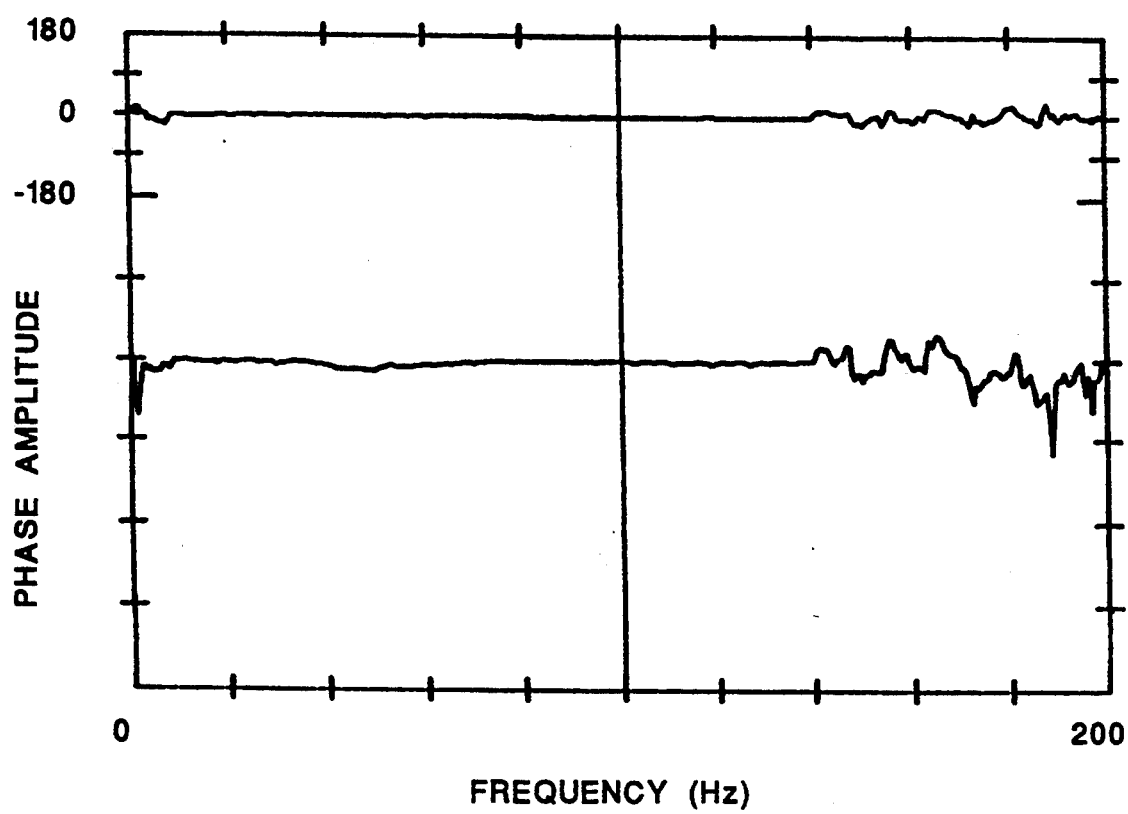

FIG. 4D shows the transfer function from points (0) to (9), and thus shows how well the emulator, 40x is able to follow or imitate the coupled device 34 and medium 24' during the training of neurocontroller 38x. The transfer function in FIG. 4E compares the output of the emulator 36x with the output of the coupled device 34 and medium 24' as sensed by sensor 39 and shows how well the emulator 36x is able to follow or imitate the coupled device 34 and medium 24' in the frequency bakd from 10–140 Hz..

Referring next to FIG. 3D, a block diagram is shown of the preferred manner of realizing a multiple-input, multiple-output (MIMO) neuro-system 30M for use, e.g., with the vibration control system 20 (FIG. 1) of the present invention. The neuro-system 30M forms part of the ANS controller 22 (FIG. 1), and is used for the general situation where multiple transducers, e.g. XDUCER-1, XDUCER-2, XDUCER-3, .... XDUCER-N, are used to impart respective offsetting vibrations to the medium 24, and where only multiple sensors, e.g., S1, S2, S3, ... Sn are used to sense vibrations at respective locations, e.g. points $P_1$, $P_2$, $P_3$, $P_n$ within the medium 24.

For most purposes, the block diagram of FIG. 3D parallels the block diagram of FIG. 3C, and includes the same or equivalent elements as are shown in FIG. 3C, except that the gain blocks, e.g., ee0, cse0, etc., are omitted for clarity. (It is noted that the same reference characters are used in FIGS. 3A–3D to identify the same or equivalent elements, except that different suffixes are used for different embodiments. In FIG. 3A, no suffix is used. In FIG. 3B, the suffix "I" is used. In FIG. 3C, the suffix "X" is used, and in FIG. 3D, the suffix "M" is used ) The suffix "M" for example, signifies that although the element shown in FIG. 3D performs the same function as a corresponding element in FIGS. 3A–3C, the element itself has been modified in order to accommodate multiple inputs and/or outputs. Thus, as shown in FIG. 3D, a first neuro-controller 32M is coupled to control a plurality of "controlled dynamic devices" 34M. (These controlled dynamic devices comprise the plurality of transducers described above in connection with FIG. 1, i.e., XDUCER-1, XDUCER-2, XDUCER-3, ... XDUCER-N.) The first neuro-controller 32M is realized using a neural network of the type described above in connection with FIG. 2, except that it has multiple outputs. Such multiple outputs are readily realized using a neural network of the type shown in FIG. 2 by simply including additional neurons in the output layer.

The input signal to the first neuro-controller 32M is a signal obtained by summing the signals obtained from multiple inputs, identified as A01, A02, ... AON. A summing network 45 performs this summing function. This summed input signal is differentiated and time delayed as required in order to provide input signals to each input of the first neuro-controller 32M (i.e., to each input of the first layer of the neural network that comprises the neuro-controller 32M). The sensor outputs are typically analog values that are digitized at an appropriate sample rate for input to the digital network. The derivative, or first difference, of the input signal A0 is calculated, as represented by the "Δ" box. Both signals are then shifted into the input layer of the network which is arranged as a shift register to give the network a time history of the input values. The error signal applied to the first neuro-controller 32M, i.e., the error signal that back-propagates through the neural network to set the values of the "weights" used therein, is obtained from a second neuro-controller 38M.

Connected in parallel with the transducer devices 34M is a first neuro-emulator 36M. It is the function of the emulator 36M to emulate or imitate the coupled devices 34M and media 24'. Each medium 24M may represent a hybrid medium, e.g., solid or fluid or hybrid combinations. When initially performing this function, the input signal to the first neuro-emulator 36M is the summed input signals A01, A02, . . . A0N obtained via an "initial emulator training only" route around the neuro-controller 32M. Subsequent to initial training, the multiple outputs from the neuro-controller 32M are summed, at summer 49, as required to provide this input signal. This input signal is differentiated and time shifted, as required, using a shift circuit as above described, in order to provide inputs to each input of the first neuro-emulator circuit 36M. The neuro-emulator 36M includes multiple outputs. Each of these outputs are compared with respective outputs from the sensor devices 39M at summing point 35M in order to develop a set of emulator error signals, identified as "Emulator Error 1", . . . "Emulator Error N". This set of emulator error signals is fed back to the emulator 36M in order to back propagate through the layers of the neuro-emulator 36M and change the weights thereof as required in order to force each of the emulator error signals to zero. When each of the emulator error signals is zero, the first neuro-emulator 36M thus represents an exact imitation of what the coupled devices 34M and media 24' must be if the error signals are to be zero, i.e., if the vibrations sensed by the dynamic sensors 39M are at a desired level.

As with the single-input, single-output control system shown in FIG. 3C, the "weights" used in the first neuro-controller 32M of the MIMO control system 30M shown in FIG. 3D are obtained from a second neuro-controller 38M. By copying the neuro-controller weights (or adaptive coefficients) from the second neuro-controller 38M to the first neuro-controller 32M, the second neuro-controller 38M actually controls the first neuro-controller 32M. The second neuro-controller 38M receives its inputs from a second neuro-emulator 40M (i.e., the input signals to the second neuro-controller 38M are the summed output signal and its derivative from the second neuro-emulator 40M, time shifted as required to fill all the inputs to the second neuro-controller 38M).

As seen in FIG. 3D, the error signals used to set the values of the weights used in the second neuro-controller 38M are a set of error signals, identified as "Controller Error 1, . . . Controller Error N", that may be obtained from one of two sources. When the neuro-system 30M is operating in a linearization mode, the set of controller error signals comprises the difference between the set of signals sensed by the sensors 39M and the set of input signals A01, A01, ... A0N. This set of difference signals is generated at summing nodes 37M. When the neuro-system 30M is operating in a cancellation mode, the set of controller error signals simply comprises the set of signals sensed by the sensors 39M.

It is noted that the number of sensors 39M need not be the same as the number of input signals or the number of transducers 34M. If the number of sensors 39M is not the same as the number of input signals, then a "sensor fusion" circuit (i.e., a summation circuit) is used as required to combine selected sensor and/or input signals so that an appropriate difference signal can be generated.

It is the function of the second neuro-emulator 40M to condition the second neuro-controller 38M. The second neuro-emulator 40M uses the summed set of input signals, from summer 45, as ont of its input signals, and the differential of this input signal as another input signal. Both of these input signals are time shifted, as required, in order to fill all the inputs to the first layer of the neuro-controller 38M. The "weights" of the second neuro-emulator 40M are copied from the first neuro-emulator 36M.

As with the single-input, single-output embodiment shown in FIG. 3C, the first neuro-emulator 36M and the second neuro-emulator 40M in the MIMO embodiment of FIG. 3D are each realized with a neural network of the type shown in FIG. 2, modified to include multiple neurons in the output layer. These two neural networks operate as a pair, with the emulator 36M serving as a "trainer" emulator neural network, and the emulator 40M serving as the "executer" emulator neural network. As soon as the "trainer" network 36M is trained, its weights are transferred to the "executer" network 40M. Advantageously, at substantially the same time that the "training" network 36M is training, the "executer" network 40M is executing based on the most recent weights transferred thereto from the training network. In this way, the control system 30M is able to adapt very quickly to any changes that may occur in the set of input signals A01, A02, . . . A0N.

Similarly, the first neuro-controller 32M and the second neuro-controller 38M may each be realized with a neural network of the type shown in FIG. 2, modified to include multiple outputs. These two neural networks also operate as a pair, with the controller 38M functioning as a "trainer" neural network, and the controller 32M functioning as an "executer" neural network. Once trained, the weights associated with the controller 38M are transferred to the controller 32M. Advantageously, as with the emulator pair of neural networks described above, at substantially the same time that the controller 38M is being trained, the controller 32M is executing control of the transducer device 34M based on the most recent weights transferred thereto from the controller 38M.

Figure 5:
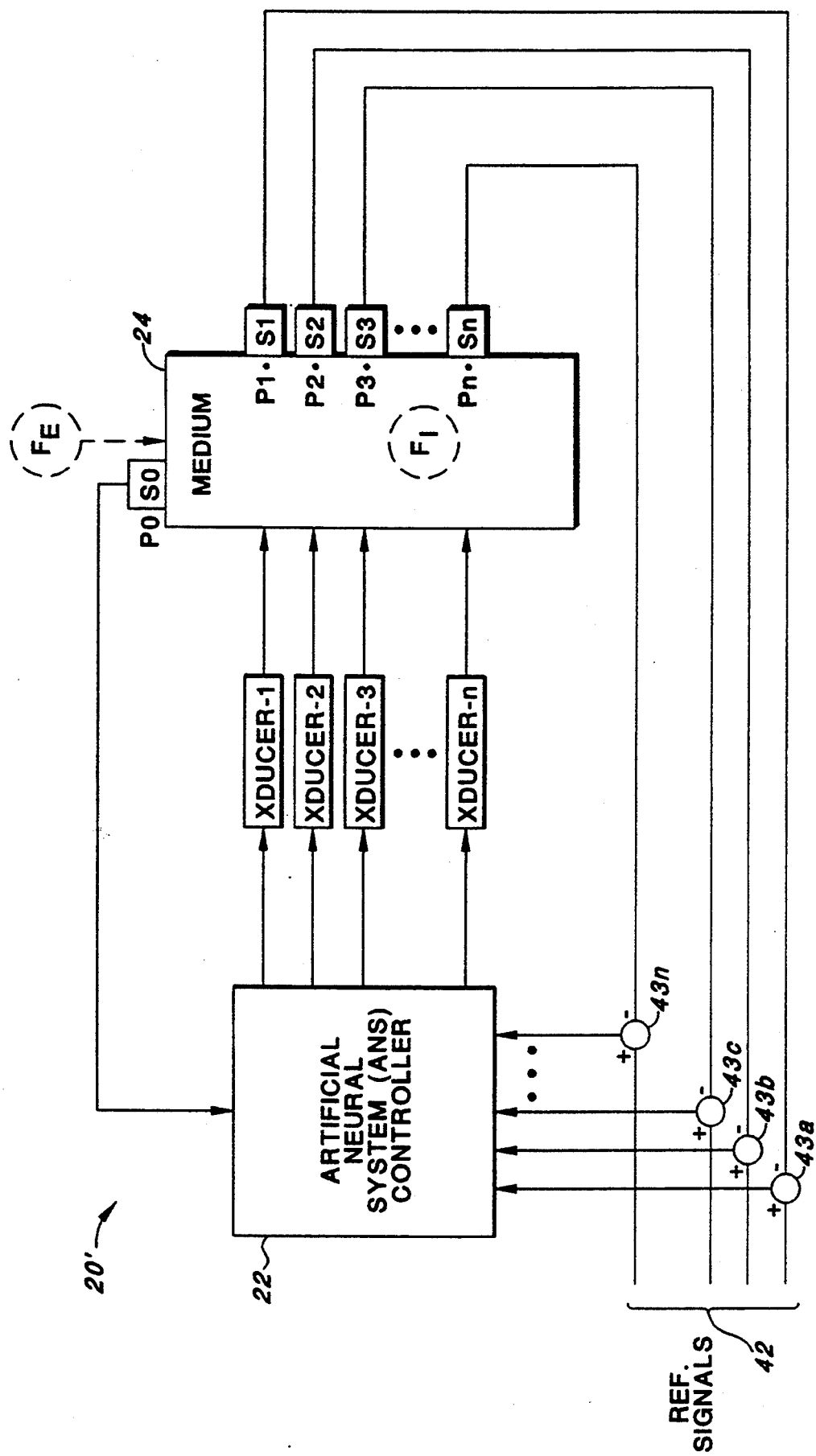
FIG. 5 shows a block diagram of another embodiment of a vibration control system in accordance with the present invention.

Referring next to FIG. 5, a block diagram is shown of an alternative embodiment 20' of a vibration control system in accordance with the present invention. This block diagram is the same as that shown in FIG. 1 (and hence the same reference numerals are used to identify like parts) except that the sensor output signals obtained from the sensors S1, S2, S3, . . . Sn, are compared with appropriate reference signals 42 at summing nodes 43a, 43b, 43c, . . . 43n prior to being returned to the ANS controller 22. Thus, the signals returned to the ANS controller 22 comprise error signals representing the difference between the sensed output vibration, and a desired reference vibration. The ANS controller responds to these error signals so as to drive this error signal to zero. Thus, the output vibrations sensed at the various monitoring points are forced to the reference values. If the reference values are zero, then the system 20' of FIG. 5 operates as a vibration cancellation system the same as the system 20 of FIG. 1. If the reference values are not zero, however, then the system 20' operates to control the vibrations and force them to a desired value. For example, a reference signal may take the form of a sine wave or triangular wave, in which case the ANS controller 22 forces the medium 24 to vibrate in such a way that each monitored point also assumes the desired sine or triangular wave. Such a situation may be desirable, e.g., in a shake table, where particular points in the medium (the structure under test) are to be subjected to specified types of vibration for testing purposes. In such an instance, the vibration control system thus operates as a vibration generator, with the output vibration faithfully following the input reference signal.

Figure 6:
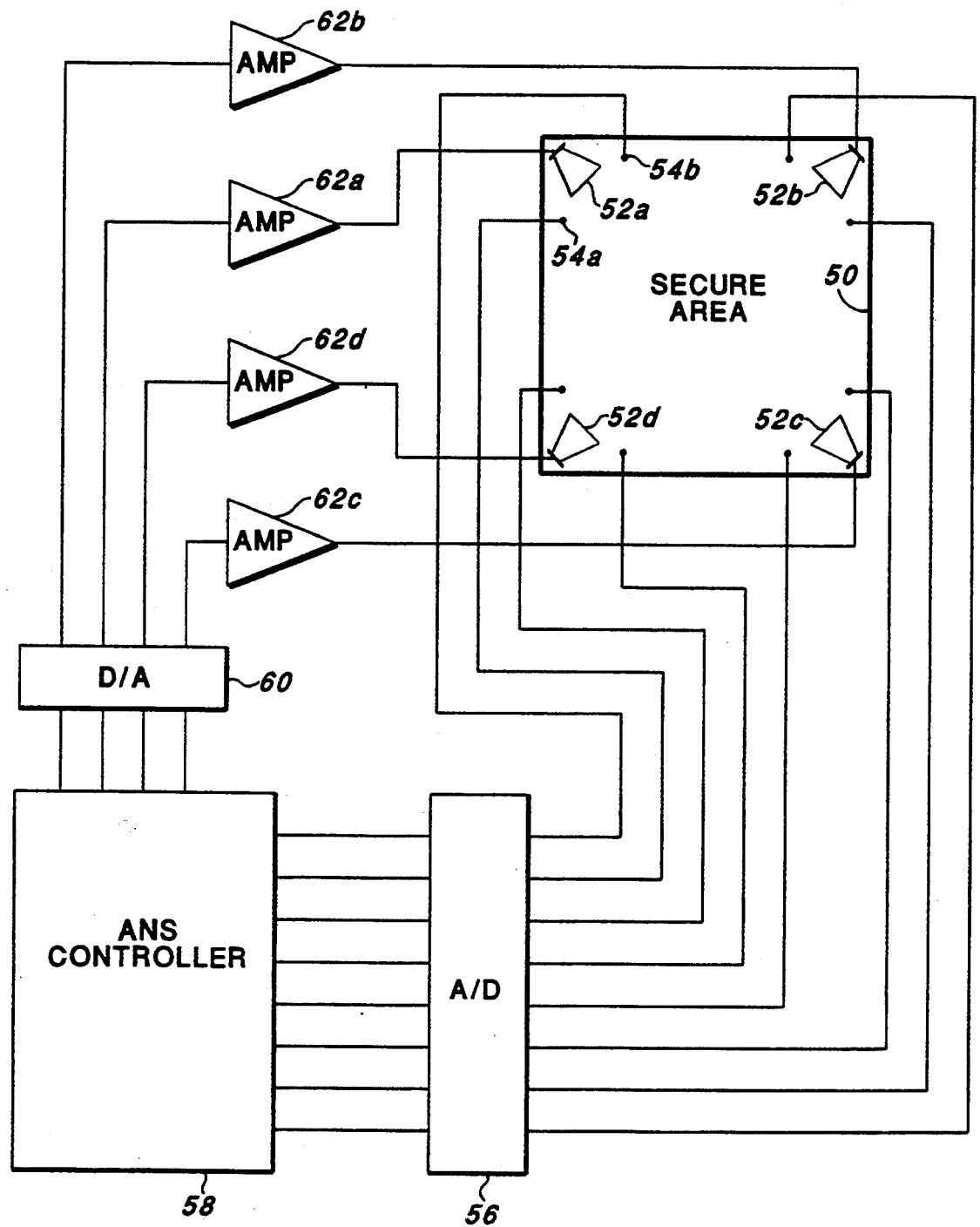
FIG. 6 schematically depicts a vibration control system used to secure an area from eavesdroppers.

FIG. 6 schematically depicts a vibration control system used to secure an area from eavesdroppers. The area to be secured is represented by the area within the square 50. This area may comprise an office or conference room. Four speakers (or speaker systems, or equivalent), 52a, 52b, 52c, and 52d are placed at appropriate locations around the area 50. As shown in FIG. 6, the speakers are located in the corners of the area 50. Adjacent each speaker is at least one microphone. For example, two microphones 54a and 54b are shown adjacent speaker 52a. Similarly, two microphones are placed adjacent the speakers 52b, 52c and 52d. It is noted that the ratio of two microphones for each speaker is only exemplary. More or less speakers and/or microphones may be used. Each microphone is coupled through an analog-to-digital (A/D) converter 56 to an ANS controller 58. Further, each speaker 52a, 52b, 52c, 52d is coupled to the ANS controller 58 through a digital-to-analog (A/D) converter 60 and respective amplifiers 62a, 62b, 62c, and 62d.

In operation, the microphones function as the sensors of the vibration control system, and the speakers function as the transducers. The medium is the air in the area 50. Any audible sounds, such as spoken words, that occur within the area 50 are sensed by each of the microphones, e.g., microphones 52a and 52b. These sounds thus become the "vibrations" that are canceled by the system at the monitoring points. Thus, upon sensing the sounds at the monitoring points, the ANS controller 58, operating in the manner as described above, generates appropriate control signals to drive the speakers 52a, 52b, 52c, and 52d, also positioned around the area 50, to cancel the sounds. Thus, an observer near the monitoring points is not able to detect any sound, and the area 50 is secure from eavesdroppers.

Figure 7:
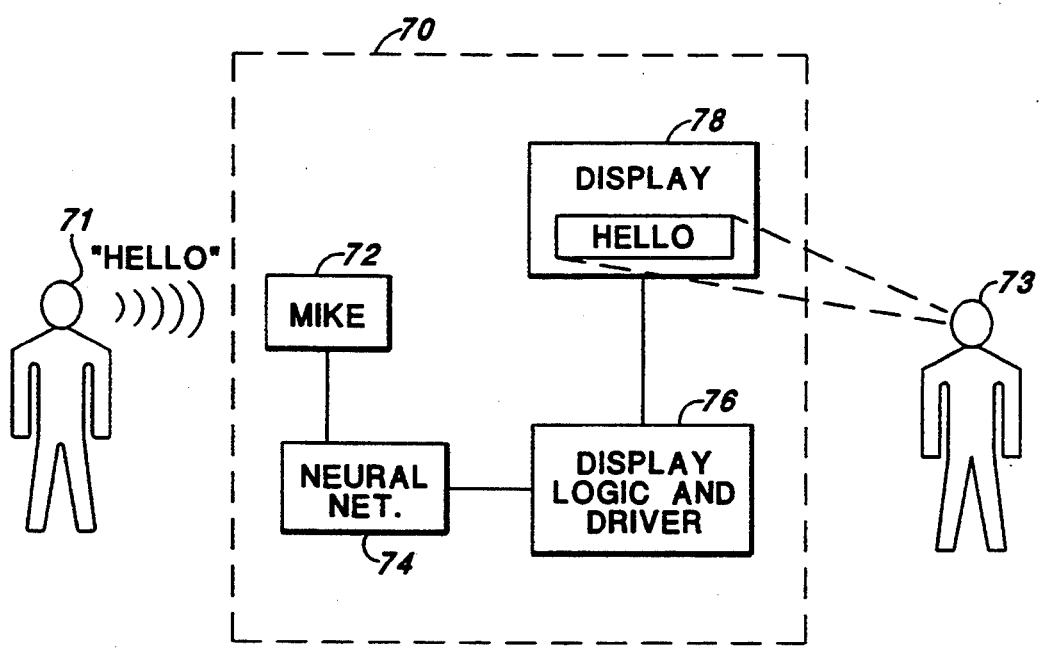
FIG. 7 shows a vibration control system used in a speech interpretation device.

FIG. 7 shows the block diagram of a speech interpretation device 70 that utilizes the vibration control principles of the present invention. Solving complex pattern-recognition problems implicit in understanding continuous speech has long been recognized as one of the strong points of a neural network. See, e.g., Hecht-Nielsen, *IEEE Spectrum*, above. Thus, the device depicted in FIG. 7 utilizes this inherent advantage of an neural network to provide an interpretation device 70 that may be used by the hearing impaired to better understand speech.

As seen in FIG. 7, the interpretation device 70 includes a microphone system 72, which system includes associated amplifiers and A/D converters to sense, amplify and condition speech sounds into digital signals. The digital signals from the microphone system 72 serve as the input to a chip-based neural network 74. The output of the neural network 74 is a sequence of signals representing the phonetic sounds present in the speech sounds. These phonetic signals are processed in conversion circuitry 76, which circuitry converts these signals to appropriate signals suitable for driving a suitable alphanumeric display 78. The display 78 displays sequences of letters representative of the phonetic sounds that have been heard, conditioned by the neural network so as to represent an accurate sequence of the sounds actually spoken.

Thus, when a person 71 speaks a given sequence of words, these words are processed by the neural network and converted into a sequence of letters representative of the words. The sequence of letters are then displayed on the display 78 such that a user 73 of the device can see the words or phonetic sounds that are spoken, and thereby better understand the speech. Preferably, the device 70, including the display 78, is carried by the user 76, similar to the manner a hearing aid is carried by an individual. The display 78 may be built-in to a pair of glasses worn by the user 73, with the sequence of detected words being displayed on an inside surface of the glasses where only the user 73 can see it.

FIG. 8 shows a block diagram of a vibration table 80 and associated controls used in conducting Examples 1 and 2, described below.

Appendix A contains the code listing used to program the neurocomputer of FIG. 8 in accordance with a MIMO operating mode of the invention used below in Example 2. The code listing has been prepared in the programming language "C". It includes many comment statements and is believed to be self-explanatory when considered in view of the commercially available Sigma neurocomputer available from SAIC and the manuals accompanying such neurocomputer.

EXAMPLE 1

In order to demonstrate an application of neural networks to real time adaptive control, a neural network based controller was used to cancel vibration in a complex structure. The top of the vibration table 80 (FIG. 8) represented the complex vibrating structure. It comprised a flexible frame made from unistrut beams that were bolted together, having approximate dimensions of three feet by four feet. The construction of the frame made its vibration response non-linear and not easily modeled. Several containers of colored liquid, such as the container 82 containing colored liquid 84, were placed around the structure 80 to reveal the vertical vibration of the structure at various points. The frame or table 80 was mounted on rubber pads (not shown) at four points to isolate its vibration from appropriate supporting structure.

Attached to the center of the frame 80 was an electromagnetic shaker 86. The shaker 86 served as the source of vibrations to the frame 80. It thus simulated a large piece of machinery that might be causing problem vibrations in the frame or structure 80. Attached to one corner of the table frame 80 was another electromagnetic shaker 88. This shaker 88 was controlled by a neural network (neurocomputer) 92, through an amplifier 94 and a D/A converter 96, to cancel vibration at a given monitoring location on the table frame 80. An accelerometer 90 was used to sense the vibrations at the location where vibration cancellation was desired. Its output signal became the error signal applied to the neural network 92.

When the control signal to the corner shaker 88 was turned on, the vibration near the accelerometer 90 was canceled, as shown by a calm surface on the colored liquid 84.

The adaptive control system thus demonstrated was implemented on SAIC's Sigma work station, a 386 AT based computer having the Delta II floating point processor card installed therein. The Delta card has been specifically designed for high speed neural network computation, making real time control with networks possible. The Sigma system shown in FIG. 8 also contained a data acquisition card to interface the 386 AT computer to analog inputs from the accelerometers, such as accelerometer 90, and to the analog outputs to the shakers.

The block diagram of FIG. 8 helps to visualize the cancellation system and its interconnections. In FIG. 8, the flexible frame table top 80 is shown, along with the source shaker 86. Suitable isolation pads were used to isolate the table top from all other components of the system. The shaker 86 was driven by a wave form generator 98 in an open loop through a suitable amplifier 100.

In this example, a 20 Hz sine wave was used to drive the source shaker 86. The neural network 92, as implemented on the Delta II in the AT computer, required two inputs from the system. One input was from an accelerometer 102 on a reaction mass 104 of the source shaker 86. The other input came from the accelerometer 90 at the location where vibration cancellation was desired, and acted as the error signal for the network. The output of the network controlled the cancellation shaker 88 at the corner of the frame 80.

The block diagram of the neural network used in this example showed the back propagation paradigm with four layers, as shown in FIG. 2. The inputs from the source accelerometer 102 were sequentially loaded into a shift register 35 stages long. This formed the input layer. There were two hidden layers of 10 elements each and one element in the output layer. These layers were fully interconnected with some 540 weights, including bias weights.

The signal from the source accelerometer 102 fed forward through the time series input layer to form the output of the neural network. The signal from the error accelerometer 90 becomes the error term for the back propagation algorithm. This error was back propagated to adjust the weights of the network interconnections. This allowed the network to learn and adapt to changes in the control conditions. The entire process of signal acquisition, network feed forward, weight update, and final output to the shaker took less than a millisecond. This high speed processing capability allowed true wave form cancellation in real time.

To demonstrate the adaptive capabilities of the controller used in this Example, the error accelerometer 90 was first located in the corner of the frame 80 and cancellation control was turned on. The liquid surface smoothed as vibration was canceled at this point. Next, the error accelerometer 90 was moved to the middle of the side of the frame 90 near point $P_A$. The controller adapted its output to the new situation, calming the bottle of liquid (not shown) near point $P_A$, while the corner bottle 84 shook violently. Significantly, vibration cancellation was accomplished at a point remote from the cancellation shaker 88.

It was also shown that it was possible to cancel the motion of the center frame directly over the vibration source 86. That is, the accelerometer 90 was moved to point $P_B$. The corner shaker 88 was able to flex the frame 80 sufficiently to balance the force from the source shaker 86. The liquid surface of a bottle (not shown) at point $P_B$ was calmed in just a few seconds.

The above adapting to a new location was true for the case where the weights (used within the neural network) had already been trained and only needed to be varied incrementally for the different positions. Training the weights from scratch took longer.

EXAMPLE 2

This Example demonstrates vibration cancellation at multiple locations simultaneously. The same basic test configuration was used as is shown in FIG. 8, except that the frame table 80 was modified by installing a cancellation shaker at each corner with the source shaker 86 installed near the center as in Example 1 (FIG. 9). There were four error accelerometers, one at each corner of the frame 80, and one source accelerometer 102. All of the accelerometers were connected to the neuro-controller 92, which in turn provided four outputs to the four cancellation shakers.

Table 1 provides a list of the equipment used in Example 2. Table 2 shows the operating specifications of the vibration cancellation system thus realized.

The multiple-input, multiple-output, neurocontroller described in Tables 1 and 2 learned and canceled vibrations at the four locations simultaneously. Moving the four error accelerometers to the center, above the source shaker near point $P_B$, caused the system to adapt such that the cancellation shakers coordinated to cancel the vibration at the remote center location. The neural-controlled vibration cancellation process was exactly the same as the single shaker example (Example 1) described above, simply expanded to multiple cancellation locations.

Adaptive cancellation is, of course, just one of the applications of real time neural network control made possible by the neurocomputer (Sigma work station) 92 used in the above examples. Its Delta II floating point processing board, with 12 million bytes of memory and 22 million floating point operations per second of processing speed, opens up new horizons in the field of adaptive control.

TABLE 1

| | Configuration: |
|---|---|
| 1 each. | Computer system, PC 386AT (or 486AT) or compatible, with EGA or VGA color terminal, >20 Mb hard disk, 3.5 or 5.25 inch floppy disk, 2 Mb "zero" wait state memory, extended keyboard, Microsoft mouse (or equivalent), and at least 5 contiguous user slots available |
| 1 each. | SAIC DELTA II Fast Floating Point Processor (requires 3 user slots) |
| 1 each. | SAIC DAI 1016 DT Interface Module (uses one DELTA II slot) |
| 1 each. | Data Translation Date Conversion Module, DT2841-F16SE, uses one user slot, includes: 16 Channels Analog-to-Digital (A/D) 2 Channels Digital-to-Analog (D/A) cable and terminal strip interface manually adjustable sampling clock |
| 1 each. | ICS Data Conversion Module, AOB6, uses one user slot, includes: 6 Channels D/A cable and terminal strip interface |
| 5 each. | Ling Dynamic Systems Vibration Generator, includes: Model 411 shaker power amplifier & cables blower, host & cable |

TABLE 1-continued

| Configuration: | | |
|---|---|---|
| | AUX 400 auxiliary suspension | |
| 5 each. | Vibrametrics accelerometer, 1020-S | |
| 5 each. | Vibrametrics signal conditioner, P1000B or LP15-1B | |
| 5 each. | Vibrametrics Cable, 9353441-20 | |
| 5 each. | Vibrametrics Mounting Magnet, 9353425 | |
| 1 each. | SAIC 10 LP Filter Module | |
| 5 each. | SAIC 5 BNC Cable set, 20' long | |
| 1 each. | SAIC Vibration Demonstration Table | |
| 2 each. | Oscilloscope, 4 Channel, >100 Megahertz | |
| 2 each. | Signal Generator, Wavetek 132, or equivalent | |
| 1 lot. | SAIC Real-Time Artificial Neurocontroller Software (RTANCS), Single-Use License Includes: 1 copy RTANCS software RTANCS User Manual Vibration Canceling System (VCS) Configuration Manual VCS equipment documentation as supplied by equipment manufacturers as applicable | |
| 1 each. | SAIC DELTA Extended Assembler, version 2.16 or higher | |
| 1 each. | SAIC DELTA OS, version 1.1 or higher | |
| 1 each. | Microsoft Quick C, version 2.0 or higher | |
| 1 lot. | VCS integration VCS and TRANCS manuals and training materials. | |

TABLE 2

| Specification: | |
|---|---|
| The model consists of a steel frame table top, approximately 3' × 4', bolted unistrut construction. This table top is isolated with rubber mounts from a base of similar unistrut constriction. This table will accommodate five vibration generators, one of which serves as the vibration source, and four serve as multiple vibration cancelers. All vibration is in the vertical axis only. The operating characteristics of the demonstration system include: | |
| Frequency Range: | 20 Hz to 200 Hz |
| Excitation level: | <50 lb force peak/vibration generator |
| Excitation Types Include: | single frequency sinusoids complex multiple frequency sinusoids narrowband random combined sinusoids and narrowband random |
| Vibration Reduction Expected: | 20 dB ± 10 dB reduction of single frequency sinusoid at each of up to four arbitrary locations. reductions of multiple sinusoids depend on number and levels of peaks. Reduction of random will depend upon source strength and spectrum bandwidth. |

As described above, it is thus seen that the present invention provides vibration control systems adapted to control vibrations in real time for a wide variety of applications. One embodiment, for example, provides a vibration control system that cancels or otherwise conditions unwanted vibrations at a specified location or target point in a given medium. Another embodiment provides such vibration cancellation or conditioning at a site remote from a cancellation shaker (transducer). Yet another embodiment provides simultaneous vibration cancellation or conditioning at multiple monitoring points within the medium.

It is also seen from the above description that the present invention provides a vibration control system that automatically adapts to provide a desired vibration cancellation or conditioning at one or multiple target points within the medium, regardless of whether the target points remain stationary or move within the medium.

It is further seen that the invention provides the desired vibration control in real time, without the need to mathematically model the system or medium, and without having to program or carry out time-consuming complex algorithms.

It is further seen that the invention can be generalized to provide effective adaptive control to a wide range of diverses processes.

While the invention herein disclosed has been described by means of specific embodiments and applications thereof, numerous modifications and variations could be made thereto by those skilled in the art without departing from the scope of the invention set forth in the claims.

APPENDIX A

```

Vibration Control System Operating Shell
filtered x version

created: 15 May 1990

##/

/######## C library includes ########/ include <stdio.h>
include <math.h>
#include <conio.h>
#include <dos.h>
```

```c
#include <time.h>
#include <string.h>
#include <stdlib.h>
include <bios.h> include "deltaos.h"
include "netgraph.h"
#include "dtp53.h"
#include "dtp53e.h"

/****** APPLICATION SPECIFIC DEFINES ******/ define VERSION "5.3e"        /* Version number of dtdriver*/
define DEXFILE "dtp53e.dex"  /* name of delta program */
#define AOB6                  /* Define if AOB6 6-channel D/A board used with dt */
#define N_INIT   1000         /* Number of execute cycles to init            */
#define CPMAX    128          /* Number of samples to save as check point    */
#define NADCHAN  6            /* number of ad input channels */
#define DA_MAX   6            /* Number of d/a outputs                       */
#define INMAX    10           /* Number of inputs from delta for dt connect */

/* Mapping of inputs from ANSvib, index values into in[] for dt */ define A0 0                  /* A/D channel 0 (-1.0 .. 1.0) */
define A1 1                  /* A/D channel 1 (-1.0 .. 1.0) */
#define A2 2                  /* A/D channel 2 (-1.0 .. 1.0) */
#define A3 3                  /* A/D channel 3 (-1.0 .. 1.0) */
#define A4 4                  /* A/D channel 4 (-1.0 .. 1.0) */
#define A5 5                  /* A/D channel 5 (-1.0 .. 1.0) */
#define O0 6                  /* Net output 0 (-.5 .. .5) */
#define O1 7                  /* Net output 1 (-.5 .. .5) */
#define O2 8                  /* Net output 2 (-.5 .. .5) */
#define O3 9                  /* Net output 3 (-.5 .. .5) */

/* Mapping of outputs to the d/a board AOB6 for fout[] and DAout[] */ define DA0    0    /* Network output 0 */
define DA1    1    /* Network output 1 */
#define DA2    2    /* Network output 2 */
#define DA3    3    /* Network output 3 */
#define DA4    4    /* Select output 4 */
#define DA5    5    /* Select output 5 */

/****** Global variables ******/ if DTDEBUG == 1
int denbl = TRUE;
endif

MEM_REF key = (MEM_REF) 0x0418L;   /* keyboard buffer pointer */ union fl {
     float  f;
     long   l;
} sigmd[2048],              /* sigmoid table array */
  acts[1024],               /* activities array */
  wghts[1024],              /* weight table array */
  dwghts[1024],             /* weight change array */
  in[INMAX+1];              /* input from delta */ float         fout[DA_MAX];   /* array values for output */
unsigned int  DAout[DA_MAX];  /* array of scaled d/a values */
```

```
float CPvalues[CPMAX][INMAX];      /* Check point array */ long    step    = 0,               /* Processing step counter */
        stepc;                     /* Processing step counter @ start */
float   timec, timeoff;            /* Time hold variables */

FILE *fileout,*filep,*filesin;     /* Misc file handles */ char
     parmfile[30] = "DEFAULT",     /* name of the current parameter file */
     wghtfile[30] = "DEFAULT",     /* name of current weight file */
     command[80];                  /* dos command */ int 60flag;                        /* RunANS loop flag */
define STOP    0                  /* Code values for 60flag */
#define INIT    1
#define EXECUTE 2
#define LEARN   3
#define BREAK   -1

/* Menu variables */ float
     ctlr4    =  0.1,     /* network learning rate */
     ctlr1    =  0.001,   /* network learning rate */
     ctbth    =  1.0,     /* number of patterns for batch learning */
     ctmtm    =  0.2,     /* momentum used in batch learning */
     emlr4    =  0.1,     /* network learning rate */
     emlr1    =  0.001,   /* network learning rate */
     embth    =  1.0,     /* number of patterns for batch learning */
     emmtm    =  0.2,     /* momentum used in batch learning */
     wretn    =  0.999995,/* network weight retention */
     lrn      =  1.0,     /* learn flag, 0 = execute, 1 = learn */
     lem      =  1.0,     /* emulator learn flag */
     lct      =  1.0,     /* controller learn flag */
     ga0      =  1.0,     /* control input signal gain */
     ci0      =  10.0,    /* controller input gain */
     cd0      =  30.0,    /* controller first difference input gain */
     co0      =  1.0,     /* controller output 0 gain */
     co1      =  0.0,     /* controller output 1 gain */
     cse0     =  0.0,     /* controller error 0 gain */
     cf0      =  0.0,     /* controller input to output feedforward */
     ei0      =  10.0,    /* emulator input gain */
     ed0      =  30.0,    /* emulator first difference gain */
     ee0      =  1.0,     /* emulator error gain */
     eci0     =  10.0,    /* filtered x net input gain */
     ecd0     =  30.0,    /* filtered x net first difference gain */
     tgtd     =  0.0,     /* target time delay */
     alin     =  0.0,     /* ad1 used for shaker error calculation flag */
     ctgt     =  1.0,     /* controller target */
     emct     =  1.0,     /* emct network bypass flag */
     dcfb     =  0.0,     /* dc feedback gain */
     da4      =  0.0,     /* Select code for D/A channel 4 */
     da5      =  0.0,     /* Select code for D/A channel 5 */
     fs       =  1000.0,  /* sampling frequency */
     wghtmax  =  0.3,     /* max range of initialized weights */
     ldmax    =  1.0,     /* Max load */
     tol      =  0.0,     /* error tolerance */

/* high-pass filter variables */
```

```
        fc_hp     =  2.0,    /* high pass cutoff frequency */
        g_hp      =  70.0,   /* high pass filter gain */
        q_hp      =  0.8,    /* q for high pass filter */

/* low-pass filter variables */ fc_lp     =  2.0,    /* low pass cutoff frequency */
        q_lp      =  1.0,    /* q for low pass filter */

/* all-pass filter variables */ ft_ap,
        q_ap;

struct llist {                  /* Menu structure */
    char *l_name;
        float *l_value;
} list[] = {
                    "ctlr4",    &ctlr4, /* network learning rate */
                    "ctlr1",    &ctlr1, /* network learning rate */
                    "emlr4",    &emlr4, /* network learning rate */
                    "emlr1",    &emlr1, /* network learning rate */

"ctbth",    &ctbth, /* patterns per batch training */
                    "ctmtm",    &ctmtm, /* momentum in batch training */
                    "embth",    &embth, /* patterns per batch training */
                    "emmtm",    &emmtm, /* momentum in batch training */

"lrn",      &lrn,   /* Learn mode flag */
                    "lct",      &lct,   /* controller learn flag */
                    "lem",      &lem,   /* emulator learn flag */
                    "wretn",    &wretn, /* network weight retention */

"ci0",      &ci0,   /* controller input gain */
                    "ei0",      &ei0,   /* emulator input gain */
                    "cf0",      &cf0,   /* controller input to output feedforward */
                    "fs",       &fs,    /* Sample rate */

"cd0",      &cd0,   /* controller first difference input gain */
                    "ed0",      &ed0,   /* emulator first difference gain */
                    "da4",      &da4,   /* D/A channel 4 select code */
                    "fc_hp",    &fc_hp, /* hp filter cutoff freq */

"co0",      &co0,   /* controller output 0 gain */
                    "ee0",      &ee0,   /* emulator error gain */
                    "da5",      &da5,   /* D/A channel 5 select code */
                    "q_hp",     &q_hp,  /* hp filter q */

"cse0",     &cse0,  /* controller error 0 gain */
                    "eci0",     &eci0,  /* filtered x input gain */
                    "ldmax",    &ldmax, /* Max A1 value */
                    "g_hp",     &g_hp,  /* hp filter gain */

"ctgt",     &ctgt,  /* controller target */
                    "ecd0",     &ecd0,  /* filtered x first difference gain */
                    "tgtd",     &tgtd,  /* target time delay */
                    "alin",     &alin,  /* ad1 in shaker error */

"dcfb",     &dcfb,  /* dc feedback gain */
                    "emct",     &emct,  /* emct bypass flag */
                    "ga0",      &ga0,   /* control signal gain */
                    "tol",      &tol    /* error tolerance */
};
```

```c
    int listlen = sizeof(list)/sizeof(struct llist);  /* Number of entries in list */

/*################################################################
#             MAIN() - main program
#######
##########################################################*/ void
main(int argc, char *argv[])
{ int i, k, c;
    char    FileName[30],
            name[20],                   /* array of parameter names */
            listinput[80];              /* input of list variables */
    float value;

CLEAR_SCREEN;                       /* Clear the screen */

/* screen heading */
    printf("\nDTP ver %s  dexfile: %s\n\n",VERSION,DEXFILE);

/* load the sigmoid table array */
    printf("reading the sigmoid table....\n");
    if (filep=fopen("sigmoid.tbl","rb")) {
        c=fread (sigmd,sizeof(long),2048,filep);
        printf("read %d items\n",c);
        fclose(filep);
    }
    else {
        printf("\n\acannot open sigmoid.tbl file\n");
        exit(0);
    }

/* set up Delta FPP for use */
    printf("Setting up the Delta FPP for operation....\n");
    dlt_startup();                      /* initialize the delta OS */
    printf("Downloading the dex file....\n");
    dlt_ld_prog(DEXFILE);               /* download the dex file */

/* send the sigmoid table */
    printf("Send sigmoid table....\n");
    dlt_senddelta(2048L,LOWER_NUM,&sigmd[0].1,SIGTABLE);
    initwghts(wghtmax,'b');             /* initialize ctweights */ if DTDEBUG == 1
    fileout = fopen("IO.LST", "w");     /* Open test data file */
endif ResetIO();                          /* Reset A/D and DT connect */ if (argc == 2) {                    /* If parameter entered on cmd line */
        if (ReadMenuParams(argv[1]))    /* Read in parameters */
            strcpy(paramfile,argv[1]) ;
    }
    else {
        if (ReadMenuParams("AUTO"))
            strcpy(paramfile,"AUTO") ;
    }

/*#### Put up display ####*/
```

```
          while(1) {                    /* Do forever */ if DTDEBUG == 1
          fprintf(fileout, "\n[Main loop]...\n");
#endif

CLEAR_SCREEN;
          printf(" DTP ver %s  dex: %s  param: %s  wghts: %s\n",
                 VERSION,DEXFILE,parmfile,wghtfile);
          if (step != 0) {
              if (GOflag == BREAK)      /* Check if broke */
                  printf("Auto stopped at step %ld, Processed %ld steps in %.2f seconds.",
                      step, step-stepc, (timeoff-timec));
              else
                  printf("Stopped at step %ld, Processed %ld steps in %.2f seconds.",
                      step, step-stepc, (timeoff-timec));
              printf("\n                Average processing rate = %.3f msec / step\n\n",
                  1000.0*(timeoff-timec)/(float)(step-stepc));
          }

/* print the parameter table */
          printf("                  -- CURRENT PARAMETER VALUES  --\n");

/* first two variables special because of weight retention */
          printf(" %-6s= %-9.3f",list[0].l_name,(float)*list[0].l_value); /* learn rate */
          printf(" %-6s= %-9.6f",list[1].l_name,(float)*list[1].l_value); /* weight retn */

/* print the rest of the table */
          for(k=2;k<ListLen;k++) {
              printf(" %-6s= %-9.3f",list[k].l_name,(float)*list[k].l_value);
              if (k % 4 == 3)
                  printf("\n");
          }

/* print the command table */
          printf("\n                       -- COMMAND MENU -- \n");
          printf("       c: Continue ANS processing    n: set New parameter value\n");
          printf("       s: Save parameters to file    r: Restore parameters from file\n");
          printf("       i: Initialize weights         w: store Weights to file\n");
          printf("       l: Load weights from file     d: Execute dos command\n");
          printf("       e: Exit                       v: View the networks\n");
          printf("\n >> Enter: Command select character: ");

/* get input and decode */
          c = GetAChar();
          switch(tolower(c)) {
    case 'c':                   /* Continue with ANS processing command */
          CLEAR_SCREEN;
          printf("\n >> ANS Processing Active ... \n\n");
          printf("       Press: Esc to stop processing  or  '.' to check point\n");
          RunANS();
          ResetID();            /* Reset A/D and DT connect */
          while(kbhit())        /* Flush input character */
              GetAChar();
          break;

case 'n':                   /* Input new parameter value */
          printf("\n >> Enter: Parameter name and Value (separate with space): ");
          gets(listinput);
          if (sscanf(listinput," %s %f",name,&value) != 2) /* expect two variables */
              break;
```

```c
            for(k=0;k<ListLen;++k) {          /* try to match with list table */
                if (!strcmp(name,list[k].l_name)) {
                    *list[k].l_value = value;
                    break;
                }
            }
            if (k == ListLen) {         /* if no match then warning */
                printf(" ?? Invalid variable name, input ignored.\n");
                printf(" >> Press any key to continue.");
                GetAChar();
            }
            break;

case 's':                       /* Save parameters command */
            printf("\n >> Enter: Save file name (.par): ");
            gets(FileName);
            if (strcmp(FileName,"")) {
                if (WriteMenuParams(FileName))
                    strcpy(parmfile,FileName);
            }
            break;

case 'r':                       /* Read parameters command */
            printf("\n >> Enter: Read file name (.par): ");
            gets(FileName);
            if (strcmp(FileName,"")) {
                if (ReadMenuParams(FileName))
                    strcpy(parmfile,FileName);
            }
            break;

case 'i':                       /* Initialize weights command */
            printf("\n >> Enter: initialize (c,e,b): ");
            k = tolower(GetAChar());
            if (k == 'c'|| k == 'e' || k == 'b')
                initwghts(wghtmax,(char)k);
            break;

case 'w':                       /* Save weights to a file */
            printf("\n >> Enter: Save file name (.wgt): ");
            gets(FileName);
            if (strcmp(FileName,"")) {
                if (savewghts(FileName))
                    strcpy(wghtfile,FileName);
            }
            break;

case 'l':                       /* load weights command */
            printf("\n >> Enter: Read file name (.wgt): ");
            gets(FileName);                     /* get filename */
            if (strcmp(FileName,"")) {
                printf(" >> Enter: Load weights to (c,e,b): ");
                k = tolower(GetAChar());            /* get network to load */
                if (k == 'c'|| k == 'e' || k == 'b')    /* ignore if only return */
                    if (loadwghts(FileName,(char)k))
                        strcpy(wghtfile,FileName);      /* update header if successful */
            }
            break;

case 'd':                       /* Execute dos command */
```

```c
                printf("\n >> Enter: DOS command: ");
                gets(command);
                if (strcmp(command,"")) {    /* return-key skips instruction */
                        strlwr(command);
                        if(system(command) == -1)
                                perror("error in system");
                        getch();
                }
                break;

case 'v':                       /* View the network */
                showtime();
                break;

case 'e':                       /* Exit command */
                printf("\n >> Do you really want to exit (y,n)?: ");
                c = GetAChar();
                if (tolower(c) == 'y')
                        exit(0);
                break;

default:
                break;
        } /* end of the switch */
    } /* end of while */
} /* End of main() */

/*##################################################################

RunANS() - Run the ANS loop

#############################################################*/ void
RunANS(void)
{
        int
                i, j, k, c,             /* misc counters variables */
                CPct,                   /* checkpoint counter */
                CPflag,                 /* checkpoint flag */
                InitCt,                 /* counter for ramp up delay */
                xda4,                   /* index to in[] for da4 output */
                xda5;                   /* index to in[] for da5 output */ float
                GoDegen,                /* ramp up count */
                DeltaGoDegen,           /* incremental output per count */
                *CPpointer,             /* memory ptr for saving chkpoint values */
                fnhp,                   /* normalized hp freq cutoff */
                kah, kbh, kch,          /* hp filter constants */
                fnlp,                   /* normalized lp freq cutoff */
                kal, kbl, kcl,          /* lp filter constants */
                pi      = 2*asin(1);    /* constant pi */ if DTDEBUG == 1
        fprintf(fileout, "\n[RunANS]...\n");
#endif

/* second order high pass filter constants (Chamberlin) */
        fnhp    = fc_hp / fs;
        kah     = 2*cos(2*pi*fnhp)*exp(-pi*fnhp/q_hp);
        kbh     = exp(-2*pi*fnhp/q_hp);
        kch     = g_hp*cos(pi*fnhp)*sqrt(1-kah+kbh);
```

```
/* second order low pass filter constants (Chamberlin) */
fnlp    = fc_lp / fs;
kal     = 2.0*cos(2.0*pi*fnlp)*exp(-pi*fnlp/q_lp);
kbl     = exp(-2.0*pi*fnlp/q_lp);
kcl     = (1.0 - kal + kbl);

/* show filter constant values */
printf ("\nfilter constants:\n");
printf ("fnhp= %f, kah= %f, kbh= %f, kch= %f\n",fnhp,kah,kbh,kch);
printf ("fnlp= %f, kal= %f, kbl= %f, kcl= %f\n\n",fnlp,kal,kbl,kcl);

#if DELTA
    /* execute the delta resident program */
    printf("execute delta\n");
    dlt_executedelta(BATCHTRAIN,IMMED_MASK,0L,databuf,NWAIT);

/* Send parameter values to delta */
    WaitOutputFull();               /* Wait on output fifo full */
    WriteWord(CMD_DTPARAMS);        /* Send command code */

WriteWord(ML(ctlr4));           /* ct network learning rate 4 layer */
    WriteWord(ML(ctlr1));           /* ct network learning rate 1 layer */
    WriteWord(ML(ctbth));           /* ct network patterns per batch */
    WriteWord(ML(ctmtm));           /* ct network momentum */
    WriteWord(ML(emlr4));           /* em network learning rate 4 layer */

WriteWord(ML(emlr1));           /* em network learning rate 1 layer */
    WriteWord(ML(embth));           /* em network patterns per batch */
    WriteWord(ML(emmtm));           /* em network momentum */
    WriteWord(ML(wretn));           /* network weight retention */
    WriteWord(ML(tol));             /* error tolerance */

WriteWord(ML(lct));             /* controller learning flag */
    WriteWord(ML(lem));             /* emulator learning flag */
    WriteWord(ML(ga0));             /* control input signal gain */
    WriteWord(ML(ci0));             /* controller input gain */
    WriteWord(ML(cd0));             /* controller first difference gain */

WriteWord(ML(cse0));            /* shaker error 0 to controller gain */
    WriteWord(ML(co0));             /* controller output 0 gain */
    WriteWord(ML(cf0));             /* controller input feedthru gain */
    WriteWord(ML(ei0));             /* emulator input gain */
    WriteWord(ML(ed0));             /* emulator first difference gain */

WriteWord(ML(ee0));             /* emulator error gain */
    WriteWord(ML(eci0));            /* filtered x input gain */
    WriteWord(ML(ecd0));            /* filtered x first difference gain */
    WriteWord(ML(tgtd));            /* target time delay */
    WriteWord(ML(alin));            /* ad1 used for shaker error flag */

WriteWord(ML(ctgt));            /* controller target gain */
    WriteWord(ML(emct));            /* emct network bypass flag */
    WriteWord(ML(dcfb));            /* dc feedback gain */
    WriteWord(ML(kah));             /* hp filter constant a */
    WriteWord(ML(kbh));             /* hp filter constant b */

WriteWord(ML(kch));             /* hp filter constant c */
    WriteWord(ML(kal));             /* lp filter constant a */
    WriteWord(ML(kbl));             /* lp filter constant b */
```

```
            WriteWord(ML(kc1));          /* lp filter constant c */
            PacketEnd();
endif
            printf("Updated Delta Parameters\n");
            /* Initialize loop state variables */
            CPct = CPMAX;                 /* Set checkpoint counter to max */
            CPflag = FALSE;               /* Set CP occured flag to false */
            GOflag = INIT;                /* Set INITflag to true */
            InitCt = N_INIT;              /* Set init counter to # init cycles */
            GoDegen = 0.0;                /* ramp up count */
            DeltaGoDegen = 1.0 / N_INIT;  /* incremental output per count */

/* Setup for D/A channel 4 and 5 */
            xda4 = (int)da4;              /* get table values */
            xda5 = (int)da5;
            if (xda4 < 0 | xda4 > INMAX) {    /* Check for out of range */
                  xda4 = INMAX;
                  fout[DA4] = 0.0;            /* if true then zero output */
            }
            if (xda5 < 0 | xda5 > INMAX) {    /* Check for out of range */
                  xda5 = INMAX;
                  fout[DA5] = 0.0;            /* if true then zero output */
            }

/* clear input array */
            for (i=0; i<=INMAX; i++)      /* Init in array */
                  in[i].f = 0.0;

/* Get start time */
            timec = GetSecond();
            stepc = step;

#if DELTA
            /* Kick off 1 execute cycle to get Delta waiting on fifo */
            WaitOutputFull();
            WriteWord(CMD_DTEXECUTE);     /* start execute cycle */
            PacketEnd();

outport(ADCLK, (XXTRGEN|APS|ACNT));  /* Enable A/D to run */
            outport(DACLK, (XXTRIG|DPS|DCNT));

/* wait for fifo to receive data from the delta */
            if (!TimedWaitInputEmpty()) {    /* Wait on data in fifo */
                  printf("Timeout waiting on fifo input empty after execute.\n");
                  step++;
                  GOflag = STOP;
                  getch();
            }

/* read data from the fifo */
            for (i=0,j=0; i<INMAX; i++) {    /* Get input values from fifo    */
                  in[i].l = ReadWord();      /* Get value as a long           */
            }

/* check for delta error flag = 0xffffffff in ad inputs */
            if (in[A0].l == (long)0xffffffff) {
                  printf("Timeout error from Delta after first execute cycle.");
                  GOflag = STOP;
                  getch();
                  for (j=0;j<INMAX;j++)
```

```
              in[j].f = 0.0;
        }
        printf("Finished preliminary Execute cycle\n");
endif /*** Main run loop ***/ while (GOflag != STOP && GOflag != BREAK ) {
                step++;
                switch (GOflag) {              /* Select command based upon GOflag value */
                        case INIT:                      /* In initialize phase */
                                if (InitCt-- == 0) {    /* Test for end of initct */
                                        if (lrn == 0.0) {       /* Test learn flag */
                                                GoDegen = 1.0;
                                                GOflag = EXECUTE; /* Not learning */
                                                printf("\n... Net is not learning");
                                        }
                                        else {
                                                GoDegen = 1.0;
                                                GOflag = LEARN; /* We are learning */
                                                printf("\n... Net is learning");
                                        }
                                }
                                else
                                        GoDegen += DeltaGoDegen; /* In all cases fall thru & do execute */ case EXECUTE:
if DELTA
                                WaitOutputFull();       /* Wait if output fifo full */
                                WriteWord(CMD_DTEXECUTE); /* Send command code to execute */
                                PacketEnd();

endif break;

case LEARN:
#if DELTA
                                WaitOutputFull();       /* Wait if output fifo full */
                                WriteWord(CMD_DTLEARN); /* Send command code to learn */
                                PacketEnd();
endif break;
                } if DELTA
        /* Get the response from delta to learn or execute request */
        WaitInputEmpty();               /* Wait for data in fifo */
        for (i=0,j=0; i<INMAX; i++) {   /* Get input values from fifo */
                in[i].l = ReadWord();   /* Get value as a long */
#if DTDEBUG == 1
                in[i].f = (float)1.0;   /* In debug all values = 1.0 */
#endif
        }
else
        for (i=0; i<INMAX; i++) {       /* squarewave generator for debug */
                if (in[i].f != 1.0)
                        in[i].f = 1.0;
                else
                        in[i].f = -1.0;
        }
#endif
```

```c
/* check for delta error flag = 0xffffffff in ad inputs */
if (in[A0].l == (long)0xffffffff) {
    printf("Timeout error from Delta in the main input loop.");
    GOflag = STOP;
    getch();
    for (j=0;j<INMAX;j++)
        in[j].f = 0.0;
}

/* Generate and send values to the D/A */
/* Check if force produced > max */
if (fabs(in[A0].f) > ldmax) {
    GOflag = BREAK;                 /* Stop the process */
    for (i=0;i < DA_MAX;i++)
        fout[i] = 0.0;              /* Zero all outputs */
}
else {

/* Load output values into floating point array */
    fout[DA0] = (in[O0].f) * GoDegen;
    fout[DA1] = (in[O1].f);
    fout[DA2] = (in[O2].f);
    fout[DA3] = (in[O3].f);

if (xda4 != INMAX)              /* check if output required */
        fout[DA4] = in[xda4].f;     /* Select D/A 4 value */
    if (xda5 != INMAX)              /* check if output required */
        fout[DA5] = in[xda5].f;     /* Select D/A 5 value */
}

/* Load d/a registers on the AOB6 */
for (i=0; i < DA_MAX ;i++) {
    if (fout[i] < -0.5) fout[i] = -0.5; /* Threshold all values */
    if (fout[i] >  0.5) fout[i] =  0.5;
    DAout[i] = (unsigned int)((fout[i] + 0.5)* 2.0 * (float)ZERO - 0.5);
                                                    /* Scale for d/a */
    outp(DABASE + (2*i), LOWBYTE(DAout[i])); /* Load low byte to d/a */
    outp(DABASE + (2*i+1), HIBYTE_LOWNYBBLE(DAout[i])); /* Load high byte to d/a */
}
STROBE_OUT();                       /* Strobe outputs simultaneously */

/* Check for check point in progress */
if (CPct != CPMAX) {                /* Test for in check point */
    for (i=0; i<INMAX; i++)         /* Save in[i] values */
        *CPpointer++ = in[i].f;
    CPct++;
}

/* Test keyboard for special ops */
if ((c = (_bios_keybrd(_KEYBRD_READY) & 0xFF)) == ESC) /* Check for stop */
    GOflag = STOP;
else {
    if (c == '.') {                 /* Check for check point req */
        CPflag = TRUE;              /* Set check point flag */
        CPct = 0;                   /* Reset CP ct */
        CPpointer = &CPvalues[0][0]; /* Set pointer to start of values */
    }
}
if (c != 0)                         /* Test for char in */
    _bios_keybrd(_KEYBRD_READ);     /* Pull the char from buffer */

} /* End of while GOflag != STOP */
```

```
        /* turn off the step timer */
        timeoff = GetSecond();               /* Get end time */ if DELTA
        /* send delta stop command control returns to the delta OS */
        WaitOutputFull();
        WriteWord(CMD_STOP);
        PacketEnd();
endif /* If checkpoint occured, dump checkpoint data to file */
        if (CPflag) {                        /* ? Check point occured */
                printf("\n wait while printing checkpt.val file ......");
                filesin=fopen("CHECKPT.VAL", "w");   /* Open check point file */
                for (i=0; i<CPMAX; i++) {            /* For all check point values */
                        for (j=0; j<INMAX; j++) {    /* For all entries */
                                fprintf(filesin, "%10.6f ", (float)CPvalues[i][j]);
                        }
                        fprintf(filesin, "\n");
                }
                fclose(filesin);
        }

/* Ramp d/a outputs to 0v */
        while ((fabs(fout[DA0]) > 0.005) || (fabs(fout[DA1]) > 0.005) ||
                (fabs(fout[DA2]) > 0.005) || (fabs(fout[DA3]) > 0.005) ) {
                for (i=0; i < 4; i++) {
                        if (fout[i] > 0.001)          /* decrease abs value of fout */
                                fout[i] -= 0.001;
                        if (fout[i] < -0.001)
                                fout[i] += 0.001;
                        DAout[i] = (unsigned int)((fout[i] + 1.0) * (float)ZERO - (float)0.5);
                                                      /* Scale for d/a */
                        outp(DABASE + (2*i), LOWBYTE(DAout[i]));
                                                      /* Load low byte to d/a */
                        outp(DABASE + (2*i+1), HIBYTE_LOWNYBBLE(DAout[i]));
                                                      /* Load high byte to d/a */
                }
                STROBE_OUT();                         /* Strobe outputs simultaneously */
        } return;
} /* End of RunANS */

/*****************************************************************
******
******           ResetIO() - Reset A/D and DT connect interface
******
*****************************************************************/ void
ResetIO(void)
{
        int i;

#if DTDEBUG == 1
        fprintf(fileout, "\n[ResetIO]...\n");
#endif

/* Initialize A/D & D/A portion of IO */
        outport(ADCLK, (XXINIT));           /* Init A/D */
        outport(DACLK, (XXINIT));           /* Init D/A */
```

```
        /* Init channel list to 0,1,2,3,4,5 */
        outport(CGLCSR, (LAE + NADCHAN-1));    /* Enable channel list wr */
        outport(ADCSR, 0);
        outport(ADCSR, 1);
        outport(ADCSR, 2);
        outport(ADCSR, 3);
        outport(ADCSR, 4);
        outport(ADCSR, 5);
        outport(CGLCSR, NADCHAN-1);            /* Reset channel list wr enable */ outport(ADCSR, (SCENA | PLM));         /* Preload aux and set scan mode */
        outport(DACSR, (SEL_ADCNTR));          /* Select ADCNTR */
        outport(ADCNTR, ADCNTR_VALUE);         /* Init ADCNTR */ outport(DACSR, (SEL_DACNTR));          /* Select DACNTR */
        outport(DACNTR, DACNTR_VALUE);         /* Init DACNTR */
        /* Set D/A outputs to 0 V */
        outport(DACSR, (SSEL | ERRCTRL));      /* select da0 */
        outport(PIODAT, DAC0V);                /* Set DAC channel 0 to 0 V */
        outport(DACLK, (XXTRIG | DPS | DCNT)); /* Trigger D/A */
        outport(DACSR, (YSEL | SSEL | ERRCTRL)); /* select da1 */
        outport(PIODAT, DAC0V);                /* Set DAC channel 1 to 0 V */
        outport(DACLK, (XXTRIG | DPS | DCNT)); /* Trigger D/A */
        outport(DACLK, XXINIT);                /* Re-init DAC to stop conversion */ ifdef A086
        /* set d/a values on the A086 d/a card to zero */
        for (i=0; i<6; i++) {      /* Load the d/a registers with zero count */
                outp(DABASE + (2*i), LOWBYTE(ZERO));
                outp(DABASE + (2*i+1), HIBYTE_LOWNYBBLE(ZERO));
        }
        STROBE_OUT();              /* Strobe out zero values simultaneously */
endif if DELTA
        /* Reset DT connect interface */
        dlt_executedelta(CMD_DTINIT,IMMED_MASK,0L,databuf,NWAIT);
endif /* Enable A/D DT port interface */
        outport(DACSR, (ERRCTRL|SEL_PORTCSR));
        outport(PORTCSR, (DAXCE|DAPEN|ADXCE|ADPEN));   /* Enable A/D port continous mode */
        return;
}

/*****************************************************************
******
******          WriteMenuParams() - write parameter variables to file
******
*****************************************************************/ int
WriteMenuParams(char *FileName)
{
        int k, c;

if((filep=fopen(FileName,"rb")) != NULL) {
                printf("\n ?? File Is exists,  overwrite (y/n) ?? ",FileName);
                if(tolower((c = GetAChar()) != 'y'))
                        return(0);
```

```c
}
printf("\nWriting file %s ...", FileName);
if((filep=fopen(FileName,"w")) == NULL) {
        printf("\n ?? File %s could not be opened\n",FileName);
        printf(" >> Press any key to continue. ");
        k = GetAChar();
        return(0);

}
        else {
                for(k=0;k<ListLen;++k) {
                        fprintf(filep, "%s %g\n", list[k].l_name, (float) *list[k].l_value);
                }
                fclose(filep);
        }
        return(1);
}

/**************************************************************
******
******              ReadMenuParams() - read parameter variables from file
******
**************************************************************/ int
ReadMenuParams(char *FileName)
{
        int k, pct, c, ErrFlag;
        char name[20];
        float value;

ErrFlag = FALSE;
        if((filep=fopen(FileName,"r")) == NULL) {
                printf("\n ?? File %s could not be opened\n",FileName);
                printf(" >> Press any key to continue. ");
                c = GetAChar();
                return(0);
        }
        else {
                do {
                        pct = fscanf(filep, " %s %g", name, &value);  /* Get a name, value pair */
                        if (pct == 2) {
                                for (k=0; k<ListLen; k++) {            /* Search for name */
                                        if (!strcmp(name,list[k].l_name)) { /* If got a match */
                                                *list[k].l_value = value;   /* Set value */
                                                break;
                                        }
                                }
                                if (k == ListLen) {                    /* Check if got a match */
                                   printf ("\n?? Unknown variable name %s found in file, ignored it.\n", name);
                                   ErrFlag = TRUE;
                                }
                        }
                } while (pct == 2);
        }
        fclose(filep);
        if (ErrFlag) {
           printf("\n>> Parameter errors, Press any key to continue.\n");
           GetAChar();
        }
```

```
      return(1);
}

/********************************************************************
******
******          GetSecond() - Get current time expressed in seconds
******
********************************************************************/ float
GetSecond(void)
{
      struct dostime_t tme;

_dos_gettime(&tme);
      return ((tme.hour*3600+tme.minute*60+tme.second) +
              (tme.hsecond)/100.0);
}

/********************************************************************
******
******          WriteWord() - Write a long word to delta fifo
******
********************************************************************/ void
WriteWord(unsigned long lData)
{
      outport(DEFAULT_BASE+WRITE_LSBS, (unsigned)lData);
      outport(DEFAULT_BASE+WRITE_MSBS, (unsigned)(lData >> 16));
}

/********************************************************************
******
******          ReadWord() - Read a long word from delta fifo
******
********************************************************************/ unsigned long
ReadWord (void)
{
      return ((unsigned long)inport(DEFAULT_BASE+READ_MSBS) << 16) | inport(DEFAULT_BASE+READ_LSBS);
}

/********************************************************************
******
******          GetAChar() - Read a single character from keyboard
******
********************************************************************/ int
GetAChar(void)              /* Get a single character routine */
{
      int ch;

if ((ch=getche()) == 0)      /* Get a single char from keyboard */
             ch = getch() | 0x80;   /* if 0, is a fcn key set c to code */
      return(ch);
}

/********************************************************************
******
```

```
TimedWaitOutputFull() - wait on fifo output full with timeout

###########################################################/ long
TimedWaitOutputFull()
{
        long counts = 20000;

while (((inport(DEFAULT_BASE+STATUS) & 0x2) == 0) && --counts);
        return(counts);
}

/################################################################

TimedWaitInputEmpty() - wait on fifo input empty with timeout

###########################################################/ long
TimedWaitInputEmpty()
{
        long counts = 80000;

while (((inport(DEFAULT_BASE+STATUS) & 0x1) == 0) && --counts);
        return(counts);
}

/################################################################

initwghts() - init the weight segment with small random values

###########################################################/ void
initwghts(float wmax, char nn)
{
        int i;
        unsigned seed;
        time_t currenttime;

/* use the current time for the seed */
        time(&currenttime);
        seed = (unsigned)currenttime;
        srand(seed);

/* load controller weights with random between wmax and -wmax */
        if (nn == 'c' || nn == 'b') {
                printf("\n initializing the ctweights.....");
                for (i=0;i<1024;i++) {
                        wghts[i].f = ((float)rand()/32767.0)*2.0*wmax-wmax;
                        dwghts[i].f = 0.0;
                }
                printf("\n sending to delta...");
                dlt_senddelta(1024L,UPPER_NUM,&wghts[0].1,CTWGHTS); /* send array to delta board */
                dlt_senddelta(1024L,UPPER_NUM,&dwghts[0].1,CTDWGHTS);
        }

/* load emulator weights with random between wmax and -wmax */
        if (nn == 'e' || nn == 'b') {
                printf("\n initializing the emweights.....");
                for (i=0;i<1024;i++) {
```

```
                    vghts[i].f = ((float)rand()/32767.0)*2.0*vmax-vmax;
                    dvghts[i].f = 0.0;
            }
            printf("\n sending to delta...");
            dlt_senddelta(1024L,UPPER_NUM,&vghts[0].1,EMWGHTS);  /* send array to delta board */
            dlt_senddelta(1024L,UPPER_NUM,&dvghts[0].1,EMDWGHTS);
        }
        return;
}

/*****************************************************************
******
******      savewghts() - save the weight segment to a file
******
*****************************************************************/ int
savewghts(char *FileName)
{
    int k, c;

if((filep=fopen(FileName,"rb")) != NULL) {     /* test to see if overwrite */
            printf("\n ?? File %s exists,  overwrite (y/n) ?? ",FileName);
            if(tolower((c = GetAChar()) != 'y'))
                    return(0);
    }
    printf("Writing file %s ...", FileName);    /* open file for writing */
    if((filep=fopen(FileName,"wb")) == NULL) {
            printf("\n ?? File %s could not be opened",FileName);
            printf("\n >> Press any key to continue. ");
            k = GetAChar();
            return(0);
    }
    else {
            /*store controller weights from delta */
            dlt_requestdelta(1024L,UPPER_NUM,&vghts[0].1,CTWGHTS);   /* delta ctweights into buffer */
            printf("\nsaving the ctweight array.....");
            c=fwrite (vghts,sizeof(long),1024,filep);  /* save ctweight buffer */
            printf("wrote %d items",c);

/*store emulator weights from delta */
            dlt_requestdelta(1024L,UPPER_NUM,&vghts[0].1,EMWGHTS);   /* delta emweights into buffer */
            printf("\nsaving the emweight array.....");
            c=fwrite (vghts,sizeof(long),1024,filep);  /* save emweight buffer */
            printf("wrote %d items",c);
            fclose(filep);
    }
    return(1);
}

/*****************************************************************
******
******      loadwghts() - load the weight segment from a file
******
*****************************************************************/ int
loadwghts(char *FileName,char nn)
{
    int k, c, i;
```

```
if((filep=fopen(FileName,"rb")) == NULL) {     /* open the file */
      printf("\n ?? File %s could not be opened",FileName);
      printf("\n >> Press any key to continue. ");
      c = GetAChar();
      return(0);
}
printf("\nreading file %s.....",FileName);

/* zero the weight change array */
for (i=0;i<1024;i++) {
      dwghts[i].f = 0.0;
}

/* get controller weights to delta */
if (nn == 'c'|| nn == 'b') {
      c=fread (wghts,sizeof(long),1024,filep);    /* read weights from file */
      printf("\nread %d items",c);
      printf("\nsend ctwghts to delta .....");
      dlt_senddelta(1024L,UPPER_NUM,&wghts[0].1,CTWGHTS);       /* weights to delta */
      dlt_senddelta(1024L,UPPER_NUM,&dwghts[0].1,CTDWGHTS);     /* zero weight change array */
}

/* get emulator weights to delta */
      if (nn == 'e'|| nn == 'b') {
            c=fread (wghts,sizeof(long),1024,filep);    /* read weights from file */
            printf("\nread %d items",c);
            printf("\nsend ewghts to delta .....");
            dlt_senddelta(1024L,UPPER_NUM,&wghts[0].1,EMWGHTS);       /* weights to delta */
            dlt_senddelta(1024L,UPPER_NUM,&dwghts[0].1,EMDWGHTS);     /* zero weight change array */
      }
      fclose(filep);
      return(1);
}

/*##################################################################

showtime() - view the networks

############################################################*/ void
showtime()
{
int emrows[]={1,1,1,1,10,10,1},
      emcols[]={40,10,10,1,41,11,11},
      ctrows[]={1,1,1,1,10,10,1},
      ctcols[]={40,10,10,1,41,11,11};

if (init_graphics())
            return;

/* view emulator first */
      dlt_requestdelta(1024L,UPPER_NUM,&wghts[0].1,EMWGHTS);    /* delta ewghts into buffer */
      dlt_requestdelta(1024L,LOWER_NUM,&acts[0].1,EMACT);       /* delta emact into buffer */
      graph_net("EMULATOR NETWORK",4,emrows,emcols,&acts[0].f,&wghts[0].f);

/* view emct network */
      dlt_requestdelta(1024L,UPPER_NUM,&wghts[0].1,EMWGHTS);    /* delta ewghts into buffer */
      dlt_requestdelta(1024L,LOWER_NUM,&acts[0].1,EMCTACT);     /* delta emctact into buffer */
      graph_net("EMULATOR/CONTROLLER NETWORK",4,emrows,emcols,&acts[0].f,&wghts[0].f);

/* view controller */
```

```c
    dlt_requestdelta(1024L,UPPER_NUM,&vghts[0].1,CTWGHTS);   /* delta ctvghts into buffer */
    dlt_requestdelta(1024L,LOWER_NUM,&acts[0].1,CTACT);      /* delta ctact into buffer */
    graph_net("CONTROLLER NETWORK",4,ctrows,ctcols,&acts[0].f,&vghts[0].f);

/* view controller filtered x */
    dlt_requestdelta(1024L,UPPER_NUM,&vghts[0].1,CTWGHTS);   /* delta ctfxvghts into buffer */
    dlt_requestdelta(1024L,LOWER_NUM,&acts[0].1,CTFXACT);    /* delta ctfxact into buffer */
    graph_net("CTFX NETWORK",4,ctrows,ctcols,&acts[0].f,&vghts[0].f);

end_graph();
    return;
}

/*************************** DTPS3.H ***************************/

/* Defines and function prototypes for DTDRIVER.C */ define DTDEBUG 0
define DELTA 1

/******* Type definitions *******/ typedef volatile unsigned char (far *MEM_REF);
typedef float REAL;

/******* Constants *******/ define TRUE 1
define FALSE 0 define ESC '\x1B'                      /* Single escape char */

/* Delta board register addresses */ if 1
define DEFAULT_BASE    0x240
#define READ_LSBS       0x0
#define READ_MSBS       0x2
#define STATUS          0x4
#define WRITE_LSBS      0x8
#define WRITE_MSBS      0xA
#define PACKET_STROBE   0xC
#define DELTA_RESET     0xE
endif /* Delta board commands from PC interface */ define CMD_STOP        0x00L   /* Stops net; returns control to delta os */
define CMD_DTEXECUTE   0x10L   /* Input from DT, call exe, output results */
#define CMD_DTLEARN     0x20L   /* Input from DT, call learn, output results */
#define CMD_DTPARAMS    0x30L   /* Set DT parameter values                */

/* DT2841 A/D - D/A defines */ define BASE    0x3E0           /* DT2841 A/D & D/A I/O base addr */
define ADCSR   BASE            /* A/D Control/Status register */
#define CGLCSR  BASE + 2        /* Channel-Gain List Control/Status register */
#define DACSR   BASE + 4        /* D/A Control/Status register */
#define PORTCSR BASE + 6        /* PORT Control/Status register (DACSR 3,2 = 00) */
#define ADCNTR  BASE + 6        /* A/D counter register (DACSR 3,2 = 01) */
```

```c
#define DACNTR   BASE + 6      /* D/A counter register (DACSR 3,2 = 10) */
#define PIODAT   BASE + 8      /* Program I/O DATa */
#define ADDAT    BASE + 0xA    /* A/D in DATa and D/A out data */
#define ADCLK    BASE + 0xC    /* A/D CLoCk register */
#define DACLK    BASE + 0xE    /* D/A CLoCk register */

/* ADCSR - a/d control status register */
#define ADCLR        0x2000    /* clear a/d error */
#define SCENA        0x0400    /* scan enable */
#define PLM          0x0100    /* preload mux */

/* CGLCSR - channel gain list control status register */
#define LAE          0x8000    /* list access enable */

/* DACSR - d/a control status register */
#define DACLR        0x2000    /* clear d/a error */
#define SEQ          0x1000    /* sequential select */
#define READY        0x0800    /* ready d/a conversion complete */
#define YSEL         0x0200    /* y channel select */
#define SSEL         0x0100    /* single channel select */
#define ERRCTRL      0x0010    /* error control flag */
#define SEL_PORTCSR  0x0000    /* access portscr */
#define SEL_ADCNTR   0x0004    /* access adcntr */
#define SEL_DACNTR   0x0008    /* access dacntr */

/* PORTCSR - ap port control status register */
#define DAXCLR       0x2000    /* D/A clear done flag bit */
#define DAICE        0x1000    /* d/a continous transfer enable */
#define DAPEN        0x0100    /* d/a port enable bit flag */
#define ADXCLR       0x0020    /* a/d clear done flag bit */
#define ADICE        0x0010    /* A/D Continous transfer enable */
#define ADPEN        0x0001    /* A/D Port enable bit flag */

/* ADCNTR - a/d counter register */
#define ADCNTR_VALUE  0xFFFA   /* A/D block count (2's complement of 6) */

/* DACNTR - d/a counter register */
#define DACNTR_VALUE  0xFFFE   /* D/A block count (2's complement of 2) */

/* ADCLK - a/d clock register */
#define APS          0x0000    /* A/D Prescaler value (= / by 1) */
#define ACNT         0x009c    /* A/D Clock count (10.0 uSec @ 10 mHz) */

/* DACLK - d/a clock register */
#define DPS          0x0000    /* D/A Prescaler value (= / by 1) */
#define DCNT         0x009c    /* D/A Clock count (10.0 uSec @ 10 mHz) */

/* ADCLK and DACLK common commands */
#define XXINIT       0x8000    /* initialize */
#define XXTRIG       0x4000    /* software trigger */
define XXTRGEN      0x2000    /* external trigger enable */ define DAC0V        0x0000    /* D/A count value for 0 V */

/* AOB6 6-channel D/A and digital I/O defines */
#define DABASE   0x0300          /* AOB6 D/A I/O base addr */
#define DA0LOW   DABASE          /* D/A 0 low byte */
#define DA0HI    DABASE + 1      /* D/A 0 high byte */
#define DA1LOW   DABASE + 2      /* D/A 1 low byte */
#define DA1HI    DABASE + 3      /* D/A 1 high byte */
#define DA2LOW   DABASE + 4      /* D/A 2 low byte */
#define DA2HI    DABASE + 5      /* D/A 2 high byte */
```

```c
#define DA3LOW      DABASE + 6       /* D/A 3 low byte         */
#define DA3HI       DABASE + 7       /* D/A 3 high byte        */
#define DA4LOW      DABASE + 8       /* D/A 4 low byte         */
#define DA4HI       DABASE + 9       /* D/A 4 high byte        */
#define DA5LOW      DABASE + 0xA     /* D/A 5 low byte         */
#define DA5HI       DABASE + 0xB     /* D/A 5 high byte        */
#define PAPORT      DABASE + 0xC     /* PA port                */
#define PBPORT      DABASE + 0xD     /* PB port                */
#define PCPORT      DABASE + 0xE     /* PC port                */
#define CONTROL     DABASE + 0xF     /* Control port of 8255   */
#define STROBE_OUT() inp(DABASE)     /* Strobe simultaneous update */

/* da conversion defines */ define ZERO    0x8800               /* d/a value for zero volts output */
define LOWBYTE(i)  (i)&0xff
define HIBYTE_LOWNYBBLE(i)   ((i)>>8)&0x0f /****** Function DEFINES ******/ define amod(x1,x2) fmod(x1,x2)  /* not sure about this ! */
define aminl(x1,x2) ( ((x1)<(x2)) ? (x1) : (x2) )
#define amaxl(x1,x2) (((x1)<(x2)) ? (x2) : (x1))
#define sign(x1,x2)  ( ((x2)< 0.) ? (-fabs(x1)) : fabs(x1) )

#if DTDEBUG == 1
int denbl = TRUE;
endif if DTDEBUG == 1
define inport(z) (0xFFFF;(denbl ? fprintf(fileout,"inport(%4x)\n",z) : 0))
#define outport(z,y) (denbl ? fprintf(fileout,"--- outport(%4x, %4x)\n",z,y) : 0)
#else
#define inport(x) inpw(x)
#define outport(x,y) outpw(x,y)
endif define PacketEnd()      outport(DEFAULT_BASE+PACKET_STROBE, 0)
define WaitOutputFull() while ((inport(DEFAULT_BASE+STATUS) & 0x2) == 0)
#define WaitInputEmpty() while ((inport(DEFAULT_BASE+STATUS) & 0x1) == 0)
#define ML(f)            (*((long *)&(f)))
        /* ML(f): makes float into long value for passing floats as params */

/****** Function prototypes ******/ void    RunANS(void);                       /* Run the ANS loop */
    void    ResetIO(void);                      /* Reset A/D and DTconnect */
    int     ReadMenuParams(char *FileName);     /* Read the menu parameters in */
    int     WriteMenuParams(char *FileName);    /* Write the menu parameters out */
    float   GetSecond(void);                    /* Get the current second */
    void    WriteWord (unsigned long);          /* Write long value to Delta fifo */
    unsigned long ReadWord (void);              /* Read long value from Delta fifo */
    int     GetAChar(void);                     /* Get a single character routine */
    long    TimedWaitOutputFull(void);          /* Wait on fifo output full with timeout */
    long    TimedWaitInputEmpty(void);          /* Wait on fifo input empty with timeout */
    void    initwghts(float,char);              /* Initialize the delta controller weight segment */
    int     loadwghts(char *Filename,char nn);  /* Load the weight array from file */
    int     savewghts(char *FileName);          /* Save the weight array to file */
    void    showtime();                         /* View the networks */
```

; File: dtp53e.sas
; Vibration Control System Delta II Software
; use: backpropagation for shaker linearization
;
; created: 18 July 90
;
; author: Bruce MacKay
;
; This program is based on the 'filtered x' controller from Widrow.
; An emulator network emulates the plant to be controlled. The emulator
; is then used to condition, or filter, the input to the controller, x,
; that is feed forward for the weight update only. The x input to the
; controller that is fed forward to the plant is not filtered.

program filteredx

```
        #include "deltaos.sas"         ;delta operating system files
        #include "bpmacros.sas"        ;backprop macros
        #include "linmacro.sas"        ;linear macros ;misc defines
        #define   NADCHAN    6         ;number of a/d channels
        #define   NDTPARAMS  34        ;number of dt parameters
        #define   TDSIZE     20        ;time series delays
        #define   SUMSIZE    20        ;square error sum ;constant defines
        #define   W_DECAY    1         ;with weight decay
        #define   WO_DECAY   0         ;without weight decay ;controller network defines
        #define   CTNSERIES  2         ;number of time series in input layer
        #define   CTNLAYER   4         ;number of layers in the network
        #define   CTLSIZE0   40        ;size layer 0
        #define   CTLSIZE1   10        ;size layer 1
        #define   CTLSIZE2   10        ;size layer 2
        #define   CTLSIZE3   1         ;size layer 3
        #define   CTLSIZEOUT CTLSIZE3  ;output layer size ;controller indexes into the activity and error segments
        #define   CTL0       0
        #define   CTL1       CTL0 + CTLSIZE0
        #define   CTL2       CTL1 + CTLSIZE1
        #define   CTL3       CTL2 + CTLSIZE2
        #define   CTLOUT     CTL3
        #define   CTNLSIZE   CTLOUT+CTLSIZEOUT ;total size of all the net layers ;controller indexes into the bias/weight segment
        #define   CTW01      0
        #define   CTW12      CTW01 + (CTLSIZE0+1)*CTLSIZE1
        #define   CTW23      CTW12 + (CTLSIZE1+1)*CTLSIZE2
        #define   CTW03      CTW23 + (CTLSIZE2+1)*CTLSIZE3 ;direct connect weights
        ;emulator network defines
        #define   EMNSERIES  2         ;number of time series in input layer
        #define   EMNLAYER   4         ;number of layers in the network
        #define   EMLSIZE0   40        ;size layer 0
        #define   EMLSIZE1   10        ;size layer 1
        #define   EMLSIZE2   10        ;size layer 2
        #define   EMLSIZE3   1         ;size layer 3
        #define   EMLSIZEOUT EMLSIZE3  ;output layer size ;emulator indexes into the activity and error segments
```

```
        #define    EML0       0
        #define    EML1       EML0 + EMLSIZE0
        #define    EML2       EML1 + EMLSIZE1
        #define    EML3       EML2 + EMLSIZE2
        #define    EMLOUT     EML3
        #define    EMNLSIZE   EMLOUT+EMLSIZEOUT  ;total size of all the net layers ;emulator indexes into the bias/weight segment
        #define    EMW01      0
        #define    EMW12      EMW01 + (EMLSIZE0+1)*EMLSIZE1
        #define    EMW23      EMW12 + (EMLSIZE1+1)*EMLSIZE2
        #define    EMW03      EMW23 + (EMLSIZE2+1)*EMLSIZE3
        #define    EMNWSIZE   EMW03 + (EMLSIZE0+1)*EMLSIZE3  ;direct connect weights ;controller network arrays
worg    seg $$
global  CTwghts    float * 1024          ;bias/weight matrices worg    seg $$
global  CTdwghts   float * 1024          ;bias/weight change matrices lorg    seg $$
global  CTact      float * CTNLSIZE   =  ;activity arrays
                                                    #for i = 0 to CTNLSIZE
                                                            float(0)
                                                    #endfor
global  CTFXact    float * CTNLSIZE   =  ;activity arrays
                                                    #for i = 0 to CTNLSIZE
                                                            float(0)
                                                    #endfor
global  CTtarget   float * CTLSIZEOUT    ;target array
global  CTerrors   float * CTNLSIZE      ;error arrays
global  CTtgtdel   float * TDSIZE     =  ;times series for input a0 delay
                                                    #for i = 0 to TDSIZE
                                                            float(0)
                                                    #endfor
global  sqr_err    float * TDSIZE     =  ;times series for square error
                                                    #for i = 0 to SUMSIZE
                                                            float(0)
                                                    #endfor
lorg    seg $$
global  CTtdwghts  float * 1024          ;temporary weight change matrices ;emulator network arrays
worg    seg $$
global  EMwghts    float * 1024          ;bias/weight matrices worg    seg $$
global  EMdwghts   float * 1024          ;bias/weight change matrices lorg    seg $$
global  EMact      float * EMNLSIZE   =  ;activity arrays
                                                    #for i = 0 to EMNLSIZE
                                                            float(0)
                                                    #endfor
global  EMCTact    float * EMNLSIZE   =  ;activity array for prop cntlr error
                                                    #for i = 0 to EMNLSIZE
                                                            float(0)
                                                    #endfor
global  EMtarget   float * EMLSIZEOUT    ;target array
global  EMerrors   float * EMNLSIZE      ;error arrays
```

```
lorg    seg $$
global  EMtdwghts   float # 1024        ;temporary weight change matrices ;sigmoid lookup table
lorg    seg $$
global  sigtable    float # 2048        ;sigmoid table forg    0x20

;dai 1016 and fifo interface commands
        selreset    word    =   0x32    ;Select DAI 1016 reset mode
        selcs       word    =   0x22    ;Select DAI 1016 command status
        seltc       word    =   0x12    ;Select DAI 1016 transfer counter
                                        ;   Used on reads from slave device only
                                        ;   Not used here
        seldai      word    =   0x100   ;Address for dai number one
        selrw       word    =   0x02    ;Select DAI 1016 for read and write
        selhost     word    =   0x01    ;Select Host device for I/O
        daimode     word    =   0x4ec   ;sign extend on bit 15
                                        ;   NRTS on empty flag
                                        ;   enable buffer 1 = input from DT master
        daimode1    word    =   0x8ec   ;sign extend on bit 15 enable buffer 1
                                        ;   disable nrts ;misc parameters
        ad [NADCHAN]    float           ;a/d inputs
        adout [NADCHAN] float           ;a/d outputs
        scalefact       float   =   0.5/2048.0 ;conversion factor = 0.5/2K for 12 bit a/d
        errflag         word    =   0xffffffff ;error flag
        ;floating point numeric constants
        one             float   =   1.0
        two             float   =   2.0
        half            float   =   0.5
        pt_005          float   =   0.005   ;scale factor for sqr_err vs lrate
        tenth           float   =   0.1

;integer numeric constants
        onevolt         word    =   0x900
        zerovolts       word    =   0x800
        minus_onevolt   word    =   0x700

;delay registers
        ad0d1           float   =   0.0     ;delayed ad0 for derivative
        ftrxd1          float   =   0.0     ;delayed filtered x for derivative
        ctoutd1         float   =   0.0     ;delayed ctoutput for derivative
        hpd1 [NADCHAN]  float   =           ;filter delay 1
                                            #for i = 0 to NADCHAN
                                                float(0)
                                            #endfor
        hpd2 [NADCHAN]  float   =           ;filter delay 2
                                            #for i = 0 to NADCHAN
                                                float(0)
                                            #endfor
        hpo1 [NADCHAN]  float   =           ;filter delayed intermediate output
                                            #for i = 0 to NADCHAN
                                                float(0)
                                            #endfor
        lpd1 [CTLSIZEOUT] float =           ;lp filter delay 1
                                            #for i = 0 to CTLSIZEOUT
                                                float(0)
                                            #endfor
```

```
lpd2 [CTLSIZEOUT] float =           ;lp filter delay 2
                                        #for i = 0 to CTLSIZEOUT
                                            float(0)
                                        #endfor
ctdc [CTLSIZEOUT] float =           ;gain adjusted controller outputs
                                        #for i = 0 to CTLSIZEOUT
                                            float(0)
                                        #endfor ;misc storage of variables
        shakererror     float   =   0.0     ;shaker error
        bpshakererror   float   =   0.0     ;bandpassed shaker error
        emerror         float   =   0.0     ;emulator error
        ctarget         float   =   0.0     ;controller target
        ad0diff         float   =   0.0     ;ad0 first difference
        ctout           float   =   0.0     ;controller output signal
        fltrdx          float   =   0.0     ;ad0 filtered through the emulator
        ctnetout        float   =   0.0     ;output of the CT net
        embatchcntr     word    =   0x0     ;emulator counter for batch learning
        ctbatchcntr     word    =   0x0     ;controller counter for batch learning
        bplvibout       float   =   0.0     ;bandpassed shaker out fundamental
        vibout          float   =   0.0     ;shaker output
        emout           float   =   0.0     ;emulator output
        ctlr4_lin       float   =   0.0     ;learning rate for linear layer
        emlr4_lin       float   =   0.0     ;learning rate for linear layer
        lrn             word    =   0x1     ;learning flag 0=on 1=off ;command and parameters passed from PC to delta using CMD_DTPARAMS
global  command         word ;dt parameters
        ctlr4           float           ;ct learning rate 4 layer
        ctlr1           float           ;ct learning rate 1 layer
        ctbatch         float           ;ct patterns per batch
        ctmomtm         float           ;ct momentum
        emlr4           float           ;em learning rate 4 layer emlr1           float           ;em learning rate 1 layer
        embatch         float           ;em patterns per batch
        emmomtm         float           ;em momentum
        fdecay          float           ;weight retention
        tol             float           ;error tolerance lct             float           ;controller learn flag 0=off,1=on nobatch,>1 batch
        lem             float           ;emulator learning flag   off=0
        ga0             float           ;gain on control signal input
        ci0             float           ;gain controller net input
        cd0             float           ;gain controller net first diff input cse0            float           ;gain for controller error 0
        co0             float           ;gain for controller net output 0
        cf0             float           ;gain for input feedtru to output
        ei0             float           ;gain emulator net input
        ed0             float           ;gain emulator net first diff input ee0             float           ;gain emulator net error
        eci0            float           ;gain emulator controller input
        ecd0            float           ;gain emulator controller first diff input
        tgtd            float           ;ctarget time delay before shakererror calculation flag
        alin            float           ;use ad1 for ct target flag
```

```
        ctgt        float               ;controller target gain
        eact        float               ;eact bypass flag
        dcfb        float               ;dc feedback gain
        ka          float               ;hp filter constant a
        kb          float               ;hp filter constant b kc          float               ;hp filter constant c
        lka         float               ;lp filter constant a
        lkb         float               ;lp filter constant b
        lkc         float               ;lp filter constant c
porg $$
```

;;; BATCHTRAIN
;;;
;;; command handler and program entry entry  BATCHTRAIN

```
                        ;wait for a command from the host
                        jmp.ip      **              ;wait for input not empty
                        input.alu                   ;first input is command
                        storea.fil  command         ;store in command variable
                        rts.zr                      ;return if STOP command #x00

;use command to find jump table address
                        inegx.im    4               ;shifting command right by 4
                        scregv.alu                  ;load shift count register
                        ls.fil      command         ;do shift
                        iadd.im     &JMPTABLE-1     ;add table address with command offset
                        jsr         @alu            ;indirect jump to command
                        jmp         BATCHTRAIN      ;return to batchtrain loop JMPTABLE    jmp         CMD_DTEXECUTE   ;0x10 Input from DT, call exe, output results
            jmp         CMD_DTLEARN     ;0x20 Input from DT, call learn, output results
            jmp         CMD_DTPARAMS    ;0x30 Set DT parameter values
```

;;; ************

;;; CMD_DTPARAMS
;;;
;;; Set DT parameter values

CMD_DTPARAMS
```
                        #for i = 0 to NDTPARAMS         ;do for number of dt parameters
                            input.fil   command+1+i     ;get dt parameters
                        #endfor ;calculate linear layer learning rate
                        loada.fil   ctlr4           ;apy = ct learning rate
                        mult.fil    tenth           ;apy = 0.1*ctlrn4
                        storea.fil  ctlr4_lin       ;save as linear learn rate
                        loada.fil   ealr4           ;apy = ea learning rate
                        mult.fil    tenth           ;apy = 0.1*ealrn4
                        storea.fil  ealr4_lin       ;save as linear learn rate
                        rts
```

;;; ************

;;; CMD_DTINIT
;;;
;;; initialize DT interface called through the Delta OS

```
entry   CMD_DTINIT
                sib.fil    seldai           ;set dai number 1 to active
                sib.fil    selreset         ;select dai 1016 reset mode
                output.alu                  ;any write does reset
                sib.fil    seldai           ;reset dai number 1 to active
                sib.fil    selcs            ;select dai 1016 command status reg
                loada.fil  daimodel         ;disable nrts on the dai
                output.alu
                sib.fil    selhost          ;reselect host for i/o
                RETURN_OK()
;;; ############

;;; CMD_DTLEARN
;;;
;;; basic learning routine when using DT connect for data input CMD_DTLEARN     loada.im   1
                storea.fil lrn              ;set learning flag to on
                jsr        STEP_NETWORK     ;do one time step
                rts
;;; ############

;;; CMD_DTEXECUTE
;;;
;;; execute routine using dt connect for data input

CMD_DTEXECUTE
                loada.im   0
                storea.fil lrn              ;set learning flag to off
                jsr        STEP_NETWORK     ;do one time step
                rts
;;; ############

;;; STEP_NETWORK
;;;
;;; routines to advance the network one time step

STEP_NETWORK
                jsr        DTADDPAT         ;get input data and scale
                jmpn.zr    ERREXIT          ;error in DTADDPAT
                jsr        INPUTFILTERS     ;filter the inputs
                jsr        STORE_ADIN       ;store the ad inputs
                jsr        CTINPUT          ;form the controller input
                jsr        CTFEEDFORWARD    ;feedforward thru controller
                jsr        CTOUTPUT         ;sum signals for controller output
                jsr        EMINPUT          ;setup emulator input
                jsr        EMFEEDFORWARD    ;feedforward thru emulator
                jsr        SENDOUT          ;send a/d and output to host
                loada.fil  lrn              ;get learning flag
                jmp.zr     OKEXIT           ;jump if learning off
                loada.fil  lem              ;get emulator learn flag
                jsrn.zr    EMLEARNPATTERN   ;update emulator weights if lem#0
                loada.fil  lct              ;get controller learn flag
                jsrn.zr    CTLEARNPATTERN   ;update controller weights
OKEXIT          rts
ERREXIT         jsr        SENDOUT          ;notify host of error
                rts
;;; ############
```

```
;;; STORE_ADIN
;;;
;;; store the ad values in other variables for later use

STORE_ADIN     ;protect bandpass inputs
               loada.fil    ad[2]              ;alu = shaker output
               storea.fil   vibout
               rts
;;; ############

;;; CTINPUT
;;;
;;; form controller inputs

CTINPUT        ;adjust ad0 by input gain
               loada.fil    ad[0]              ;get ad0
               mult.fil     ga0                ;multiply by ad0 gain
               storea.fil   ad[0]              ;save ad0

;shift the ct time series
               jsr          CTADDTIMESTEP

;load controller input values
               loada.fil    ad[0]              ;multiply ad0 by gain
               mult.fil     ci0
               storea.fl    CTact+CTL0+0       ;store in activity input layer ;use derivative for second input
               loada.fil    ad[0]              ;get ad0(t)
               loada.fil    ad0d1              ;get ad0(t-1)
               storea.fil   ad0d1              ;update delayed ad0
               subx.apy                        ;alu = ad0(t)-ad0(t-1)
               storea.fil   ad0diff            ;store ad0 difference
               loada.alu                       ;transfer to apy
               mult.fil     cd0                ;multiply by gain
               storea.fl    CTact+CTL0+1       ;store in activity input layer
               rts
;;; ############
;;; CTOUTPUT
;;;
;;; sum signals for controller output CTOUTPUT
               ;get the controller output
               loada.fl     CTact+CTLOUT+0     ;get controller output
               mult.fil     co0                ;multiply by gain
               loada.apy                       ;accumulate controller output ;add control signal direct feedthru
               loada.fil    ad[0]              ;get ad0 input
               mult.fil     cf0                ;feedthru gain
               add.apy                         ;sum feedthru ;filter the control output to the shaker
               storea.fil   ad[3]              ;store for filtering
               jsr          CTOUTFILTER        ;filter the ctout
               loada.fil    ad[3]              ;get filtered ctout
               storea.fil   ctout              ;store as controller output
               rts
;;; ############
```

```
;;; EMINPUT
;;;
;;; form the emulator input signal

EMINPUT         ;shift the emulator input series
                jsr         EMADDTIMESTEP ;load emulator input values
                loada.fil   ctout               ;get controller output
                mult.fil    ei0                 ;multiply by emulator input gain
                storem.fl   EMact+EML0+0        ;store in activity layer ;use derivative for second input
                loada.fil   ctout               ;get ctout(t)
                loada.fil   ctoutd1             ;get ctout(t-1)
                storea.fil  ctoutd1             ;update delayed ctout
                subx.apy                        ;alu = ctout(t)-ctout(t-1)
                loada.alu                       ;transfer to apy
                mult.fil    ed0                 ;multiply by gain
                storem.fl   EMact+EML0+1        ;store in activity layer
                rts

;;; ############

;;; LEARNPATTERN
;;;
;;; backpropagate the errors and update the weights
EMLEARNPATTERN
                ;form the emulator target
                loada.fl    EMact+EMLOUT+0      ;alu = emulator output
                storea.fil  emout               ;store in emout
                sub.fil     vibout              ;alu = ad2 - emulator out
                storea.fil  emerror             ;emulator error
                loada.alu                       ;apy = emulator error
                mult.fil    ee0                 ;multiply by gain
                storem.fl   EMtarget+0          ;store as target ;update the emulator weights
                loada.fil   embatchcntr         ;get batch counter
                jsr.zr      EMSTARTPASS         ;if zero do startpass
                jsr         EMDOOUTERR          ;compute output errors
                jsr         EMDOHIDERR          ;propagate error backwards
                jsr         EMDOADJUST_B        ;update weight changes
                loada.fil   embatchcntr         ;get batch counter
                isubx.im    1                   ;decrement counter by 1
                storea.fil  embatchcntr         ;save new count
                jsr.zr      EMENDPASS           ;if zero do endpass
                rts CTLEARNPATTERN
                ;get error for ctfx error 0
                ;test for ad0 or ad1 to be used as target
                loada.fil   ad[0]               ;alu = ad0
                loada.fil   alin                ;apy = flag to use ad1 or ad0
                jmp.zr      USEAD0              ;if alin = 0 use ad0 for error
                jsr         AD1FILTER           ;filter the ad1 input
                loada.fil   ad[1]               ;alu = ad1
USEAD0          storea.fil  ctarget             ;alu => ctarget ;adjust ctarget for gain
                loada.fil   ctarget             ;apy = ctarget
                mult.fil    ctgt                ;multiply by target gain
```

```
                storea.fil  ctarget                 ;save as controller target SHKERR      ;calculate bp shaker error
                loada.fil   ctarget                 ;alu = ctarget
                subx.fil    vibout                  ;alu = ctarget - shaker output
                storea.fil  shakererror             ;store as band passed shakererror
#if 0
                jsr         ADJ_CTLRATE
#endif
                ;shift ctfx input layer for new input
                jsr         CTFXADDTIMESTEP         ;shift the ctfx time series ;check eact network bypass flag
                loada.fil   ad[0]
                loada.fil   eact
                jmp.zr      CTFXNET
                ;condition the input thru the emulator
                ;load eact input values
EMCTNET   jsr         EMCTADDTIMESTEP
                loada.fil   ad[0]                   ;multiply ad0 by gain
                mult.fil    eci0
                storea.fl   EMCTact+EMLO+0          ;store in activity layer ;use derivative for second input
                loada.fil   ad0diff                 ;mpy = ad0(t)-ad0(t-1)
                mult.fil    ecd0                    ;multiply by gain
                storea.fl   EMCTact+EMLO+1          ;store in activity layer ;feedforward through emulator to generate filtered x
                jsr         EMCTFEEDFORWARD
                loada.fl    EMCTact+EMLOUT+0

;load the ctfx input with the filtered x and shakererror
CTFXNET   storea.fil  fltrdx                 ;save filtered x for output
                mult.fil    ci0
                storea.fl   CTFXact+CTLO+0          ;store in activity layer ;use derivative for second input
                loada.fil   fltrdx                  ;get fltrdx(t)
                loada.fil   ftrxd1                  ;get fltrdx(t-1)
                storea.fil  ftrxd1                  ;update delayed fltrdx
                subx.mpy                            ;alu = fltrdx(t)-fltrdx(t-1)
                loada.alu                           ;transfer to mpy
                mult.fil    cd0                     ;multiply by gain
                storea.fl   CTFXact+CTLO+1          ;store in activity layer ;get dc correction terms for ctfx target
                #for i = 0 to CTLSIZEOUT            ;get ct network outputs
                    loada.fl    CTact+CTLOUT+i
                    storea.fil  ctdc[i]
                #endfor
                jsr         LOWPASSOUTPUT           ;low pass network output to dc
                #for i = 0 to CTLSIZEOUT            ;gain adjust dc terms
                    loada.fil   ctdc[i]
                    mult.fil    dcfb
                    storea.fil  ctdc[i]
                #endfor ;load ctfx targets
                loada.fil   shakererror             ;get shaker error
                mult.fil    cse0                    ;multiply error by cse0
                loada.fil   ctdc[0]                 ;alu = output dc
```

```
                sub.apy                         ;alu = error - dc
                storea.fl   CTtarget+0

;determine to batch or not to batch
                loada.fil   lct                 ;get ct learning flag
                cmpr.fil    one                 ;compare flag to 1
                jmp.zr      NO_BATCH            ;if lct=1 jump to NO_BATCH ;do batch learning on ctfx
                loada.fil   ctbatchcntr         ;get batch counter
                jsr.zr      CTFXSTARTPASS       ;if zero do startpass
                jsr         CTFXFEEDFORWARD     ;feed forward the CTFX activities
                jsr         CTFXDOOUTERR        ;compute output errors
                jsr         CTFXDOHIDERR        ;propagate error backwards
                jsr         CTFXDOADJUST_B      ;update weight changes
                loada.fil   ctbatchcntr         ;get batch counter
                isubx.im    1                   ;decrement counter by 1
                storea.fil  ctbatchcntr         ;save new count
                jsr.zr      CTFXENDPASS         ;if zero do endpass
                rts
NO_BATCH
                ;learn with no batching
                jsr         CTFXFEEDFORWARD     ;feed forward the CTFX activities
                jsr         CTFXDOOUTERR        ;compute output errors
                jsr         CTFXDOHIDERR        ;propagate error backwards
                jsr         CTFXDOADJUST        ;update weight changes
                rts
;;; ************

;;; STARTPASS
;;;
;;; prepare weight change matrices for batch processing

EMSTARTPASS STARTPASS(EMdwghts,EMNO1,EMNWSIZE,emmomtm)

;reload counter with number of patterns per batch
                loada.fil   embatch             ;get number of patterns in batch
                fcsi.alu                        ;convert to integer
                storea.fil  embatchcntr         ;reinitialize the batch counter
                rts CTFXSTARTPASS
                STARTPASS(CTdwghts,CTNO1,CTNWSIZE,ctmomtm)

;reload counter with number of patterns per batch
                loada.fil   ctbatch             ;get number of patterns in batch
                fcsi.alu                        ;convert to integer
                storea.fil  ctbatchcntr         ;reinitialize the batch counter
                rts
;;; ************

;;; ENDPASS
;;;
;;; update the emulator weight matrices with the weight change matrices
EMENDPASS   ENDPASS (EMwghts,EMdwghts,EMtdwghts,EMNO1,EMNWSIZE)
                rts CTFXENDPASS ENDPASS (CTwghts,CTdwghts,CTtdwghts,CTNO1,CTNWSIZE)
                rts
;;; ************
```

```
;;; FEEDFWD
;;;
;;; feed forward the inputs through the network and calculate outputs CTFEEDFORWARD
                FEEDFWD (CTact,CTwghts,CTL0,CTL1,CTW01,CTLSIZE0,CTLSIZE1)
                FEEDFWD (CTact,CTwghts,CTL1,CTL2,CTW12,CTLSIZE1,CTLSIZE2)
                FEEDFWD_LIN (CTact,CTwghts,CTL2,CTL3,CTW23,CTLSIZE2,CTLSIZE3)
                FEEDFWD_LIN_ADD (CTact,CTwghts,CTL0,CTL3,CTW03,CTLSIZE0,CTLSIZE3)
                DO_SIGMOID (CTact,CTLOUT,CTLSIZEOUT)
                rts CTFXFEEDFORWARD
                FEEDFWD (CTFXact,CTwghts,CTL0,CTL1,CTW01,CTLSIZE0,CTLSIZE1)
                FEEDFWD (CTFXact,CTwghts,CTL1,CTL2,CTW12,CTLSIZE1,CTLSIZE2)
                FEEDFWD_LIN (CTFXact,CTwghts,CTL2,CTL3,CTW23,CTLSIZE2,CTLSIZE3)
                FEEDFWD_LIN_ADD (CTFXact,CTwghts,CTL0,CTL3,CTW03,CTLSIZE0,CTLSIZE3)
                DO_SIGMOID (CTFXact,CTLOUT,CTLSIZEOUT)
                rts EMFEEDFORWARD
                FEEDFWD (EMact,EMwghts,EML0,EML1,EMW01,EMLSIZE0,EMLSIZE1)
                FEEDFWD (EMact,EMwghts,EML1,EML2,EMW12,EMLSIZE1,EMLSIZE2)
                FEEDFWD_LIN (EMact,EMwghts,EML2,EML3,EMW23,EMLSIZE2,EMLSIZE3)
                FEEDFWD_LIN_ADD (EMact,EMwghts,EML0,EML3,EMW03,EMLSIZE0,EMLSIZE3)
                DO_SIGMOID (EMact,EMLOUT,EMLSIZEOUT)
                rts EMCTFEEDFORWARD
                FEEDFWD (EMCTact,EMwghts,EML0,EML1,EMW01,EMLSIZE0,EMLSIZE1)
                FEEDFWD (EMCTact,EMwghts,EML1,EML2,EMW12,EMLSIZE1,EMLSIZE2)
                FEEDFWD (EMCTact,EMwghts,EML2,EML3,EMW23,EMLSIZE2,EMLSIZE3)
                FEEDFWD_LIN (EMCTact,EMwghts,EML2,EML3,EMW23,EMLSIZE2,EMLSIZE3)
                FEEDFWD_LIN_ADD (EMCTact,EMwghts,EML0,EML3,EMW03,EMLSIZE0,EMLSIZE3)
                DO_SIGMOID (EMCTact,EMLOUT,EMLSIZEOUT)
                rts
;;; ************

;;; DOOUTERR
;;;
;;; compute the errors for the output layer

EMDOOUTERR
                DOOUTERR (EMact,EMerrors,EMtarget,EMLSIZEOUT,EMLOUT,0)   ;use target as error
                rts
CTFXDOOUTERR
                DOOUTERR_WTOL (CTFXact,CTerrors,CTtarget,CTLSIZEOUT,CTLOUT,tol,0) ;use target as error
                rts
;;; **********

;;; DOHIDERR
;;;
;;; compute the errors for the hidden layers

CTFXDOHIDERR
                BKPROPERR (CTFXact,CTwghts,CTerrors,CTL2,CTL3,CTW23,CTLSIZE2,CTLSIZE3)
                BKPROPERR (CTFXact,CTwghts,CTerrors,CTL1,CTL2,CTW12,CTLSIZE1,CTLSIZE2)
                rts
```

ENDOHIDERR  BKPROPERR (EMact,EMwghts,EMerrors,EML2,EML3,EMW23,EMLSIZE2,EMLSIZE3)
            BKPROPERR (EMact,EMwghts,EMerrors,EML1,EML2,EMW12,EMLSIZE1,EMLSIZE2)
            rts

;;; ###########

;;; DOADJUST
;;;
;;; update the weight matrices

CTFXDOADJUST_B
            WGHTUPDATE_L (CTFXact,CTdwghts,CTerrors,CTL0,CTL1,CTW01,CTLSIZE0,CTLSIZE1,WO_DECAY,ctlr4)
            WGHTUPDATE_L (CTFXact,CTdwghts,CTerrors,CTL1,CTL2,CTW12,CTLSIZE1,CTLSIZE2,WO_DECAY,ctlr4)
            WGHTUPDATE_L (CTFXact,CTdwghts,CTerrors,CTL2,CTL3,CTW23,CTLSIZE2,CTLSIZE3,WO_DECAY,ctlr4_lin)
            WGHTUPDATE_L (CTFXact,CTdwghts,CTerrors,CTL0,CTL3,CTW03,CTLSIZE0,CTLSIZE3,WO_DECAY,ctlr1)
            rts CTFXDOADJUST
            WGHTUPDATE_L (CTFXact,CTwghts,CTerrors,CTL0,CTL1,CTW01,CTLSIZE0,CTLSIZE1,W_DECAY,ctlr4)
            WGHTUPDATE_L (CTFXact,CTwghts,CTerrors,CTL1,CTL2,CTW12,CTLSIZE1,CTLSIZE2,W_DECAY,ctlr4)
            WGHTUPDATE_L (CTFXact,CTwghts,CTerrors,CTL2,CTL3,CTW23,CTLSIZE2,CTLSIZE3,W_DECAY,ctlr4_lin)
            WGHTUPDATE_L (CTFXact,CTwghts,CTerrors,CTL0,CTL3,CTW03,CTLSIZE0,CTLSIZE3,W_DECAY,ctlr1)
            rts EMDOADJUST_B
            WGHTUPDATE_L (EMact,EMdwghts,EMerrors,EML0,EML1,EMW01,EMLSIZE0,EMLSIZE1,WO_DECAY,emlr4)
            WGHTUPDATE_L (EMact,EMdwghts,EMerrors,EML1,EML2,EMW12,EMLSIZE1,EMLSIZE2,WO_DECAY,emlr4)
            WGHTUPDATE_L (EMact,EMdwghts,EMerrors,EML2,EML3,EMW23,EMLSIZE2,EMLSIZE3,WO_DECAY,emlr4_lin)
            WGHTUPDATE_L (EMact,EMdwghts,EMerrors,EML0,EML3,EMW03,EMLSIZE0,EMLSIZE3,WO_DECAY,emlr1)
            rts

;;; ###########

;;; SENDOUT
;;;
;;; send the a/d inputs and network outputs to the PC

SENDOUT     ;ad0 = filtered ad0 input
            loada.fil   ad[0]
            storea.fil  adout[0]

;ad1 = controller target
            loada.fil   ctarget
            storea.fil  adout[1]

;ad2 = filtered ad2 input
            loada.fil   ad[2]
            storea.fil  adout[2]

;ad3 = CTFX output
            loada.fl    CTFXact+CTLOUT+0
            storea.fil  adout[3]

;ad4 = CT differential input
            loada.fl    CTact+CTL0+1
            storea.fil  adout[4]

;ad5 = emulator error
            loada.fil   emerror
            storea.fil  adout[5]

;send the ad[] values

```
            jmpn.of    &&                          ;wait until output flags clear
            #for i = 0 to NADCHAN
                    output.fil adout[i]            ;output ad channels
            #endfor ;d0 = controller output
            output.fil  ctout                      ;get controller output ;d1 = emulator output
            loada.fl    EMact+EMLOUT+0             ;get output layer
            output.alu                             ;sendout ;d2 = shaker error
            output.fil  shakererror                ;sendout ;d3 = eact output
            output.fil  fltrdx                     ;filtered x output ;end the message
            pktend                                 ;send packet
            rts
;;; ############

;;; DTADDPAT
;;;
;;; load the inputs from the a/d card through the dt connect bus DTADDPAT    ;select the dai 1016 for read/write
            sib.fil     seldai                     ;select dai address
            sib.fil     selcs                      ;set dai command status mode
            output.fil  daimode                    ;extension at bit 15
            sib.fil     selrv                      ;set dai 1016 for read/write mode ;send timing blip to data translation d/a
            loadlc.im   0xffffff                   ;setup timing loop count
            jmpn.lc     DTERROR                    ;error if count zero
            jmpn.of     &&-1                       ;wait if output is full
            output.fil  onevolt                    ;d/a 0 high
            output.fil  onevolt                    ;d/a 1 high
            loadlc.im   0xffffff                   ;setup timing loop count
            jmpn.lc     DTERROR                    ;error if count zero
            jmp.ip      &&-1                       ;wait if input empty
            output.fil  zerovolts
            output.fil  zerovolts INPUTLOOP   ;input a/d values from fifo until no input pending
            #for i = 0 to NADCHAN                  ;do for every a/d channel
                    loadlc.im  0xffffff            ;setup timing loop count
                    jmpn.lc    DTERROR             ;error if count zero
                    jmp.ip     &&-1                ;wait if input empty input.alu                      ;get a/d data
                    sicf.alu                       ;convert to float
                    loada.alu                      ;move to apy
                    mult.fil   scalefact           ;scale to -.5 to .5
                    storem.fil ad[i]               ;store scaled input
            #endfor
            jmpn.ip     INPUTLOOP                  ;if not empty get NADCHAN more values ;reselect the host
            sib.fil     selcs                      ;set dai command status mode
```

```
                output.fil   daimode1              ;disable nrts on the dai
                sib.fil      selhost               ;reselect the host RETURN_OK()
DTERROR
                output.fil   zerovolts
                output.fil   zerovolts
                sib.fil      selcs                 ;set dai command status mode
                output.fil   daimode1              ;disable nrts on the dai
                sib.fil      selhost               ;reselect the host ;set outputs with error messages to the host
                loada.im     0                     ;zero outputs sent to host
                storea.fl    CTact+CTLOUT+0
                storea.fl    EMact+EMLOUT+0
                storea.fil   shakererror
                storea.fil   ctout
                loada.fil    errflag               ;set error flag
                #for i = 0 to NADCHAN
                        storea.fil   ad[i]         ;errors in ad registers
                #endfor
                rts                                ;return with error alu # 0
;;; ############

;;; INPUTFILTERS
;;;
;;; digital filters for a/d inputs

INPUTFILTERS
                HPFLTRCHAN (ad[0],hpd1[0],hpd2[0],hpo1[0])
                HPFLTRCHAN (ad[2],hpd1[2],hpd2[2],hpo1[2])
                rts AD1FILTER   HPFLTRCHAN (ad[1],hpd1[1],hpd2[1],hpo1[1])
                rts CTOUTFILTER HPFLTRCHAN (ad[3],hpd1[3],hpd2[3],hpo1[3])
                rts LOWPASSOUTPUT
                #for i = 0 to CTLSIZEOUT
                        LPFLTRCHAN (ctdc[i],lpd1[i],lpd2[i])
                #endfor
                rts
;;; ############

;;; ADJ_CTLRATE
;;;
;;; adjust the lrate of the controller based on the square error ADJ_CTLRATE
                ;shift the sqr_err time series
                SHIFTSERIES(sqr_err,1,SUMSIZE)

;add square of the error
                sqr.fil      shakererror           ;apy = shakererror^2
                storea.fl    sqr_err + 0           ;store apy in sqr_err series ;sum square errors
                loada.fl     sqr_err+0             ;alu = sqr_err0 (set seg register)
```

```
#for i=1 to SUMSIZE
        add.low      sqr_err + i      ;alu = sum(sqr_err)
endfor ;convert to lrate
loada.alu                             ;mpy = alu
mult.fil     pt_005                   ;mpy = sum*.005 (scale factor)
addmpy.fil   ctlr4                    ;alu = mpy + lrate
storea.fil   ctlr4                    ;alu => ct_lrate
rts
```

;;;############

;;; TIME_DELAYS
;;;
;;; time delay signals up to tdsize

DELAY_CTGT
```
             ;shift the target time series and add new ctarget value
             jsr         CTGTIMESTEP
             loada.fil   ctarget              ;shift in new ctarget value
             storea.fl   CTtgtdel+0

;get the delayed ad0 value and store in ad0
             loada.fil   tgtd                 ;get delay offset
             fcsi.alu                         ;convert to integer
             loada.im    &CTtgtdel            ;mpy = address of time series input
             iadd.mpy                         ;alu = address + tgtd
             loada.fl    @alu                 ;load delayed ctarget
             storea.fil  ctarget              ;store delayed ctarget
             rts
```

;;; ############

;;; ADDTIMESTEP
;;;
;;; decode number of time series inputs and jump to proper shift routine
;;; which shifts one time step for every time series up to four
;;; note that the oldest data is at act[0]

CTADDTIMESTEP
```
             loada.im    CTNSERIES           ;get shift amount
             rts.zr                          ;return if zero
             SHIFTSERIES(CTact,CTNSERIES,CTLSIZE0) ;do the shift
             rts
```

EMADDTIMESTEP
```
             loada.im    EMNSERIES           ;get shift amount
             rts.zr                          ;return if zero
             SHIFTSERIES(EMact,EMNSERIES,EMLSIZE0) ;do the shift
             rts
```

EMCTADDTIMESTEP
```
             loada.im    EMNSERIES           ;get shift amount
             rts.zr                          ;return if zero
             SHIFTSERIES(EMCTact,EMNSERIES,EMLSIZE0) ;do the shift
             rts
```

CTFXADDTIMESTEP
```
             loada.im    CTNSERIES           ;get shift amount
             rts.zr                          ;return if zero
```

```
                    SHIFTSERIES(CTFXact,CTNSERIES,CTLSIZE0) ;do the shift
                    rts CT6TIMESTEP
                    loada.fil    tgtd                    ;get shift amount
                    rts.zr                               ;do not bother if zero
                    SHIFTSERIES(CTtgtdel,1,TDSIZE)       ;do the shift
                    rts

;;; ############

;;; SIGMOID
;;; Register usage:
;;;     r0: index i into table
;;;     r1: fractional index
;;;     r2: sigtable[i]
;;;     r3: SIGx forg
        SIGNegMag    =    0xc1400000      ; IEEE -12.0
        SIGPosMag    =    0x41400000      ; IEEE 12.0
        SIGMin       =    0xc2200000      ; IEEE -40.0
        SIGMax       =    0x42200000      ; IEEE 40.0
        SIGFix       =    0x34679802      ; IEEE 2.156885153e-7 (from "sigmoid.c")
        SIGMaxTable  =    0x3effff32      ; IEEE .499993861 (from "sigmoid.c")
        SIGTCDivRange =   0x42aa9555      ; IEEE 2047.0/24.0 (TABLE_COUNT-1)/RANGE
        SIGMaxResult =    0x3effffff      ; IEEE 0.4999999999
porg $$

SIGMOID        storea.fil   r3
               capr.fil     SIGNegMag
               japn.cry     SIGCont1        ; jmp if (x >= -MAGNITUDE)
               loada.fil    r3
               capr.fil     SIGMin
               japn.cry     SIGDoMin        ; jmp if (x >= MIN)
               loada.fil    SIGMaxResult
               negx.alu                     ; -.49999999
               rts
SIGDoMin       loada.fil    r3
               add.fil      SIGMax          ; x + MAX
               loada.alu
               mult.fil     SIGFix          ; (x + MAX) * FIX
               loada.mpy
               subx.fil     SIGMaxResult    ; (x + MAX) * FIX - 0.4999999
               rts SIGCont1       loada.fil    r3
               capr.fil     SIGPosMag
               jmp.cry      SIGCont2        ; jmp if (x < MAGNITUDE)
               loada.fil    r3
               capr.fil     SIGMax
               jmp.cry      SIGDoMax        ; jmp if (x < MAX)
               loada.fil    SIGMaxResult    ; .49999999
               rts
SIGDoMax       loada.fil    r3
               subx.fil     SIGPosMag       ; x - MAGNITUDE
               loada.alu
               mult.fil     SIGFix          ; (x - MAGNITUDE) * FIX
               loada.mpy
               add.fil      SIGMaxTable     ; ... + sigtable[COUNT-1]
               rts
```

```
SIGCont2     loada.fil  r3
             add.fil    SIGPosMag     ; x + MAGNITUDE
             loada.alu
             mult.fil   SIGTCDivRange ; (x + MAGNITUDE) * (TC-1) / RANGE
             fcsit.mpy                ; truncate float to integer
             storea.fil r0            ; index into table
             sicf.alu                 ; back to float
             sub.mpy
             storea.fil r1            ; fractional portion
             iaddr0.im  &sigtable     ; index into sigtable[i]
             indir
             loada.fl   0             ; MPY = sigtable[i]
             storea.fil r2
             iaddr0.im  &sigtable+1   ; index into sigtable[i+1]
             indir
             loada.fl   0             ; sigtable[i+1]
             subx.fil   r2            ; sigtable[i+1] - sigtable[i]
             loada.alu
             mult.fil   r1
             loada.mpy
             add.fil    r2
             rts
;;; ########### endprog
```

What is claimed is:

1. Adaptive vibration control apparatus comprising:
   (1) source sensing means for sensing source vibrations in a given medium;
   (2) error sensing means for sensing vibrations at a specified monitoring point in the medium whereat vibrations are to be controlled;
   (3) vibration generating means for generating at least one offsetting vibration that is applied to the medium at at least one location; and
   (4) controller means responsive to the source vibrations sensed by the source sensing means and to the vibrations at the specified monitoring point sensed by the error sensing means for controlling the vibration generating means in real time so as to force the vibrations sensed by the error sensing means below a first level, said controller means comprising an artificial neural network, said artificial neural network having:
   an input layer of a plurality of neurons to which time sequences of an input signal derived from said source sensing means is applied said input signals propagating forward through said network;
   an output layer of at least one neuron providing an output signal for controlling said vibration generating means;
   at least one intermediate layer of a plurality of neurons coupled to said input and output layers;
   said input, output and at least one intermediate layers being responsive to at least one error signal derived from said error sensing means so as to adapt the amount of coupling that occurs between said input, intermediated said output layers as said input signal propagates therethrough.

2. The adaptive vibration control apparatus as set forth in claim 1 further including means for generating the derivative of said input signal and applying time sequences of said derivative to a portion of said input layer.

3. The adaptive vibration control apparatus as set forth in claim 2 wherein said artificial neural network further includes at least one set of a plurality of direct connections between said input layer and said output layer.

4. The adaptive vibration control apparatus as set forth in claim 3 wherein said artificial neural network includes two intermediate layers, each intermediate layer having at least eight neurons.

5. The adaptive vibration control apparatus as set forth in claim 4 wherein said first level below which said sensed vibration is forced by said controller means comprises a vibration level approximately equal to zero, whereby said vibration control apparatus effectively cancels the sensed vibration at the specified monitoring point.

6. The adaptive vibration control apparatus as set forth in claim 4 wherein said first level below which said sensed vibration is forced by said controller means comprises a time-varying reference value that changes as a function of time, whereby said vibration control apparatus functions as a vibration generator that generates a vibration that follows said time-varying reference value.

7. The adaptive vibration control apparatus as set forth in claim 1 wherein said controller means includes:
   means for emulating said vibration generating means using a first artificial neural network;
   a second artificial neural network coupled to said first artificial network, said second artificial network being adapted to control said vibrating generating means;
   wherein each of said first and second artificial neural networks comprises:
   an input layer of a plurality of neurons to which time sequences of an input signal is applied, said input signal propagating forward through said network, an output layer of at least one neuron providing an output signal
at least one intermediate layer of a plurality of neurons coupled to said input and output layers;
wherein said input, output and at least one intermediate layers, are responsive to at least one error signal so as to adapt the amount of coupling that occurs between said input, intermediate, and output layers as said input signal propagates therethrough; and further
wherein the input signal applied to the first artificial neural network is derived from the error sensing means, the input signal applied to the second artificial neural network is derived from the source sensing means, the output signal of the second artificial neural network drives said vibration generating means, the output signal from the first artificial neural network is compared with the output signal from the second artificial neural network to generate a first error signal that is applied to the first artificial neural network, and the input signal applied to the first artificial neural network is compared with the input signal applied to the second artificial neural network to generate a second error signal that is applied to the second artificial neural network.

8. The adaptive vibration control apparatus as set forth in claim 1 further including
a first artificial neural network (36x) that emulates said vibration generating means (34);
a second artificial neural network (32x) that controls said vibrating generating means;
a third artificial neural network (40x) coupled to said first artificial neural network; and
a fourth artificial neural network (38x) coupled to said second artificial neural network;
wherein each of said first, second, third and fourth artificial neural networks comprises:
an input layer of a plurality of neurons to which time sequences of an input signal is applied, said input signal propagating forward through said network,
an output layer of at least one neuron providing an output signal,
at least one intermediate layer of a plurality of neurons coupled to said input and output layers;
weighting means for defining the amount of coupling that occurs between said input, intermediate, and output layers as said input signal propagates therethrough; and further
wherein the second artificial neural network receives its input signal from the source sensing means (A0), and directs its output signal to the vibration generating means, and
wherein the first artificial neural network receives its input signal from the output signal of the second artificial neural network and compares its output signal with an sensed error signal derived from said error sensing means (39) to produce a first error signal, said first error signal being applied to the weighting means of the first artificial neural network; and
wherein the third artificial neural network receives its input signal from the source sensing means, and directs its output signal to the fourth artificial neural network; and
wherein the fourth artificial neural network receives its input signal from the output signal of the third artificial neural network, and wherein a second error signal is applied to the weighting means of the fourth artificial neural network, the second error signal being derived from the source sensing means and error sensing means;
wherein the weighting means of the second artificial neural network track the weighting means of the fourth artificial neural network; and the weighting means of the third artificial neural network track the weighting means of the first artificial neural network.

* * * * *

UNITED STATES PATENT AND TRADEMARK OFFICE
CERTIFICATE OF CORRECTION

PATENT NO. : 5,426,720
DATED : June 6, 1995
INVENTOR(S) : Bozich et al.

It is certified that error appears in the above-indentified patent and that said Letters Patent is hereby corrected as shown below:

Claim 1, column 99, line 51, after "applied" insert --,--. Claim 1, column 99, line 63, change "intermediated" to --intermediate,--. Claim 1, column 99, line 63, change first occurance of "said" to --and--.

Signed and Sealed this

Thirty-first Day of October 1995

Attest:

BRUCE LEHMAN

Attesting Officer

Commissioner of Patents and Trademarks